(12) United States Patent
Matsuka et al.

(10) Patent No.: US 7,771,731 B2
(45) Date of Patent: Aug. 10, 2010

(54) **ALTERED FIBRONECTIN-BINDING PROTEIN OF *STAPHYLOCOCCUS AUREUS***

(75) Inventors: Yury Vladimirovich Matsuka, New Windsor, NY (US); Steven Morris Baker, Highland Mills, NY (US); Elizabeth Teremy Anderson, Lansdale, PA (US)

(73) Assignee: Wyeth LLC, Madison, NJ (US)

( * ) Notice: Subject to any disclaimer, the term of this patent is extended or adjusted under 35 U.S.C. 154(b) by 475 days.

(21) Appl. No.: 11/596,953

(22) PCT Filed: May 17, 2005

(86) PCT No.: PCT/US2005/017186

§ 371 (c)(1),
(2), (4) Date: Nov. 17, 2006

(87) PCT Pub. No.: WO2005/116064

PCT Pub. Date: Dec. 8, 2005

(65) Prior Publication Data

US 2007/0218075 A1 Sep. 20, 2007

Related U.S. Application Data

(60) Provisional application No. 60/573,724, filed on May 21, 2004.

(51) Int. Cl.
*A61K 39/38* (2006.01)
*A61K 30/02* (2006.01)
*A61K 39/085* (2006.01)
*C07K 14/00* (2006.01)
*C07K 17/00* (2006.01)

(52) U.S. Cl. ............... 424/243.1; 424/184.1; 424/190.1; 530/350

(58) Field of Classification Search ........................ None
See application file for complete search history.

(56) References Cited

U.S. PATENT DOCUMENTS

| | | | |
|---|---|---|---|
| 5,175,096 | A | 12/1992 | Hook et al. |
| 5,320,951 | A | 6/1994 | Hook et al. |
| 5,571,514 | A | 11/1996 | Hook et al. |
| 5,593,972 | A | 1/1997 | Weiner et al. |
| 5,652,217 | A | 7/1997 | Hook et al. |

FOREIGN PATENT DOCUMENTS

| | | | |
|---|---|---|---|
| EP | 397633 | A * | 11/1990 |
| WO | WO 96/21356 | | 7/1995 |
| WO | WO 9831389 | * | 7/1998 |

OTHER PUBLICATIONS

Ibrahimi et al. Human Molecular Genetics, 2004, vol. 14, No. 1 69-78.*
Schuster et al. Molecular Microbiology, 1998, 27 (5), 1065-1075.*
Burgess et al. J. of Cell Bio. 111:2129-2138, 1990.*
Lazar et al. Molecular and Cellular Biology, 1988, 8:1247-1252.*
Houghten et al. (New Approaches to Immunization, Vaccines 86, Cold Spring Harbor Laboratory, p. 21-25, 1986.*
Harlow et al, Antibodies A Laboratory Manual, Cold Spring Harbor Laboratory Press Inc., 1988, p. 23-25 and 27-33.*
Colman et al Research in Immunology 145: 33-36, 1994.*
Matsuka et al.; Biochemistry; vol. 42; pp. 14643-14652; 2003.
D. Aeschlimann and M. Paulsson; Thromb. Haemost.; vol. 71; pp. 402-415; 1994.
J. J. Gorman and J. E. Folk; J. Biol. Chem.; vol. 256; pp. 2712-2715; 1981.
J. J. Gorman and J. E. Folk; J. Biol. Chem.; vol. 259; pp. 9007-9010; 1984.
L. Fesus et al.; Eur. J. Biochem.; vol. 154; pp. 371-374; 1986.
A. Henschen and J. Mcdonagh; Blood Coagul.; H. C. Hemker. Amsterdam, Elsevier Science Publishers; pp. 171-241; 1986.
L. Lorand; Ann. N. Y. Acad. Sci.; vol. 936; pp. 291-311; 2001.
L. Lorand and R. M. Graham; Nature; vol. 4; pp. 140-156; 2003.
C. Signas et al.; Proc. Natl. Acad. Sci. USA; vol. 86; pp. 699-703; 1989.
O. Schneewind et al.; Science; vol. 268(5207); pp. 103-106; 1995.
L. Lorand, N.G. Rule et al.; Biochemistry; vol. 7; pp. 1214-1223; 1968.
L. Lorand, G. E. Siefring et al.; Anal. Biochem.; vol. 93; pp. 453-458; 1979.
K. Parameswaran, P. Velasco et al.; Proc. Natl. Acad. Sci. USA; vol. 87; pp. 8472-8475; 1990.
L. Lorand, K. Parameswaran et al.; Bioconjug. Chem.; vol. 3; pp. 37-41; 1992.
J. H. Sobel and M. A. Gawinowicz; J. Biol. Chem.; vol. 271; pp. 19288-19297; 1996.
B. A. Cottrell, D. D. Strong et al.; Biochemistry; vol. 18; pp. 5405-5410; 1979.
R. P. Mcdonagh, J. Mcdonagh et al; FEBS Letters; vol. 127; pp. 174-178; 1981.

(Continued)

*Primary Examiner*—Robert Mondesi
*Assistant Examiner*—Oluwatosin Ogunbiyi
(74) *Attorney, Agent, or Firm*—Darrell Fontenot; Maria Restrepo-Hartwig

(57) ABSTRACT

An isolated, altered fibronectin-binding protein (Fnb) of *S. aureus* having at least one mutation in an amino acid selected from residues corresponding to Gln103, Gln105, Lys157, Lys503, Lys620, Lys702, Lys762, Gln783 and Gln830 of FnbA of *S. aureus* strain ATCC49525 is described. Replacement of these reactive residues within the fibronectin-binding protein renders this protein less capable than wild-type Fnb of covalently cross-linking with fibronectin and fibrin. The altered fibronectin-binding protein effectively interferes with adhesion of *S. aureus* to fibronectin and fibrin, and therefore, an immunogenic composition comprising such altered Fnb exhibits improved immunogenic properties and is safer to use.

10 Claims, 14 Drawing Sheets

OTHER PUBLICATIONS

Y. Matsuka, L. Medved et al.; Biochemistry; vol. 35; pp. 5810-5816; 1996.
K. House-Pompeo, Y. Xu e t al; J. Biol. Chem; vol. 271; pp. 1379-1384; 1996.
J. C. Penkett, C. Redfield et al.; J. Mol. Biol.; vol. 274; pp. 152-159; 1997.
C. Penkett, C. Redfield et al; Biochemistry; vol. 37; pp. 17054-17067; 1998.
J. J. Grootjans, P.J.T.A. Groenen et al.; J. Biol. Chem.; vol. 270; 22855-22858; 1995.
K. Jonsson, C. Signas et al.; Eur. J. Biochem; vol. 202; pp. 1041-1048; 1991.
T. Baba et al.; The Lancet; vol. 359; pp. 1819-1827; 2002.
M. Kuroda, T. Ohta et al.; The Lancet; vol. 357; pp. 1225-1240; 2001.
J.D. Thompson, D. G. Higgins et al.; Nucleic Acids Res.; vol. 22; pp. 4673-4680; 1994.
M.W. Mosesson; Semin. Hematol.; vol. 29; pp. 177-188; 1992.
F. Grinnel, M. Feld et al.; Cell; vol. 19; pp. 517-525; 1980.
P. Knox, S. Crooke et al.; The J. Cell Biol.; vol. 102; pp. 2318-2323; 1986.
S. A. Corbett, L. Lee et al.; J. Biol. Chem.; vol. 272; pp. 24999-25005; 1997.
Y. V. Matsuka, L. V. Medved et al.; The J. Biol. Chem.; vol. 269(13); pp. 9539-9546; 1994.
Y. Matsuka, M. Migliorini et al.; J Prot Chem; vol. 16; pp. 739-745; 1997.
Cunningham and Wells; Science; vol. 244; pp. 1081-1085; 1989.
Bowie et al.; Science; vol. 247; pp. 1306-1310; 1990.
Current Protocols in Molecular Biology, John Wiley & Sons, NY; pp. 6.3.1-6.3.6; 1989.
Goeddel; Gene Expression Technology; Methods in Enzymology 185, Academic Press, San Diego, CA.; pp. 3-7; 1990.
Broach et al.; Experimental Manipulation of Gene Expression, ed. M. Inouye, Academic Press; pp. 83-117; 1983.
Sambrook et al.; Molecular Cloning: A Laboratory Manual, $2^{nd}$ ed., Cold Spring Harbor Laboratory Press; Chapters 16 and 17; 1989.
Bernatowicz and Matsueda; Anal. Biochem.; vol. 155; pp. 95-102; 1986.
Frisch et al.; Bioconjug. Chem.; vol. 7; pp. 180-186; 1996.
Boeckler et al.; J. Immunol. Methods; vol. 191; pp. 1-10; 1996.
J. Takagi, T. Aoyama et al.; Eur. J. Biochem; vol. 232; pp. 773-777; 1995.
S. Clement, P. T. Velasco et al.; J. Biol. Chem.; vol. 273(13); pp. 7604-7609; 1998.
F. D. Lowy; The N. Engl. J. Med.; vol. 339; pp. 520-532; 1998.
J.M. Patti, B.L. Allen et al.; Annu. Rev. Microbiol; vol. 48; pp. 585-617; 1994.
R.A.S.Ariens, T.S. Lai et al; Blood; vol. 100; pp. 743-754; 2002.
E.T. Anderson, L. Fletcher et al; Biochemistry; vol. 43; pp. 11842-11852; 2004.
Q. Sun et al; Identification of D Motif Epitopes in *Staphylococcus aureus* Fibronectin-Binding Protein for the Production of Antibody Inhibitors of Fibronectin Binding; Infect. Immun., American Society for Microbiology.; vol. 65(2); pp. 537-543; 1997.

* cited by examiner

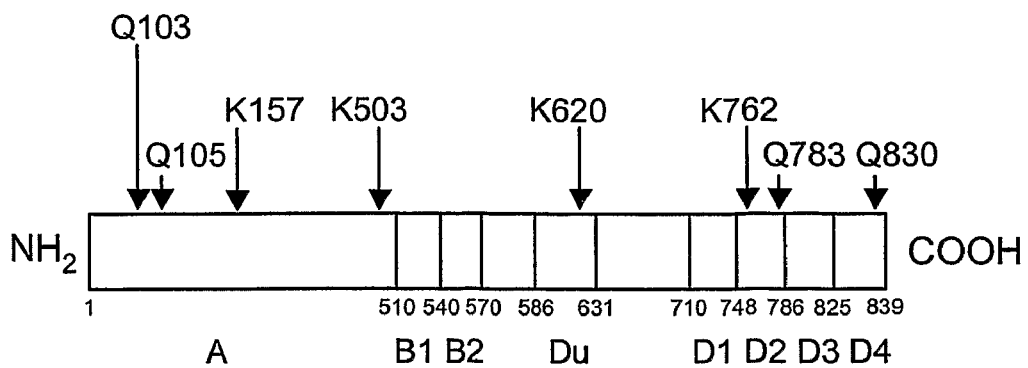

```
ASEQKTTTVEENGNSTTDNKVSETQTTTTNVNHIEETQSYNATVTEQPSN    50
ATQVTTEEAPKAVQAPQTAQPANVEKVKEEVVKEEAKPQVKETTQSQDNS   100
GDQRQVDLIPKKATQNQVAETQVEVAQPRTVSESKPRVTRSADVVEAKEG   150
MGVSEVKGTDVTSKVTVESGSIEAPQGNKVEPHAGQRVVLKYKLKFADGL   200
KRGDYFDFTLSNNVNTYGVSTARKVPEIKNGSVVMATGEILGNGNIRYTF   250
TNEIEHKVEVTANLEINLFIDPKTVQSDGEQKITSKLNGEETEKTIPVVY   300
NPGVSNSYTNVNGSIETFNKESNKFTHIAYIKPMNGNQSNTVSVTGTLTE   350
GSNLAGGQPTVKVYEYLGKKDELPQSVYANTSDTNKFKDVTNEMNGKLSV   400
QDNGSYSLNLDKLDKTYVIHYTGEYLQGSDQVNFRTELYGYPERAYKSYY   450
VYGGYRLTWDNGLVLYSNKADGNGKNGQIIQNNDFEYKEDTAKGTMSGQY   500
DAKQIIETEENQDNTPLDIDYHTAIDGEGGYVDGYIETIEETDSSAIDID   550
YHTAVDSEAGHVGGYTESSEESNPIDFEESTHENSKHHANVVEYEEDTNP   600
GGGQVTTESNLVEFDEESTKGIVTGAVSDHTTVEDTKEYTTESNLIELVD   650
ELPEEHGQAQGPIEEITENNHHISHSGLGTENGHGNYGVIEEIEENSHVD   700
IKSELGYEGGQNSGNQSFEEDTEEDKPKYEQGGNIVDIDFDSVPQIQGQN   750
NGNQSFEEDTEKDKPKYEQGGNIIDIDFDSVPQIHGFNKHNEIIEEDTNK   800
DKPNYQFGGHNSVDFEEDTLPKVSGQNEGQQTIEEDTTP              839
```

FIG. 5

| Strain | Q103 | Q105 | K157 | K503 | K620 | K762 | SEQ ID NO: |
|---|---|---|---|---|---|---|---|
| FnbA ATCC49525 | DNSGD | QRQVDLIP | GVSEVKGTDVT | GQYDAKQIIET | DEESTKGIVTG | EEDTEKDKPKY | 1 |
| Mu50 | DNSGN | QRQVDLTP | DVSEVKGTDVT | GQYDAKQIIET | DEESTKGIVTG | EEDTEKDKPKY | 2 |
| N315 | DNSGN | QRQVDLTP | DVSEVKGTDVT | GQYDAKQIIET | DEESTKGIVTG | EEDTEKDKPKY | 3 |
| MW2 | DNSGD | QRQVDLTP | DEKVETGTDVT | GQYDAKQIIET | DEESTKGIVTG | EEDTEKDKPKY | 4 |
| MSSA-476 | DNSGD | QRQVDLTP | DEKVETGTDVT | GQYDAKQIIET | DEESTKGIVTG | EEDTEKDKPKY | 5 |
| COL | DNSGD | QRQVDLTP | NAKVETGTDVT | GQYDKNLVTTV | DEESTKGIVTG | EEDTEKDKPKY | 6 |
| 8325-4 | DNSGD | QRQVDLTP | NAKVETGTDVT | GQYDKNLVTTV | DEESTKGIVTG | EEDTEKDKPKY | 7 |
| EMRSA-16 | DNSGD | QRQVDLTP | DAKVETGTDVT | GQYDAKQIIET | DEESTKGIVTG | ------------ | 8 |
| FnbB Mu50 | ------ | KSQEDLPS | EEAKATGTDVT | -----DPIIEK | DEESTKGIVTG | EEDTEEDKPKY | 9 |
| N315 | ------ | KSQEDLPS | EEAKATGTDVT | -----DPIIEK | DEESTKGIVTG | EEDTEEDKPKY | 10 |
| MW2 | ------ | SRVDLPS | EEAKATGTDVT | -----DPIIEK | DEESTKGILTG | EEDTEKDKPKY | 11 |
| MSSA-476 | ------ | SRVDLPS | EEAKATGTDVT | -----DPIIEK | DEESTKGILTG | EEDTEKDKPKY | 12 |
| COL | ------ | SRVDLPS | EETKATGTDVT | -----EPIIEH | DEDSTKGIVTG | EEDTEKDKPKY | 13 |
| 8325-4 | ------ | SRVDLPS | EETKATGTDVT | -----EPIIEH | DEDSTKGIVTG | EEDTEKDKPKY | 14 |

| Strain Cont'd | Q783 | Q830 | SEQ ID NO: |
|---|---|---|---|
| FnbA ATCC49525 | FDSVPQIHGFN | GQNEGQQTIEE | 1 |
| Mu50 | FDSVPQIHGFN | GQNEGQQTIEE | 2 |
| N315 | FDSVPQIHGFN | GQNEGQQTIEE | 3 |
| MW2 | FDSVPQIHGFN | GQNEGQQTIEE | 4 |
| MSSA-476 | FDSVPQIHGFN | GQNEGQQTIEE | 5 |
| COL | FDSVPQIHGFN | GQNEGQQTIEE | 6 |
| 8325-4 | FDSVPHIHGFN | GQNEGQQTIEE | 7 |
| EMRSA-16 | FDSVPHIHGFN | GQNEGQQTIEE | 8 |
| FnbB Mu50 | FDSVPQIHGFN | GQNEGQQTIEE | 9 |
| N315 | FDSVPQIHGFN | GQNEGQQTIEE | 10 |
| MW2 | FDSVPHIHGFN | GHNEGQQTIEE | 11 |
| MSSA-476 | FDSVPHIHGFN | GHNEGQQTIEE | 12 |
| COL | FDSVPHIHGFN | GHNEGQQTIEE | 13 |
| 8325-4 | FDSVPHIHGFN | GHNEGQQTIEE | 14 |

FIG. 6

| Strain | | K702 |
|---|---|---|
| FnbA | ATCC49525 | SHVDIKSELGY |
| | Mu50 | SHVDIKSELGY |
| | N315 | SHVDIKSELGY |
| | MW2 | SHVDIKSELGY |
| | MSSA-476 | SHVDIKSELGY |
| | COL | SHVDIKSELGY |
| | 8325-4 | SHVDIKSELGY |
| | EMRSA-16 | SHVDIKSELGY |
| FnbB | Mu50 | SHVDIKSELGY |
| | N315 | SHVDIKSELGY |
| | MW2 | SHVDIKSELGY |
| | MSSA-476 | SHVDIKSELGY |
| | COL | SHVDIKSELGY |
| | 8325-4 | SHVDIKSELGY |

Fig. 14

ALTERED FIBRONECTIN-BINDING PROTEIN OF STAPHYLOCOCCUS AUREUS

This application is the US national phase of international application PCT/US2005/017186 filed on May 17, 2005, which designated the US and claims priority to U.S. Provisional Application No. 60/573,724, filed on May 21, 2004. The entire contents of these applications are incorporated herein by reference.

FIELD OF THE INVENTION

The present invention relates to an altered fibronectin-binding protein of Staphylococcal *aureus* having reduced reactivity to coagulation Factor XIIIa. Immunogenic compositions comprising this altered fibronectin-binding protein have improved antigenic properties and are safer to use.

BACKGROUND OF THE INVENTION

Staphylococcal *aureus* (*S. aureus*) fibronectin-binding protein (Fnb) is a surface-associated multifunctional receptor responsible for specific reversible binding to human proteins such as fibronectin, fibrin and fibrinogen. Such binding allows the microorganism to effectively attach and subsequently invade and colonize the human host during surgeries, vascular injuries, etc. Fnb has been evaluated as a potential candidate for inclusion in immunogenic compositions to prevent *S. aureus* infections. Immunization with recombinant Fnb and the generation of functionally active antibodies against this protein potentially can prevent the initial attachment of *S. aureus* to human tissues, and therefore, prevent infection. Recent studies, however, indicate that antibodies generated in mice, rabbits and humans do not inhibit binding of wild-type Fnb to human fibronectin and fibrinogen. Rather, they induce binding of Fnb to these human proteins, and thus, enhance bacterial adherence to the host tissue. This indicates that reversible binding to human proteins serves only as an initial phase in the process of staphylococcal adhesion to the host tissue.

In a recent study, it was demonstrated that staphylococcal fibronectin-binding protein A (FnbA) serves as a substrate for the human enzyme called plasma transglutaminase (Matsuka et al. 2003). This is a novel function, previously unknown for FnbA. Plasma transglutaminase (also known as Factor XIIIa) is an enzyme that catalyzes covalent (irreversible) cross-linking of a very limited number of human proteins (Table 1) resulting in the formation of high molecular mass homo- and heteropolymers. Factor XIII is a member of the transglutaminase family of enzymes that catalyze the formation of isopeptide bond(s) either within or between polypeptide chains. Factor XIII circulates in the blood and is therefore considered to be an extracellular enzyme, whereas tissue transglutaminases (TG) (e.g., liver TG, keratinocyte TG, epidermal TG, prostate TG and erythrocyte TG) are located inside the cells, and therefore, act as intracellular enzymes (Aeschlimann et al. 1994). Distinct transglutaminases recognize the same protein as substrate, but often with a different affinity and/or specificity. Overall, the substrate specificity for Factor XIIIa is more stringent than for tissue transglutaminases (Gorman et al. 1981; Gorman et al. 1984; Fesus et al. 1986).

Cross-linking reactions catalyzed by Factor XIIIa are important steps in various normal physiological reactions including blood coagulation, wound healing, and fibrinolysis. Factor XIIIa-catalyzed protein cross-linking takes place via formation of covalent bonds between specific glutamine (Gln) and lysine (Lys) amino acid residues. It has been demonstrated that FnbA can be readily cross-linked to human fibronectin and fibrin by Factor XIIIa (Matsuka et al. 2003). Thus, upon immunization with FnbA, FnbA undergoes immediate covalent (irreversible) cross-linking to fibronectin and fibrin. This formation of an irreversible complex of an antigen with human proteins very likely compromises the immune response and leads to the production of antibodies that lack inhibitory/neutralizing activity.

Thus, there is a need to identify the specific reactive amino acid residues (Gln and Lys) within wild-type staphylococcal fibronectin-binding protein that are directly involved in Factor XIIIa-catalyzed covalent cross-linking with human proteins, and substitute those residues to produce an altered form of Fnb that has reduced reactivity to coagulation Factor XIIIa and will effectively inhibit cross-linking and irreversible binding to fibronectin and fibrin.

SUMMARY OF THE INVENTION

Accordingly, this invention pertains to an isolated, altered fibronectin-binding protein (Fnb) of *S. aureus*, wherein the alteration is a mutation of at least one amino acid selected from the group consisting of residues corresponding to glutamine (Gln)103, Gln105, lysine (Lys)157, Lys503, Lys620, Lys762, Gln783 and Gln830 of the FnbA of *S. aureus* strain ATCC49525, wherein the altered Fnb is less capable than wild-type Fnb of covalently cross-linking with human proteins that serve as a substrate for Factor XIII, Factor XIIIa or tissue transglutaminase, and the human proteins are selected from the group consisting of fibronectin and fibrin. In one embodiment, these amino acids are mutated to alanine. In a further embodiment, the isolated, altered Fnb is derived from FnbA or FnbB.

The invention also relates to an altered Fnb as just described, wherein the alteration is a mutation of the amino acid Lys702.

The invention also relates to an altered Fnb as just described, wherein the alteration is a mutation of at least one amino acid selected from the group consisting of the residues of the protein and *S. aureus* strain as follows:

| Protein | Strain | Residues |
| --- | --- | --- |
| FnbA | Mu50 | Gln134, Gln136, Lys188, Lys534, Lys651, Lys793, Gln814, Gln861 |
| FnbA | N315 | Gln134, Gln136, Lys188, Lys534, Lys651, Lys793, Gln814, Gln861 |
| FnbA | MW2 | Gln139, Gln141, Lys539, Lys656, Lys798, Gln819, Gln866 |
| FnbA | MSSA-476 | Gln147, Gln149, Lys547, Lys664, Lys806, Gln827, Gln874 |
| FnbA | COL | Gln139, Gln141, Lys655, Lys797, Gln865 |
| FnbA | 8325-4 | Gln139, Gln141, Lys655, Lys797, Gln865 |
| FnbA | EMRSA-16 | Gln147, Gln149, Lys549, Lys666, Gln791, Gln838 |
| FnbB | Mu50 | Gln111, Lys602, Gln765, Gln812 |
| FnbB | N315 | Gln111, Lys602, Gln765, Gln812 |
| FnbB | MW2 | Lys598, Lys740, Gln808 |
| FnbB | MSSA-476 | Lys598, Lys740, Gln808 |
| FnbB | COL | Lys591, Lys733, Gln801 |
| FnbB | 8325-4 | Lys591, Lys733 Gln801 |

This invention also pertains to an isolated nucleic acid molecule encoding an altered fibronectin-binding protein of *S. aureus*, wherein the alteration is a mutation of at least one amino acid selected from the group consisting of residues corresponding to Gln103, Gln105, Lys157, Lys503, Lys620, Lys762, Gln783 and Gln830 of the FnbA from *S. aureus* strain ATCC49525, wherein the altered fibronectin-binding protein retains immunogenicity and, when incorporated into an immunogenic composition and administered to a vertebrate, is less capable than wild-type Fnb of covalently cross-linking with human proteins that serve as a substrate for Factor XIII, Factor XIIIa or tissue transglutaminase, and the human proteins are selected from the group consisting of fibronectin and fibrin.

The invention also relates to an isolated nucleic acid molecule as just described, wherein the alteration is a mutation of the amino acid Lys702.

The invention also pertains to a nucleic acid construct comprising an isolated nucleic acid molecule described herein operably linked to a regulatory sequence.

The invention also relates to a recombinant host cell comprising a nucleic acid construct described herein, as well as to a method of producing an altered fibronectin-binding protein of S. aureus described herein, the method comprising maintaining a recombinant host cell of the invention under conditions suitable for expression of the altered fibronectin-binding protein.

The invention also pertains to the use of the altered fibronectin-binding protein, or recombinant host cell for expression thereof, to prepare immunogenic compositions that elicit an immune response against S. aureus.

The invention further relates to an immunogenic composition comprising a physiologically acceptable vehicle and an altered fibronectin-binding protein of S. aureus which retains immunogenicity and, when incorporated into the immunogenic composition and administered to the vertebrate, is less capable than wild-type Fnb of covalently cross-linking with human proteins that serve as a substrate for Factor XIII, Factor XIIIa or tissue transglutaminase, such as fibronectin and fibrin. The altered Fnb does not enhance binding of wild-type Fnb to fibronectin and fibrin upon subsequent infection of the vertebrate with S. aureus. The alteration is a mutation of at least one amino acid selected from the group consisting of residues corresponding to Gln103, Gln105, Lys157, Lys503, Lys620, Lys762, Gln783 and Gln830 of the FnbA from S. aureus strain ATCC49525. The immunogenic composition can also comprise an adjuvant.

The invention also relates to an immunogenic composition comprising a physiologically acceptable vehicle and a nucleic acid molecule encoding an altered Fnb of S. aureus, wherein the alteration is a mutation of at least one amino acid selected from the group consisting of residues corresponding to Gln103, Gln105, Lys157, Lys503, Lys620, Lys762, Gln783 and Gln830 of the FnbA of S. aureus strain ATCC49525, where the altered Fnb retains immunogenicity and, when incorporated into the immunogenic composition and administered to a vertebrate, the altered Fnb is less capable than wild-type Fnb of covalently cross-linking with human proteins that serve as a substrate for Factor XIII, Factor XIIIa or tissue transglutaminase, the human proteins being selected from the group consisting of fibronectin and fibrin, and does not enhance binding of wild-type Fnb to fibronectin and fibrin upon subsequent infection of the vertebrate with S. aureus.

The invention also relates to immunogenic compositions as just described, wherein the alteration is a mutation of the amino acid Lys702.

The invention also relates to a method of immunizing a vertebrate against S. aureus, comprising administering to the vertebrate a composition comprising a physiologically acceptable vehicle and an immunologically effective amount of an altered fibronectin-binding protein of S. aureus, wherein the alteration is a mutation of at least one amino acid selected from the group consisting of residues corresponding to Gln103, Gln105, Lys157, Lys503, Lys620, Lys762, Gln783 and Gln830 of the FnbA of S. aureus strain ATCC49525, where the altered fibronectin-binding protein retains immunogenicity and, when incorporated into an immunogenic composition and administered to a vertebrate, is less capable than wild-type Fnb of covalently cross-linking with human proteins that serve as a substrate for Factor XIII, Factor XIIIa or tissue transglutaminase, such as fibronectin and fibrin, and does not enhance binding of wild-type fibronectin-binding protein to said human proteins upon subsequent infection of the vertebrate with S. aureus.

The invention further relates to a method of immunizing a vertebrate against S. aureus, comprising administering to the vertebrate a composition comprising a physiologically acceptable vehicle and an immunologically effective amount of a nucleic acid molecule encoding an altered S. aureus fibronectin-binding protein, optionally with a transfection-facilitating agent, wherein the alteration is a mutation of at least one amino acid selected from the group consisting of residues corresponding to Gln103, Gln105, Lys157, Lys503, Lys620, Lys762, Gln783 and Gln830 of the FnbA of S. aureus strain ATCC49525, where the altered fibronectin-binding protein retains immunogenicity and, when incorporated into an immunogenic composition and administered to a vertebrate, is less capable than wild-type Fnb of covalently cross-linking with human proteins that serve as a substrate for Factor XIII, Factor XIIIa or tissue transglutaminase, such as fibronectin and fibrin, and does not enhance binding of wild-type fibronectin-binding protein to said human proteins upon subsequent infection of the vertebrate with S. aureus.

In one embodiment, the vertebrate is a seronegative human.

The invention also relates to methods of immunizing as just described, wherein the alteration is a mutation of the amino acid Lys702.

BRIEF DESCRIPTION OF THE DRAWINGS

FIG. 5 depicts the location of Factor XIIIa-reactive Gln and Lys residues within the amino acid sequence of wild-type FnbA. It is a schematic illustration of the structural organization of the rFnbA (residues Ala1-Pro839) of *S. aureus* strain ATCC49525 used in this study (top) and its amino acid sequence (bottom) (SEQ ID NO:1). FIG. 5 shows the location of the major regions: A—fibrinogen-binding region; B1 and B2—homologous repeats of unknown function; Du, D1, D2, D3, and D4—fibronectin-binding repeats. Arrows show the positions of Factor XIIIa-reactive Gln (103, 105, 783, and 830) and Lys (157, 503, 620, and 762) residues within the A, Du, D2, and D4 regions of FnbA. Bold letters denote the same Factor XIIIa-reactive Gln and Lys residues in the primary sequence of FnbA. Underlined letters depict the location of the predicted thrombin cleavage site Arg202-Gly203.

FIG. 6 depicts the alignment of the amino acid sequences of FnbA and FnbB species of various *S. aureus* strains set forth in SEQ ID NOS:1-14. Regions surrounding Factor XIIIa-reactive Gln and Lys residues are shown. Positions of the identified reactive Gln and Lys residues at the top correspond to that of FnbA of *S. aureus* strain ATCC49525. The bold letters in the primary sequences of FnbA and FnbB species highlight conserved Factor XIIIa-reactive Gln acceptor and Lys donor sites. Multiple sequence alignment was performed using the CLUSTAL W (1.81) program. Table AA depicts the positions in the amino acid sequence of each *S. aureus* strain of the amino acids comprising the regions surrounding Factor XIIIa-reactive Gln and Lys residues Gln103 and Gln105, Lys157, Lys503, Lys620, Lys762, Gln783, and Gln830.

TABLE AA

Amino acids surrounding the reactive Lys and Gln residues

| SEQ ID | Position of the amino acids surrounding each reactive residue in the indicated SEQ ID NO: | | | | | | |
|---|---|---|---|---|---|---|---|
| | Gln103 and Gln105 | Lys157 | Lys503 | Lys620 | Lys762 | Gln783 | Gln830 |
| 1 | 98-110 | 152-162 | 498-508 | 615-625 | 757-767 | 778-788 | 815-825 |
| 2 | 129-141 | 183-193 | 529-539 | 646-656 | 788-798 | 809-819 | 846-856 |
| 3 | 129-141 | 183-193 | 529-539 | 646-656 | 788-798 | 809-819 | 846-856 |
| 4 | 134-146 | 188-198 | 534-544 | 651-661 | 793-803 | 814-824 | 851-861 |
| 5 | 142-154 | 196-206 | 542-552 | 659-669 | 801-811 | 822-832 | 859-869 |
| 6 | 134-146 | 188-198 | 533-543 | 650-660 | 792-802 | 813-823 | 850-860 |
| 7 | 134-146 | 188-198 | 533-543 | 650-660 | 792-802 | 813-823 | 850-860 |
| 8 | 142-154 | 196-206 | 544-554 | 661-671 | | 786-796 | 823-833 |
| 9 | 109-116 | 160-170 | 492-497 | 597-607 | 739-749 | 760-770 | 797-807 |
| 10 | 109-116 | 160-170 | 492-497 | 597-607 | 739-749 | 760-770 | 797-807 |
| 11 | 107-112 | 157-167 | 488-493 | 593-603 | 735-745 | 756-766 | 793-803 |
| 12 | 107-112 | 157-167 | 488-493 | 593-603 | 735-745 | 756-766 | 793-803 |
| 13 | 107-112 | 157-167 | 481-486 | 586-596 | 728-738 | 749-759 | 786-796 |
| 14 | 107-112 | 157-167 | 481-486 | 586-596 | 728-738 | 749-759 | 786-796 |

Figure 7:
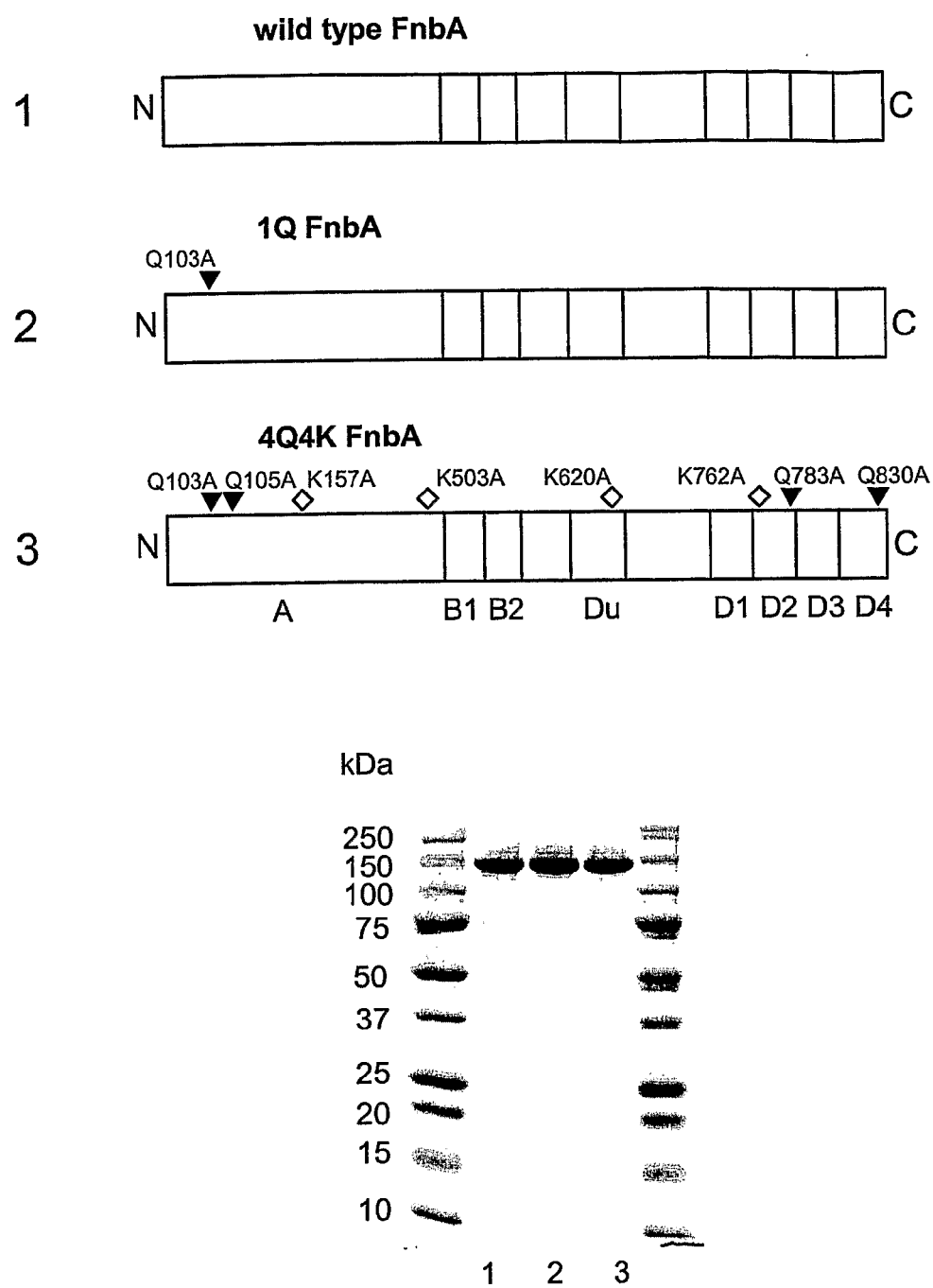

FIG. 7 depicts a schematic representation of the wild type and mutated FnbA species used in this study (top) and SDS-PAGE analysis of the isolated proteins (bottom). This figure shows the location of the major regions in FnbA from *S. aureus* strain ATCC49525: A-fibrin(ogen) binding region; B1 and B2-homologous repeats of unknown function; and Du, D1, D2, D3, D4-fibronectin-binding repeats. The positions of reactive Gln residues and introduced Gln→Ala mutations are indicated by closed triangles while the positions of reactive Lys residues and introduced Lys→Ala mutations are shown by open diamonds. The schematic representation of the FnbA species and SDS-PAGE (4-20% gel) analysis of purified proteins are shown in the following order: 1—wild type FnbA; 2—1Q FnbA mutant; 3—4Q4K FnbA mutant. The outer lanes in the gel contain molecular mass standards as indicated.

Figure 8:
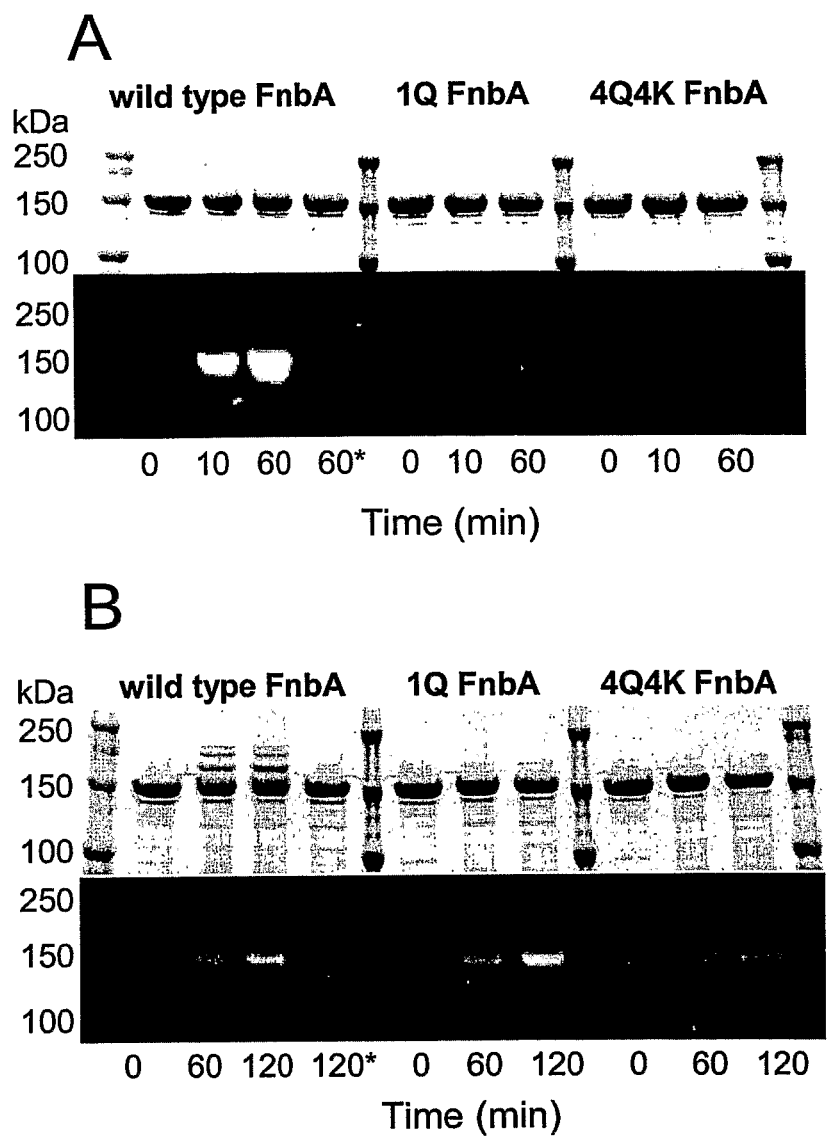

FIG. 8 depicts the Factor XIIIa-catalyzed incorporation of dansylcadaverine (A) and dansyl-PGGQQIV probe (B) into the wild type and mutated forms of FnbA. Incorporation of dansylcadaverine was performed in 20 mM Tris, pH 7.4, 150 mM NaCl, 5 mM DTT, 5 mM $CaCl_2$, while incorporation of dansyl-PGGQQIV was carried out in 20 mM Tris, pH 8.5, 15 mM NaCl, 5 mM DTT, 5 mM $CaCl_2$. Control reactions were also performed in the same buffers containing 2 mM EDTA. Aliquots were removed at the indicated time points, mixed with SDS, heated, and analyzed by SDS-PAGE on 4-20 gradient gels. Aliquots removed from control reactions at 60 (A) and 120 min (B) are labeled with asterisks. After electrophoresis, the gels were photographed under ultraviolet light (A and B, bottom) and then stained with Coomassie Brilliant Blue (A and B, top). The outer lanes in the gels contain molecular mass standards as indicated.

Figure 9:
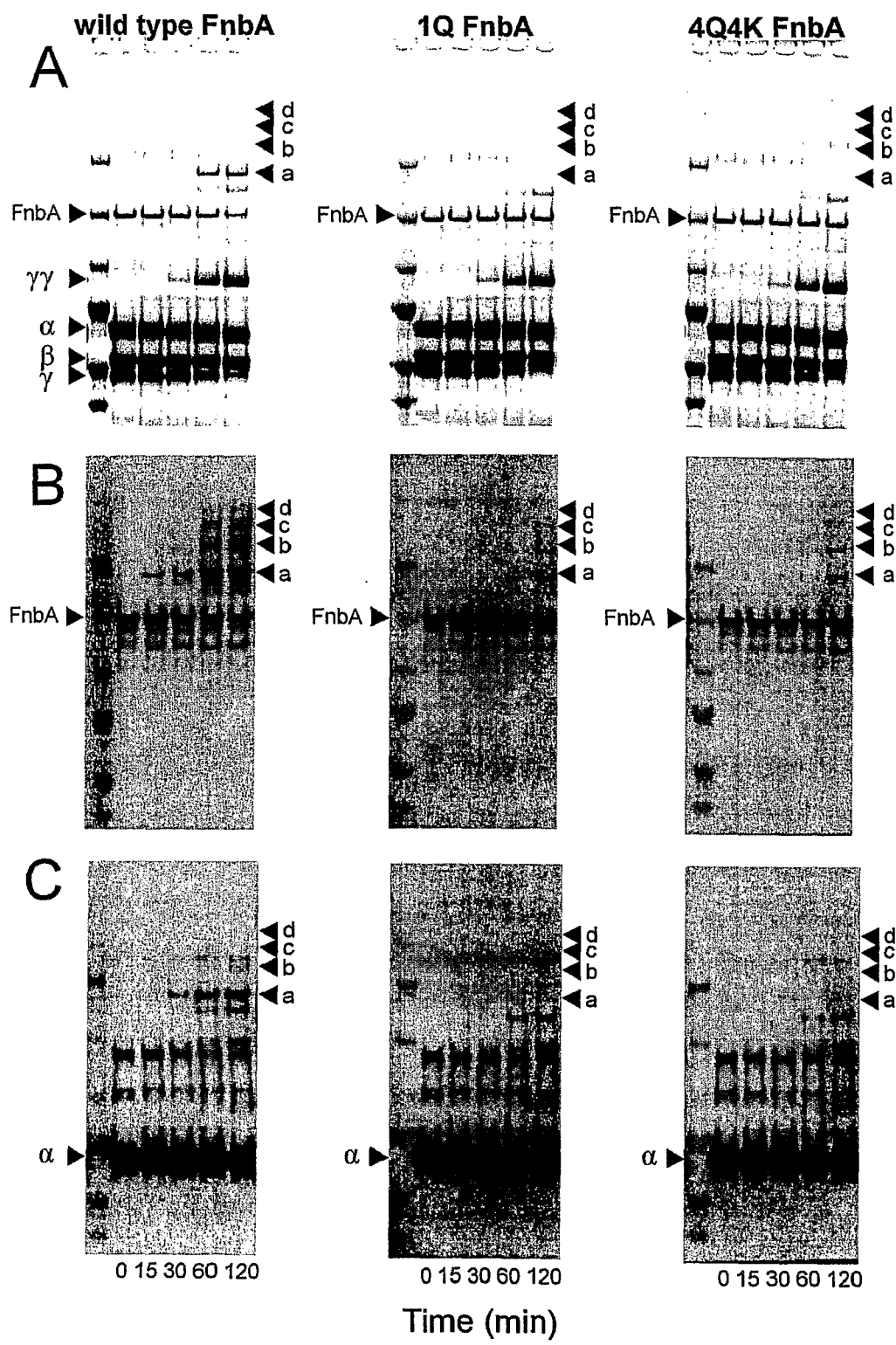

FIG. 9 depicts the Factor XIIIa-catalyzed cross-linking of the wild-type and mutated forms of FnbA to fibrin. At indicated time points, reactions were terminated and analyzed by SDS-PAGE on a 3-8% gradient gel under reducing conditions. After electrophoresis the gels were either stained with Coomassie Brilliant Blue (A), or subjected to transfer to nitrocellulose membranes followed by immunostaining with anti-FnbA (B) and anti-fibrinogen α chain (C) antibodies. Arrows show the positions of FnbA and α, β, γ chains of fibrin, and cross-linked γγ chains of fibrin. The major high mobility product of cross-linking between FnbA and fibrin α chain is designated as a, while low mobility products of cross-linking are depicted as b, c, and d. The left-hand lane in each panel contains molecular mass standards having, from top to bottom, the following Mr values: 250, 150, 100, 75, 50, and 37 kDa.

Figure 10:
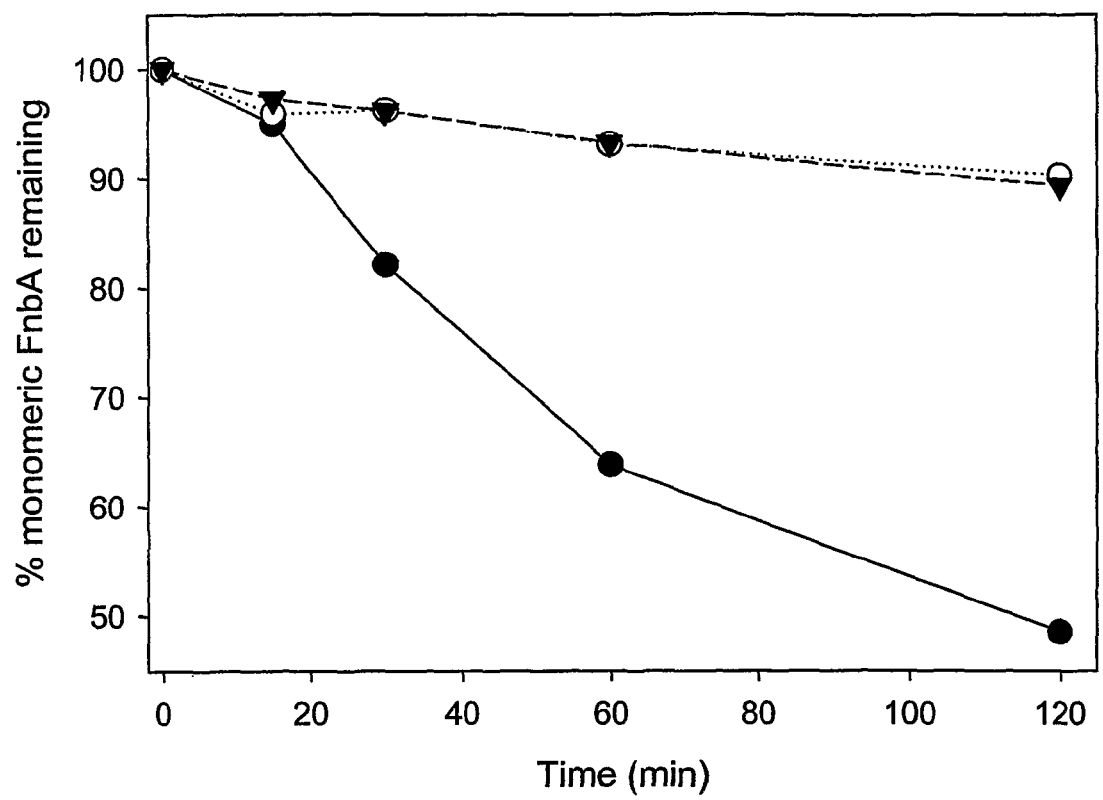

FIG. 10 depicts the rate of XIIIa-catalyzed cross-linking of the wild-type and mutated forms of FnbA to the fibrin α chain. The amount of remaining monomeric (uncross-linked) wild type FnbA (filled circles), 1Q FnbA (empty circles), and 4Q4K FnbA (filled triangles) was assayed as described in Materials and Methods and plotted as a function of time.

Figure 11:
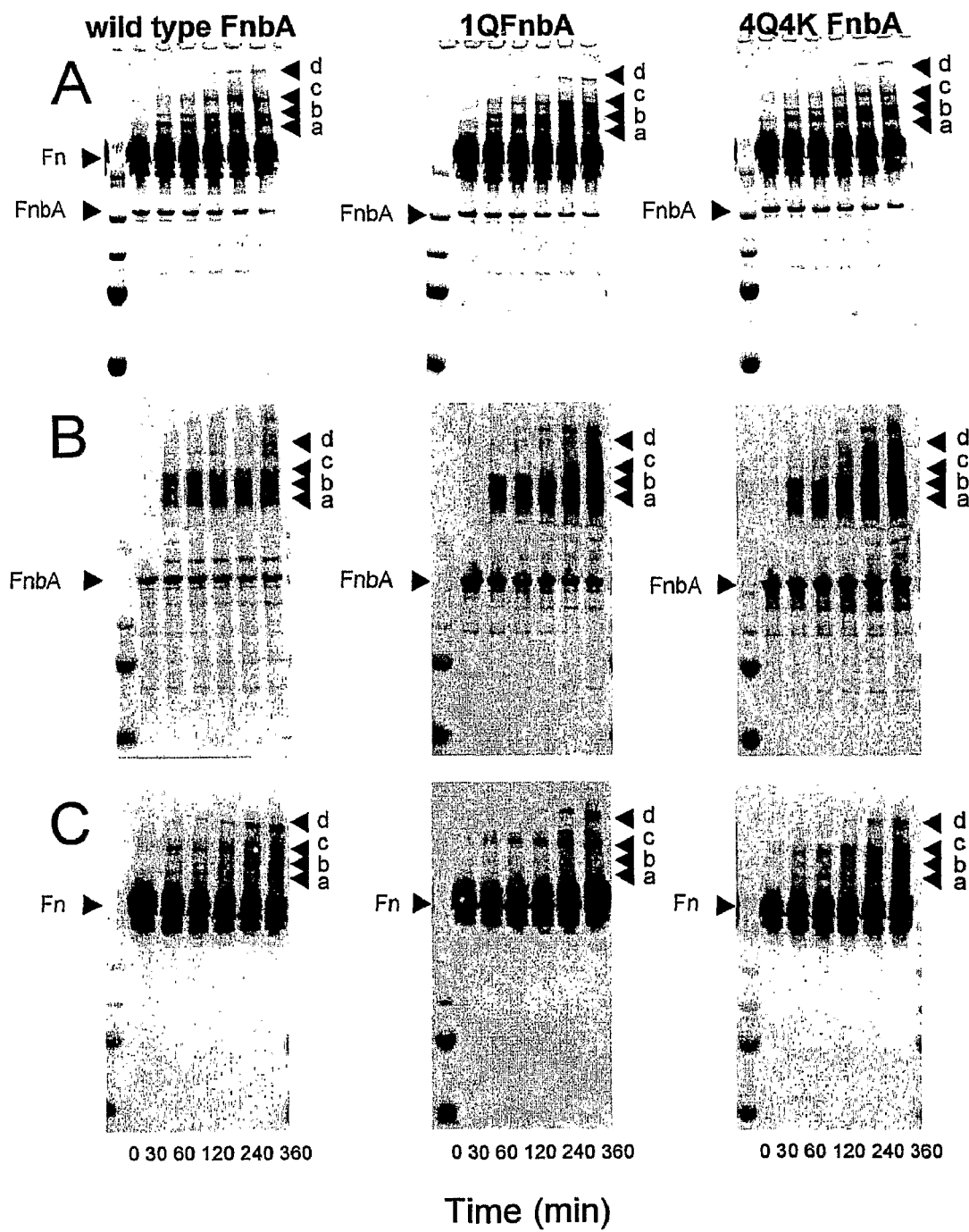

FIG. 11 depicts Factor XIIIa-catalyzed cross-linking of the wild-type and mutated forms of FnbA to fibronectin. At indicated time points, reactions were terminated and analyzed by SDS-PAGE on a 4-20% gradient gel under reducing conditions. After electrophoresis the gels were either stained with Coomassie Brilliant Blue (A), or subjected to transfer to nitrocellulose membranes followed by immunostaining with anti-FnbA (B) and anti-fibronectin (C) antibodies. Arrows show the positions of FnbA and fibronectin. The products of cross-linking between FnbA and fibronectin are depicted as a, b, c, and d. The left-hand lane in each panel contains molecular mass standards having, from top to bottom, the following Mr values: 250, 150, 100, 75, and 50 kDa.

Figure 12:
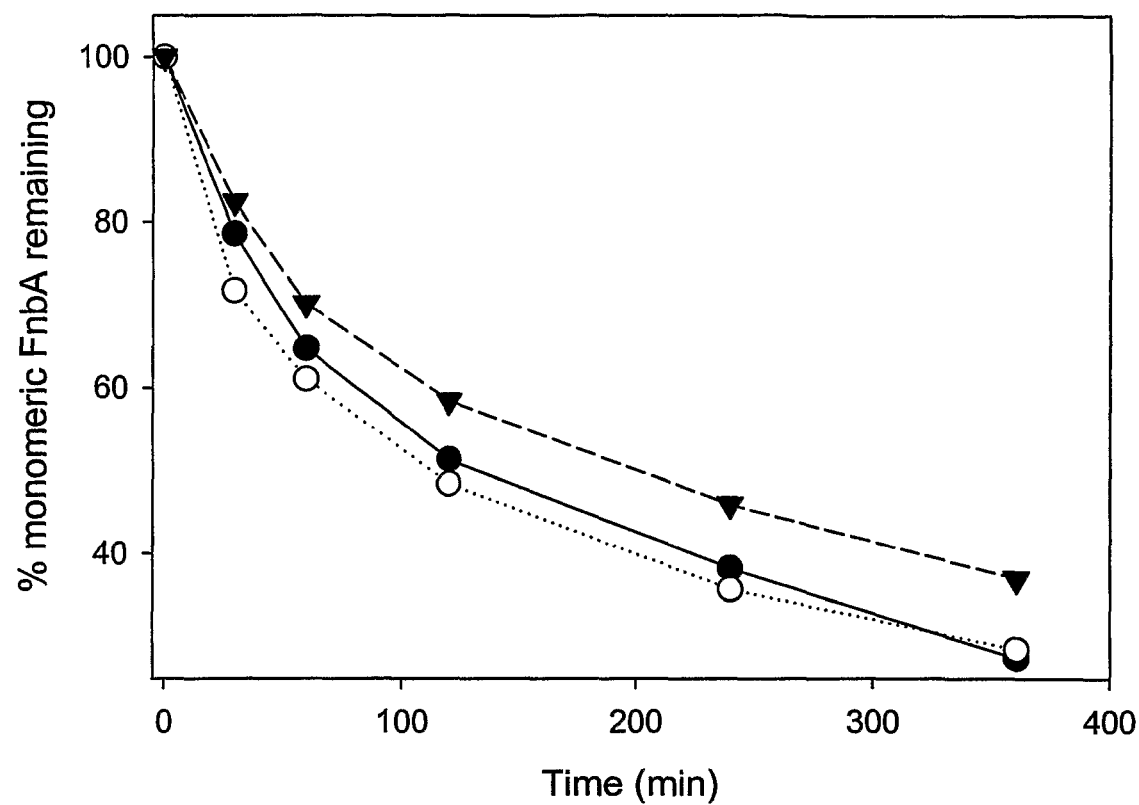

FIG. 12 depicts the rate of XIIIa-catalyzed cross-linking of the wild-type and mutated forms of FnbA to fibronectin. The amount of remaining monomeric (uncross-linked) wild-type FnbA (filled circles), 1Q FnbA (empty circles), and 4Q4K FnbA (filled triangles) was assayed as described in Materials and Methods and plotted as a function of time.

Figure 13:
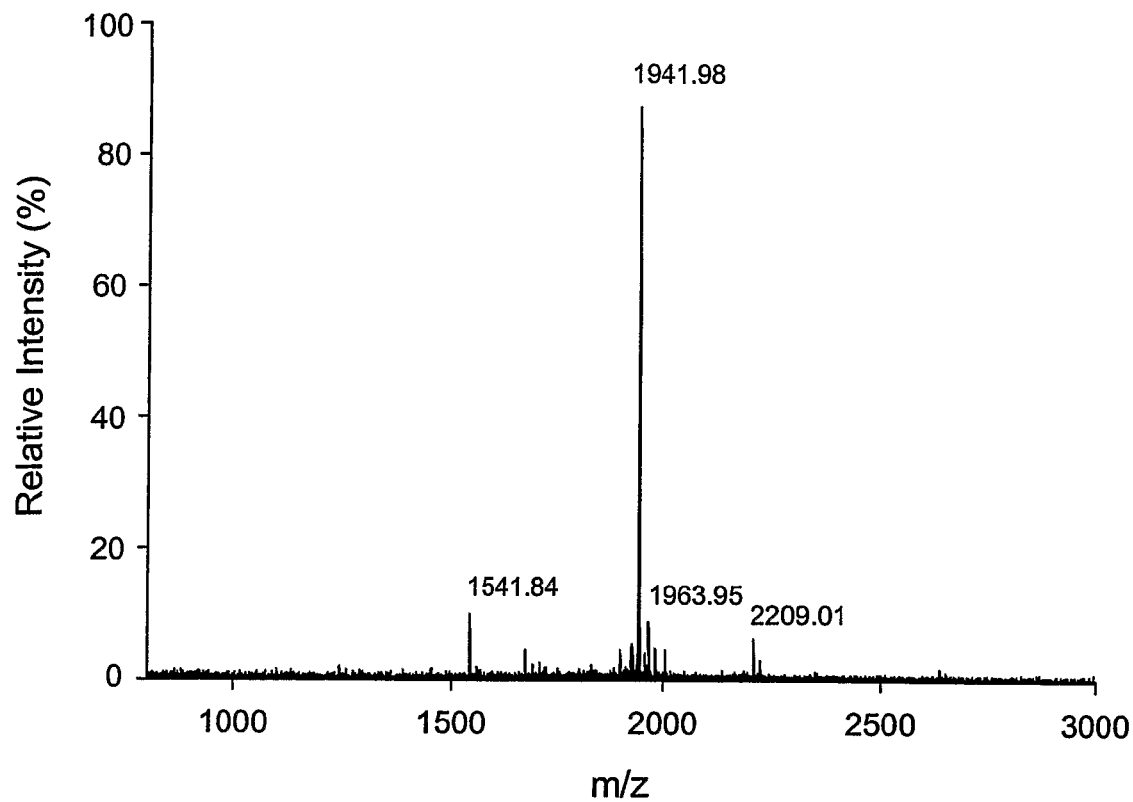

FIG. 13 shows the MALDI-TOF mass spectrum of isolated dansyl-PGGQIV-labeled peptide (fluorescent peak 3 (Anderson et al. 2004)) from the Glu-C protease digest of Factor XIIIa-modified wild-type FnbA.

FIG. 14 shows an alignment of the amino acid sequences of the FnbA and FnbB species from various *S. aureus* strains. The region surrounding Factor XIIIa-reactive Lys702 is shown. The position of the identified reactive Lys residue at the top corresponds to that of the FnbA from *S. aureus* strain ATCC49525. Table BB depicts the position of the amino acids comprising the region surrounding Lys702 in the amino acid sequence of each *S. aureus* strain. The multiple sequence alignment was performed using the CLUSTAL W (1.81) program (Thompson et al. 1994).

TABLE BB

Position of the Amino Acids Surrounding Lys702 in Each *S. aureus* Strain

| SEQ ID | Lys702 |
|---|---|
| 1 | 697-707 |
| 2 | 728-738 |
| 3 | 728-738 |
| 4 | 733-743 |
| 5 | 741-751 |
| 6 | 732-742 |
| 7 | 732-742 |
| 8 | 743-753 |
| 9 | 679-689 |
| 10 | 679-689 |
| 11 | 675-685 |
| 12 | 675-685 |
| 13 | 668-678 |
| 14 | 668-678 |

DETAILED DESCRIPTION OF THE INVENTION

FnbA is covalently cross-linked to either fibronectin or fibrin by the transglutaminase action of Factor XIIIa, resulting in the formation of receptor-ligand homo- and heteropolymers(s). Coagulation Factor XIIIa or plasma transglutaminase (EC 2.3.2.13) belongs to the transamidase class of enzymes that catalyze the covalent cross-linking of specific protein substrates through the formation of intermolecular ε-(γ-glutamyl)lysine isopeptide bonds. Cross-linking occurs via an acyl transfer reaction in which the γ carbon/amide group of glutamine serves as the acyl-donor (amine-acceptor) and the ε-amino group of lysine serves as the acyl-acceptor (amine-donor) (Henschen and McDonagh 1986; Lorand 2001).

Factor XIII circulates in the blood as a non-active tetramer precursor, $A_2B_2$, that is composed of two catalytic A subunits and two regulatory B subunits. Following exposure to thrombin, Factor XIII zymogen undergoes a $Ca^{2+}$-dependent activation to Factor XIIIa (Factor XIII activated), which subsequently catalyzes the formation of covalent cross-links between γ chains and between α chains of a fibrin clot. This reaction represents the final event in the blood coagulation cascade and is essential for normal hemostasis. Factor XIIIa is also involved in the covalent incorporation of several different human proteins into fibrin clots by the same mechanism. See Table 1. Among them are fibronectin and $α_2$-antiplasmin whose cross-linking to the clot plays an important role in wound healing and fibrinolysis.

The protein-protein cross-linking reactions catalyzed by Factor XIIIa represent a two-stage process. First, proteins specifically associate with each other to form a reversible (non-covalent) complex, and second, they become covalently cross-linked by Factor XIIIa. In general, protein cross-linking catalyzed by Factor XIIIa produces a variety of fused homo- and heteropolymeric structures that play an important role in a number of physiological reactions (Lorand and Graham 2003). The recent finding, that *S. aureus* can utilize transglutaminase activity for adhesion to human extracellular matrix (ECM) molecules (Matsuka et al. 2003), indicates that protein cross-linking is involved in pathological reactions associated with bacterial infection.

Most *S. aureus* strains express one (FnbA) or two (FnbA and FnbB) fibronectin-binding proteins encoded by two different, but closely related, genes (Signas, Raucci et al. 1989; Jonsson, Signas et al. 1991). The $NH_2$-terminal region of the mature fibronectin-binding protein is formed by about a 500-residues long A region responsible for fibrinogen/fibrin binding activity of the receptor. The A region of FnbA contains the B1-B2 double copy of a 30-residues long repeat of unknown function which is missing in the FnbB version of the protein. The COOH-terminal region of fibronectin-binding protein contains five conserved, about 40-residues long, Du, D1, D2, D3 and D4 repeats that form the fibronectin-binding region of the receptor. The COOH-terminus of fibronectin-binding protein is covalently attached to the cell wall peptidoglycan by the transpeptidase activity of sortase (Schneewind, Fowler et al. 1995). The reversible binding of FnbA to fibronectin or fibrin is a prerequisite for efficient intermolecular covalent cross-linking. The association of FnbA with fibronectin or fibrin results in appropriately positioned donor lysine and acceptor glutamine residues that subsequently become cross-linked by Factor XIIIa. Factor XIIIa also catalyzes the formation of an isopeptide bond between the γ-carboxamide group of peptide-bound reactive glutamine residues and the amino groups of a variety of primary amines, including those of putrecine, spermidine, and cadaverine (Lorand, Rule et al. 1968; Lorand, Siefring et al. 1979). Incorporation of an alternative amine donor inhibits protein cross-linking and leads to an enzyme-directed, site-specific labeling of the participating glutamine residues in the acceptor protein (Lorand 2001).

Similarly, by utilizing peptides patterned after the N-terminal sequence of fibronectin or $\alpha_2$-antiplasmin, containing reactive glutamine residues, specific labeling of the participating lysine residues in the donor protein can be achieved (Parameswaran, Velasco et al. 1990; Lorand, Parameswaran et al. 1992; Sobel and Gawinowicz 1996). It has been recently determined that in the presence of Factor XIIIa, staphylococcal rFnbA could be modified by the amine donor synthetic probe dansylcadaverine and dansylated peptide patterned after the N-terminal sequence of fibronectin, which acts as an amine acceptor probe (Matsuka et al. 2003).

Figure 1:
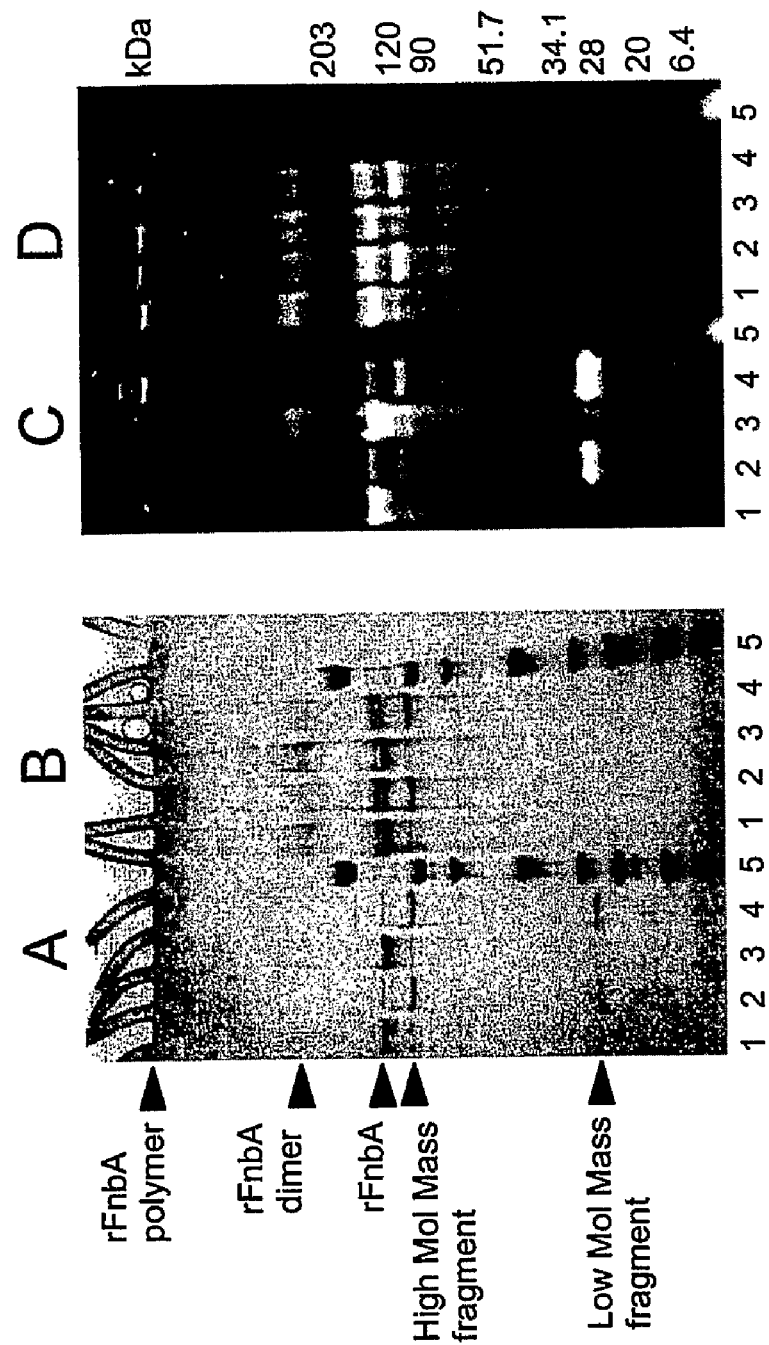
FIG. 1 depicts Factor XIIIa-catalyzed incorporation of dansylcadaverine (panels A and C) and dansyl-PGGQQIV (panels B and D) probes into rFnbA. SEQ ID NO:31 depicts the PGGQQIV amino acid sequence. Modification reactions were carried out for 4 and 18 hours. After the removal of unreacted probes modified for 4 hours (lane 1) and 18 hours (lane 3) rFnbA samples were analyzed by SDS-PAGE. Alternatively, the rFnbA samples modified over 4 and 18 hours were subjected to limited proteolysis by thrombin and then analyzed by SDS-PAGE (lanes 2 and 4). After electrophoresis the gels were photographed under ultraviolet light (panels C and D) and then stained with Coomassie Brilliant Blue (panels A and B). Arrows show positions of probe-modified rFnbA and its thrombin-generated fragments. Lane 5 in each panel contains molecular mass standards as indicated.
Figure 2:
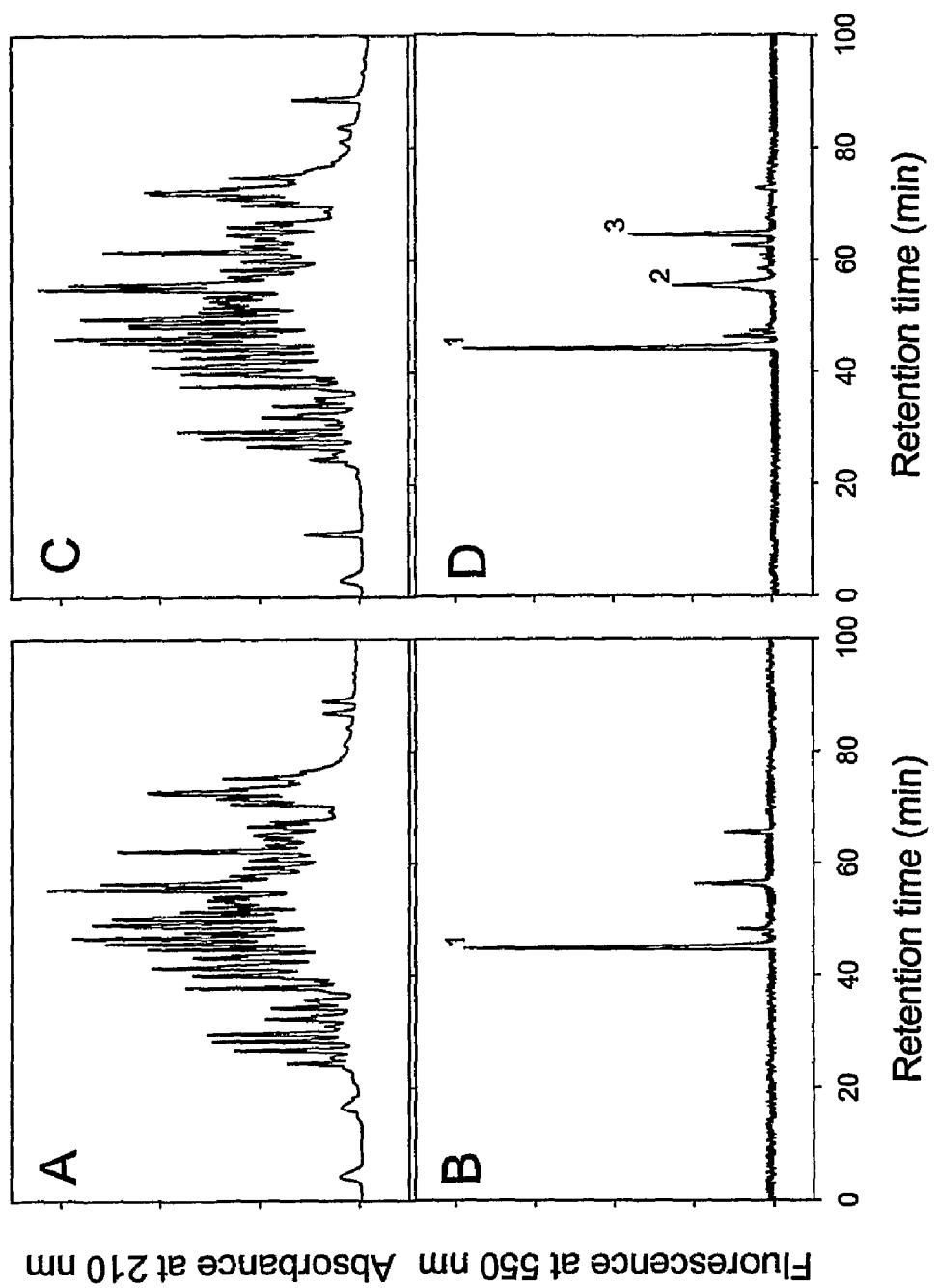
FIG. 2 depicts HPLC separation of dansylcadaverine-labeled peptides from the trypsin digest of Factor XIIIa-modified rFnbA. Factor XIIIa-catalyzed incorporation of dansylcadaverine into rFnbA was carried out for 4 (panels A and B) and 18 hours (panels C and D). The dansylcadaverine-labeled rFnbA preparations were digested by trypsin and the peptides were separated on an Aquapore RP-300 $C_8$ reverse phase column. The elution was monitored by absorbance at 210 nm as well as by fluorescence at 550 nm. Fluorescent peaks 1 (panels B and D), 2, and 3 (panel D) were collected, and after a second round of reverse phase chromatography subjected to $NH_2$-terminal sequence and mass-spectral analysis.

In the present invention there have been identified within the staphylococcal FnbA, reactive Gln and Lys residues that are targeted by human coagulation Factor XIIIa or tissue transglutaminase. This is the first report on the localization of Factor XIIIa-reactive amine acceptor and donor sites in a bacterial protein. Site-specific labeling of the Factor XIIIa-reactive glutamines was performed using the fluorescent lysine analog dansylcadaverine (Lorand, Rule et al. 1968; Lorand, Siefring et al. 1979). Factor XIIIa reacted with only 4 of the 48 Gln residues present in the rFnbA receptor. Residues Gln103, Gln105, Gln783, and Gln830 serve as amine acceptor sites in FnbA, when the latter is incubated with dansylcadaverine and coagulation Factor XIIIa. The rate and degree of dansylcadaverine modification of Gln103 was significantly higher than that of Gln105, Gln783, and Gln830 (FIGS. 2, B, D and FIGS. 3 B, D), suggesting that Gln103 acts as a major amine acceptor site. The reactive residues Gln103 and Gln105 are located within the $NH_2$-terminal A region of FnbA receptor (FIG. 5), while the Gln783 and Gln830 residues are situated in the COOH-terminal part of the molecule and belong to the D1 and D4 repeats, respectively. Identification of the Gln103 as a major amine acceptor site of the FnbA is consistent with the results of limited proteolysis experiments. The cleavage of dansylcadaverine-modified rFnbA by thrombin results in the release of a low molecular mass $NH_2$-terminal fragment, which exhibited a high intensity of fluorescence upon UV illumination, due to the presence of the major Gln103 acceptor site. The high molecular mass band corresponding to the COOH-terminal fragment and containing the minor Gln783 and Gln830 sites (FIG. 5) produced a low emission signal (FIGS. 1 A and C). Thus, limited proteolysis and SDS-PAGE data obtained for the dansylcadaverine-modified rFnbA provided another line of evidence suggesting various degrees of reactivity of identified acceptor sites. Upon SDS-PAGE analysis the thrombin-generated rFnbA fragments and the parent rFnbA exhibited lower than expected electrophoretic mobility. Most likely this is caused by a high content of charged residues in FnbA, which are known to decrease the capability of SDS-binding and, therefore, decrease electrophoretic mobility. When the rFnbA sample was subjected to mass-spectral analysis, its experimentally determined molecular mass value was essentially indistinguishable from the calculated value.

The dansyl-PGGQQIV peptide probe patterned on the $NH_2$-terminal sequence of fibronectin containing reactive glutamine residues, was utilized for the labeling of Factor XIIIa-reactive lysine residues (Parameswaran, Velasco et al. 1990; Lorand, Parameswaran et al. 1992). The labeling procedure revealed that 4 of the 56 potential lysine donor residues within rFnbA incorporated the peptide probe. These residues are Lys157, Lys503, Lys620, and Lys762. The identified Factor XIIIa-reactive lysine sites are distributed between the fibrin(ogen)-binding region A and the fibronectin-binding D repeats. Lys157 is located within the $NH_2$-terminal part of the A region, while Lys503 is located in its COOH-terminal segment adjacent to the B1B2 repeats. The fibronectin-binding Du and D2 repeats contain the Factor XIIIa-reactive Lys620 and Lys762 sites, respectively (FIG. 5). Interestingly, despite the $NH_2$-terminal location of the reactive Lys157, thrombin cleavage of the dansyl-PGGQ-QIV-decorated rFnbA did not produce a fluorescent low molecular mass fragment (FIG. 1 D, lanes 2 and 4). The low molecular mass fragment was not detectable upon staining of the gel with Coomassie Brilliant Blue (FIG. 1B, lanes 2 and 4). These observations indicate that the modification of Lys157 with the dansyl-PGGQQIV probe might induce higher susceptibility of the $NH_2$-terminal region of FnbA to thrombin attack resulting in the generation of small peptides that are not detectable on SDS-PAGE.

Overall, all of the identified reactive Gln acceptor and Lys donor residues tend to cluster in the $NH_2$- and COOH-terminal areas of FnbA that form the fibrin(ogen)- and fibronectin-binding sites. The existence of additional Gln acceptor and Lys donor residues within the staphylococcal FnbA receptor, however, cannot be excluded since the fluorescent tracer containing peptides corresponding to peak 2 (FIG. 2 D), peaks 2, 3, 5 (FIG. 3 D) and peak 3 (FIG. 4D) was not positively identified. Nevertheless, site-specific labeling allowed the localization of the exact positions of reactive Gln and Lys residues participating in Factor XIIIa-catalyzed cross-linking reactions of FnbA with fibronectin, fibrin, and, possibly, other human host proteins. Upon sequencing, several peaks produced more than one residue in each cycle, indicating the heterogeneity of HPLC fractions. Heterogeneity of these samples was also evident from the results of mass-spectral analysis. Comparison of the residues in each cycle against the known sequence of FnbA and the available map with the predicted trypsin- or Glu-C proteinase-generated cleavage sites allowed most individual sequences to be identified. The results of the $NH_2$-terminal sequence analysis in this study always correlated with the mass-spectral data, which showed the presence of signals corresponding to the predicted probe-modified peptides.

Up to now, only a little more than a dozen protein substrates have been identified for coagulation Factor XIIIa. Among the known glutamine-containing substrates for Factor XIIIa, there exists little sequence homology and reactivity is difficult if not impossible to predict. The identified reactive glutamines are usually located in the solvent-exposed surface regions or flexible extensions (Cottrell, Strong et al. 1979; McDonagh, McDonagh et al. 1981; Matsuka, Medved et al. 1996). Without being bound by theory, both the primary structure and the conformation of a protein appear to determine whether a glutamine residue can be reactive. These observations are consistent with the data shown herein for the staphylococcal FnbA receptor.

The reactive Gln783 and Gln830 acceptor sites are situated in the D2 and D4 fibronectin-binding repeats, which, according to several reports, do not have a compact structure and exist in a rather unfolded state (House-Pompeo, Xu et al. 1996; Penkett, Redfield et al. 1997; Penkett, Redfield et al. 1998). The reactive Gln103 and Gln105 sites are located in the $NH_2$-terminal region of FnbA that appears to be sensitive to proteolysis and, therefore, again may indicate lack of an ordered structure. The selectivity of Factor XIIIa towards the amine donor lysine residues in proteins is not sufficiently understood either. Despite the common notion that Factor XIIIa is less selective toward lysine residues than to glutamine residues, only a restricted number of amine donor sites can participate in a particular protein-protein cross-linking reaction and undergo modifications with a peptide probe. It was shown that Factor XIIIa exhibits broad yet clearly differentiated tolerance with respect to the residue preceding the amine donor lysine in protein substrates. Analysis of protein substrates for Factor XIIIa or tissue transglutaminase revealed that the residues directly preceding the amine donor site include uncharged and basic polar residues, as well as the small aliphatic ones (Grootjans, Groenen et al. 1995). The data disclosed herein for the staphylococcal FnbA receptor further supports these observations. Among the four identified Factor XIIIa-reactive lysines, Val precedes Lys157, Ala precedes Lys503, and Thr precedes Lys620. The only exception is Glu, which precedes Lys762 (FIG. 5).

In order to investigate whether the identified Factor XIIIa-reactive sites are conserved in other fibronectin-binding proteins from different S. aureus strains, their amino acid sequences were analyzed using a multiple sequence alignment. The amino acid sequence of FnbA of S. aureus strain ATCC49525 (SEQ ID NO:1) was compared with the FnbA and FnbB sequences of strains 8325-4 (SEQ ID NO:7 and SEQ ID NO:14) (Signas, Rauci et al. 1989; Jonsson, Signas et al. 1991), MW2 (SEQ ID NO:4 and SEQ ID NO:11) (Baba, Takeuchi et al. 2002), EMRSA-16 (SEQ ID NO:8), MSSA-476 (SEQ ID NO:5 and SEQ ID NO:12), COL (SEQ ID NO:6 and SEQ ID NO:13), Mu50 (SEQ ID NO:2 and SEQ ID NO:9), and N315 (SEQ ID NO:3 and SEQ ID NO:10) (Kuroda, Ohta, et al. 2001). The amino acid sequences of FnbA and FnbB of strains EMRSA-16 and MSSA-476 were obtained from the Wellcome Trust Sanger Institute. The S. aureus COL sequence was obtained from the Institute for Genomic Research. Multiple sequence alignment was performed using the CLUSTAL W (1.81) program (Thompson, Higgins, et al. 1994).

FIG. 6 shows the amino acid sequence alignment of the regions surrounding the identified reactive Gln and Lys residues in the FnbA of S. aureus strain ATCC49525. A multiple alignment revealed that the reactive Gln103, Gln105, Gln830, and Lys620 residues are conserved in all analyzed FnbA sequences. In the FnbA of strains MW2, MSSA-476, COL, 8325-4, and EMRSA-16 the reactive Lys157 is replaced with a Thr residue. In strains COL and 8325-4, the reactive Lys503 is substituted to an Asn residue. The segment of polypeptide chain containing reactive Lys762 is missing in the FnbA sequence of EMRSA-16 strain and the reactive Gln783 is substituted to His in COL and 8325-4 strains (FIG. 6). This observation indicates that the reactivity of FnbA of different S. aureus strains towards the transglutaminase action of Factor XIIIa can vary.

Also, it is apparent that the Factor XIIIa-reactive acceptor and donor sites are less preserved within the FnbB family of receptors. None of the analyzed FnbB sequences possess the reactive Gln103, Lys157, and Lys503, while Lys762 is missing in Mu50 and N315 strains. The reactive Gln105 and Gln783 are not preserved in the FnbB sequence of strains MW2, MSSA-476, COL, and 8325-4. Among all of the identified Factor XIIIa-reactive sites, only the Lys620 and Gln830 residues are highly conserved and present in all analyzed FnbA and FnbB sequences (FIG. 6).

Figure 4:
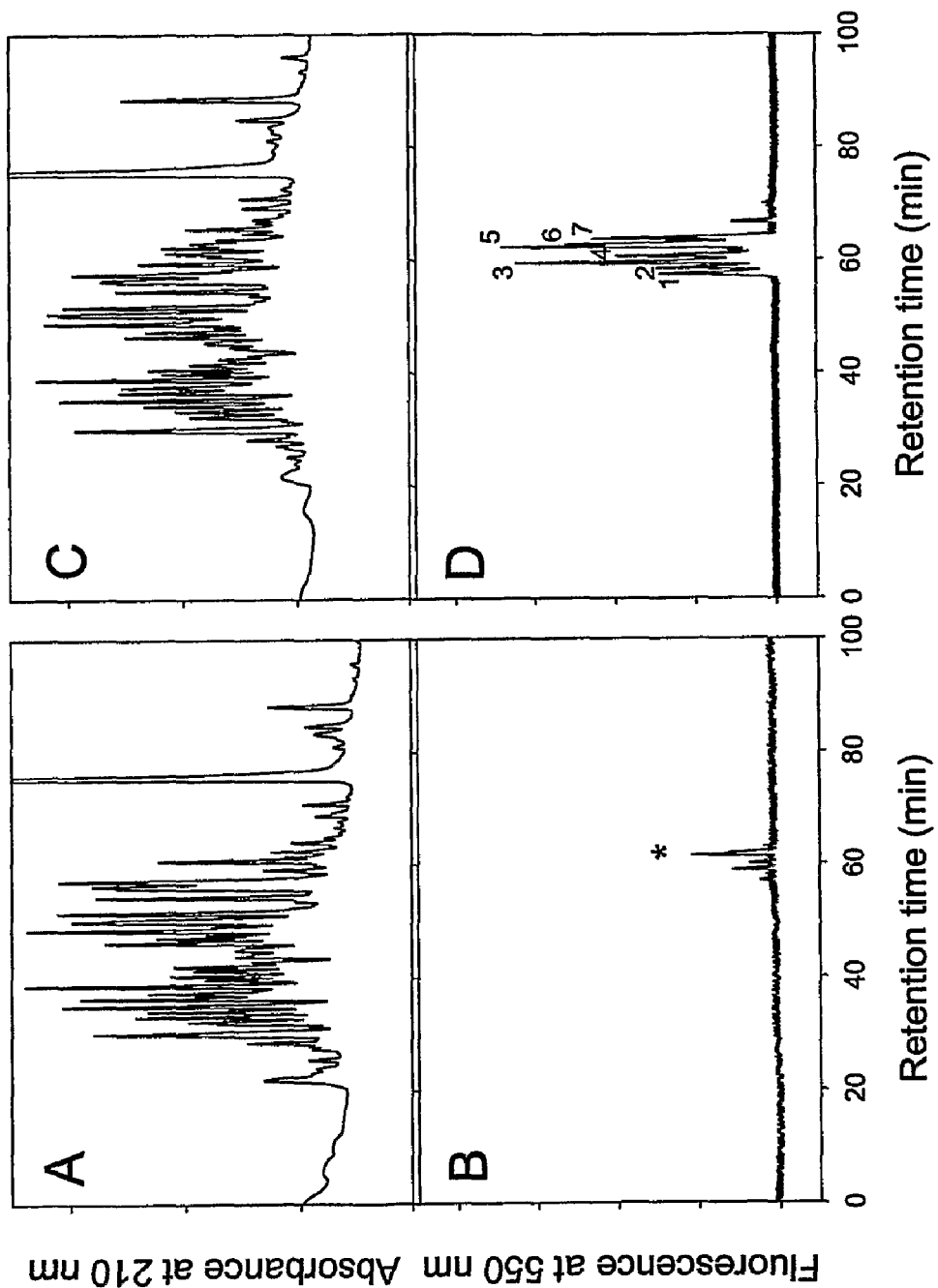
FIG. 4 depicts HPLC separation of dansyl-PGGQQIV-labeled peptides from the Glu-C protease digest of Factor XIIIa-modified rFnbA. Factor XIIIa-catalyzed incorporation of dansyl-PGGQQIV into rFnbA was carried out for 4 (panels A and B) and 18 hours (panels C and D). The dansyl-PGGQ-QIV-labeled rFnbA preparations were digested by Glu-C protease and the peptides were separated on an Aquapore RP-300 $C_8$ reverse phase column. The elution was monitored by absorbance at 210 nm as well as by fluorescence at 550 nm. The fluorescent peak depicted by an asterisk (panel B) and peaks 1, 2, 3, 4, 5, 6 and 7 (panel D) were collected, and after the second round of reverse phase chromatography, subjected to $NH_2$-terminal sequence and mass-spectral analysis.

Interestingly, upon treatment of FnbA with Factor XIIIa, the conserved reactive Lys620 residue consistently exhibited the highest reactivity towards the dansyl-PGGQQIV probe (FIG. 4 B peak* and D peak 5, Table 3). This further indicates the physiological importance of the Lys donor site at position 620. The fact that the major Gln103 acceptor site along with the Lys157 and Lys503 donor sites are absent in all evaluated FnbB sequences suggests that the B form of fibronectin-binding protein plays a less prominent role in Factor XIIIa-catalyzed cross-linking reactions. These differences also indicate that the A and B forms of fibronectin-binding protein exhibit different selectivity toward their human host protein cross-linking partners.

With the exception of the staphylococcal FnbA receptor, all currently known Factor XIIIa protein substrates are involved in blood coagulation, fibrinolysis, extracellular matrix assembly, and wound healing reactions. The inventors finding that S. aureus FnbA serves as a bifunctional substrate for Factor XIIIa and undergoes cross-linking to fibronectin or fibrin (Matsuka et al. 2003) suggests that coagulation Factor XIIIa also plays an important role in molecular pathogenesis. The ability of pathogenic S. aureus to utilize the transglutaminase activity of Factor XIIIa for covalent attachment to human host molecules explains the extremely high efficiency of bacterial colonization upon tissue injury. Following injury, the formation of a blood clot serves both to restore vascular integrity and to provide a provisional matrix for the initiation of wound repair (Mosesson 1992). The clot's major protein components, fibrin and plasma fibronectin are essential for these functions. Both fibrin and fibronectin also serve as ligands for the surface-associated FnbA receptor of S. aureus, and therefore, responsible for the binding of the bacteria to the wound site. As the clot matures, coagulation Factor XIIIa initiates catalysis of intermolecular cross-linking between fibrin molecules and between fibrin and fibronectin. Covalent cross-linking between fibrin molecules increases the structural stability of the clot (Henschen and McDonagh 1986), while the cross-linking of fibronectin to fibrin is important for cell adhesion and migration events required for the wound healing process (Grinnel, Feld et al. 1980; Knox, Crooks et al. 1986; Corbett, Lee et al. 1997). The staphylococcal FnbA receptor that is reversibly associated with fibrin or fibronectin at this stage can be covalently cross-linked to its ligands by Factor XIIIa. The covalent incorporation of FnbA to fibrin or fibronectin increases the probability of staphylococcal colonization and establishment of infection. It also competes with fibrin-fibrin and fibrin-fibronectin cross-linking reactions (Matsuka, Medved et al. 1994; Matsuka, Migliorini et al. 1997) (Matsuka et al. 2003), and therefore, can affect the structural integrity of the clot and inhibit the wound-healing reaction. Such implications of Factor XIIIa-catalyzed cross-linking of staphylococcal FnbA to human extracellular matrix proteins most likely served as a driving force for the molecular evolution of the FnbA receptor, resulting eventually in its acquiring a new and useful property. The evolved reactivity of FnbA towards Factor XIIIa has provided a significant advantage in the colonization of the host and subsequently has had a positive impact on the survival of S. aureus.

In addition to identifying the reactive amino acid residues (Gln and Lys) within wild-type staphylococcal FnbA that are directly involved in the Factor XIIIa-catalyzed covalent cross-linking reaction described herein, the present invention relates to the synthesis of Fnb-derived proteins that are less capable than wild-type Fnb of covalently cross-linking with fibronectin and fibrin upon subsequent S. aureus infection. Specifically, the work described herein is directed to compositions and methods of preparation of proteins and/or polypeptides comprising altered fibronectin-binding proteins or polypeptides that can be used as immunogens in immunogenic composition formulations, including multivalent immunogenic compositions, and which can be used for active immunization. The strategy involves alteration of one or more amino acids in a Fnb sequence, resulting in a protein or polypeptide derived from Fnb that is immunogenic without inducing enhanced binding of wild-type Fnb to fibronectin and fibrin upon subsequent S. aureus infection. Mutations of two, three or more of the amino acid residues identified herein are within the scope of the invention.

The wild type (native) nucleotide and amino acid sequences of Fnb are known in the art (U.S. Pat. Nos. 5,320,951; 5,571,514; 5,175,096; 5,652,217). As used herein, "alteration" and its derivatives is intended to mean an amino acid sequence which is different from the wild-type sequence, as well as a nucleotide sequence which encodes an amino acid sequence which is different from the wild-type amino acid sequence. Alteration includes insertion, deletion and/or substitution of one or more nucleotides or amino acids.

For example, the alteration can be the insertion or deletion of a single nucleotide, or of more than one nucleotide, resulting in a frame shift mutation; the change of at least one nucleotide, resulting in a change in one or more encoded amino acids; the change of at least one nucleotide, resulting in the generation of a premature stop codon; the deletion of several nucleotides, resulting in a deletion of one or more amino acids encoded by the nucleotides; the insertion of one or several nucleotides, resulting in an interruption of the coding sequence of the gene; duplication of all or a part of the gene; transposition of all or a part of the gene; or rearrangement of all or a part of the gene. More than one such mutation may be present in a single gene. Such sequence changes cause an alteration in the Fnb encoded by the gene. For example, if the alteration is a frame shift mutation, the frame shift can result in a change in the encoded amino acids, and/or can result in the generation of a premature stop codon, causing generation of a truncated protein.

For example, the alteration(s) can preferably preserve the three-dimensional configuration of the native Fnb. Moreover, amino acids that are essential for the function of Fnb, particularly for immunogenicity, can be identified by methods known in the art. Particularly useful methods include identification of conserved amino acids, site-directed mutagenesis and alanine-scanning mutagenesis (for example, Cunningham and Wells 1989), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (Science 247:1306-1310 (1990)).

For example, the alteration can take the form of conservative (e.g., glycine for alanine; valine for isoleucine; histidine for lysine; asparagine for glutamine) site-directed mutation of the glutamine and lysine residues (FIG. 6) which retains attributes of the region of the FnbA involved in protective immune responses but deletes or modifies epitopes involved in the stimulation of S. aureus infections (i.e., a biological equivalent). The alteration can also take the form of non-conservative mutations (e.g., lysine for threonine; alanine for lysine; alanine for glutamine) wherein the deleterious stimulation of S. aureus infections is reduced or abolished. The alteration can also take the form of complete deletion of any of the glutamine or lysine residues identified herein, with continued use of the remaining Fnb derived moiety. Deletions can be replaced by linker regions that retain the spatiality of the remaining Fnb or polypeptide in order for optimal translation and/or immunogenicity. Alterations can be made using any standard mutagen or mutagenic process, such as site-directed mutation involving phages or use of polymerase chain reaction (PCR) technology involving synthetic oligonucleotides.

Accordingly, the invention pertains to an isolated nucleotide sequence encoding an altered Fnb of S. aureus, or portion thereof, wherein the altered Fnb or portion thereof retains immunogenicity. As used herein, the term "altered Fnb" is intended to mean a Fnb (or portion thereof) of S. aureus which retains immunogenicity and which, when incorporated into an immunogenic composition and administered to a vertebrate, does not enhance binding to fibronectin or fibrin upon subsequent infection with S. aureus. In a particular embodiment, the altered Fnb comprises a mutation of at least one amino acid selected from the group consisting of residues corresponding to Gln103, Gln105, Lys157, Lys503, Lys620, Lys762, Gln783 and Gln830 of the FnbA of S. aureus strain ATCC49525. In one embodiment, these amino acids are mutated to alanine.

Although the invention is specifically described with relation to the amino acids corresponding to Gln103, Gln105, Lys157, Lys503, Lys620, Lys762, Gln783 and Gln830 of the FnbA of S. aureus strain ATCC49525, it is intended that the methodologies described herein used to identify these residues can be applied to additional residues of the wild-type Fnb to identify additional residues for alteration.

As appropriate, nucleic acid molecules of the present invention can be RNA, for example, mRNA, or DNA, such as cDNA and genomic DNA. DNA molecules can be double-stranded or single-stranded; single stranded RNA or DNA can be the coding, or sense, strand or the non-coding, or antisense, strand. In one embodiment, the nucleic acid molecule comprises at least about 14 nucleotides; in another embodiment, at least about 50 nucleotides; and in even yet another embodiment, at least about 200 nucleotides. The nucleotide sequence can be only that which encodes at least a fragment of the amino acid sequence of the altered Fnb; alternatively, the nucleotide sequence can include at least a fragment of the altered Fnb amino acid coding sequence along with additional non-coding sequences such as introns and non-coding 3' and 5' sequences (including regulatory sequences, for example). Additionally, the nucleotide sequence can be fused to a marker sequence, for example, a sequence that encodes a polypeptide to assist in isolation or purification of the polypeptide.

The term "nucleotide sequence" can include a nucleotide sequence that is synthesized chemically or by recombinant means. Thus, recombinant DNA contained in a vector is included in the invention. Also, nucleotide sequences include recombinant DNA molecules in heterologous host cells, as well as partially or substantially purified DNA molecules in solution. In vivo and in vitro RNA transcripts of the DNA molecules of the present invention are also encompassed by nucleotide sequences of the invention. Such nucleotide sequences are useful, e.g., in the manufacture of the encoded altered Fnb.

The invention also encompasses variations of the nucleotide sequences of the invention, such as those encoding portions, analogues or derivatives of the altered Fnb, provided the portion, analogue or derivative comprises the altered Fnb. Such variations can be naturally occurring variations in the unaltered portion of the nucleotide sequence, such as in the case of allelic variation, or non-naturally-occurring, such as those induced by various mutagens and mutagenic processes. Intended variations include, but are not limited to, addition, deletion and substitution of one or more nucleotides that can result in conservative or non-conservative amino acid changes, including additions and deletions.

The invention described herein also relates to fragments of the nucleic acid molecules described above. The term "fragment" is intended to encompass a portion of a nucleotide sequence described herein which is from at least about 14 contiguous nucleotides to at least about 50 contiguous nucleotides or longer in length, providing that such fragments encode an altered Fnb polypeptide; such fragments are useful as primers. Certain primers and probes selectively hybridize to the nucleic acid molecule encoding the altered Fnb described herein. For example, fragments that encode antigenic portions of the altered Fnb described herein are useful.

The invention also pertains to nucleotide sequences that hybridize under medium and high stringency hybridization conditions (e.g., for selective hybridization) to a nucleotide sequence described herein. Appropriate stringency conditions are known to those skilled in the art or can be found in standard texts such as Current Protocols in Molecular Biology, John Wiley & Sons, N.Y. (1989), 6.3.1-6.3.6.

Accordingly, the invention pertains to nucleotide sequences which have a substantial identity with the altered nucleotide sequences described herein, such as, for example, at least 90% identity or at least 95% identify with these sequences. Particular nucleotide sequences encode polypeptides having substantially similar immunogenic activity as the altered Fnb described herein.

This invention also pertains to an altered Fnb or polypeptide thereof of S. aureus. The altered Fnb or polypeptide is a Fnb (or portion thereof) of S. aureus which retains immunogenicity and which, when incorporated into an immunogenic composition and administered to a vertebrate, is less capable than wild-type Fnb of cross-linking with fibronectin and fibrin upon subsequent infection with S. aureus. In a particular embodiment, the altered Fnb comprises a mutation of at least one amino acid selected from the group consisting of residues corresponding to Gln103, Gln105, Lys157, Lys503, Lys620, Lys762, Gln783 and Gln830 of the FnbA of S. aureus strain ATCC49525. The altered Fnb of the invention is substantially purified (e.g., purified to homogeneity), and is substantially free of other proteins.

The invention also provides expression vectors, e.g., nucleic acid constructs such as plasmids and cosmids, containing a nucleic acid sequence encoding an altered Fnb or polypeptide, operably linked to at least one regulatory sequence. Many such vectors are commercially available, and the skilled artisan can readily prepare other suitable vectors. "Operably linked" means that the nucleotide sequence is linked to a regulatory sequence in a manner which allows expression of the nucleic acid sequence; this term is intended to include both direct physical linkage and linkage by means of a linker or intervening sequence. Regulatory sequences are art-recognized and are selected to produce a polypeptide that is an altered Fnb or polypeptide. Accordingly, the term "regulatory sequence" includes promoters, enhancers, and other expression control elements which are described in Goeddel, Gene Expression Technology: Methods in Enzymology 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed.

For instance, the altered Fnb's and polypeptides of the present invention can be produced by ligating the nucleic acid molecule, or a portion thereof, into a vector suitable for expression in either prokaryotic cells, eukaryotic cells or both (see, for example, Broach, et al. 1983, Sambrook et al. 1989).

Prokaryotic and eukaryotic host cells transfected by the described vectors are also provided by this invention. For instance, cells which can be transformed, transfected or infected with the expression vectors of the present invention include, but are not limited to, bacterial cells such as E. coli (e.g., E. coli K12 strains), Streptomyces, Pseudomonas, Serratia marcescens and Salmonella typhimurium, insect cells (baculovirus), including Drosophila, Sf9 and Sf21 cells, fungal cells, such as yeast cells, plant cells and mammalian cells, such as thymocytes, Chinese hamster ovary (CHO) cells, HEp-2 cells, Vero cells and COS cells.

Thus, a nucleotide sequence encoding the altered Fnb described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well known proteins. Viral vectors may also be used, including, but not limited to, adenoviruses, adeno-associated viruses, herpes simplex virus, retroviruses, lentiviruses, poxviruses, including vaccinia virus, alphaviruses, such as sindbis virus, semliki forest virus, and Venezuelan equine encephalitis virus, and non-segmented, negative-stranded RNA viruses, such as measles virus, mumps virus, and vesicular stomatitis virus. Accordingly, the invention pertains to the production of altered Fnb by recombinant technology.

In addition to the foregoing host cell systems in which the altered Fnb of this invention is produced in vitro, a variety of systems are appropriate for expression and delivery of such altered Fnb in vivo. These systems utilize attenuated pathogens such as bacteria or viruses as delivery agents. These live attenuated pathogens have inserted within them as a heterologous nucleic acid segment the nucleic acid sequence encoding the desired altered Fnb of this invention. Using these systems, the desired altered Fnb is expressed by a live, attenuated bacterium or virus within the body of a vertebrate.

The proteins of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also pertains to immunogenic compositions comprising the altered Fnb described herein. For instance, an altered Fnb of the present invention can be formulated with a physiologically acceptable vehicle to prepare an immunogenic composition. The particular physiological vehicle may include, but is not limited to, water, buffered saline, polyols (e.g., glycerol, propylene glycol, liquid polyethylene glycol) and dextrose solutions. The optimum concentration of the active ingredient(s) in the chosen vehicle can be determined empirically, according to well-known procedures, and will depend on the ultimate pharmaceutical formulation desired.

The altered Fnb can be used as an antigen to elicit an immune response to the antigen in a vertebrate, such as a mammalian host.

The method of the present invention comprises administering to the vertebrate an immunologically effective dose of an immunogenic composition comprising a mixture of an altered Fnb and any suitable adjuvant. As used herein, an "adjuvant" is intended to mean any agent that is sufficient to enhance or modify the immune response to the antigen. As used herein, an "immunologically effective" dose of the immunogenic composition is a dose that is suitable to elicit an immune response. The particular dosage will depend upon the age, weight and medical condition of the vertebrate to be treated, as well as on the method of administration. The skilled artisan will readily determine suitable doses. The immunogenic composition can be optionally administered in a pharmaceutically or physiologically acceptable vehicle, such as physiological saline or ethanol polyols such as glycerol or propylene glycol.

Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (see below) or bacterial cell wall components), such as, for example, (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), or MPL+ CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113, 918; one such AGP is 2-[(R)-3-Tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207, 646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor nucrosis factor (TNF), etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an E. coli heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

As mentioned above, muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

The compositions of this invention can be administered to a human or non-human vertebrate by a variety of routes, including parenteral, intrarterial, intradermal, transdermal (such as by the use of slow release polymers), intramuscular, intraperitoneal, intravenous, subcutaneous, oral and intranasal routes of administration. The amount of Fnb employed in such compositions will vary depending upon the route of administration and physical characteristics of the subject vertebrate. Adjustment and manipulation of established dosage ranges used with traditional carrier antigens for adaptation to the present composition is well within the ability of those skilled in the art. The compositions of the present invention are intended for use in the treatment of both immature and adult vertebrates, and, in particular, humans.

The altered Fnb can be administered in conjunction with additional immunogens; the altered Fnb can be administered separately, sequentially or concurrently with the additional immunogen.

The altered Fnb of the present invention can be coupled to a carrier molecule in order to modulate or enhance the immune response. Suitable carrier proteins include bacterial toxins that are safe for administration to vertebrates and immunologically effective as carriers. Examples include pertussis, diphtheria, and tetanus toxoids and non-toxic mutant proteins (cross-reacting materials (CRM)), such as the non-toxic variant of diphtheria toxoid, $CRM_{197}$. Fragments of the native toxins or toxoids, which contain at least one T-cell epitope, are also useful as carriers for antigens. Methods for preparing conjugates of antigens and carrier molecules are well-known in the art (Wong 1991; Bernatowicz and Matsueda 1986; Frisch et al. 1996; Boeckler et al. 1996).

In addition, if a particular peptide region is deleted, one or more epitopes from an antigen from another organism can be inserted into the deleted region, in order to create a bivalent vaccine.

The invention also relates to an immunogenic composition comprising a physiologically acceptable vehicle and a nucleic acid molecule encoding an altered Fnb of S. aureus, wherein the altered Fnb retains immunogenicity and, when incorporated into an immunogenic composition and administered to a vertebrate, does not enhance binding of wild-type Fnb upon subsequent infection of the vertebrate with S. aureus. Such an immunogenic composition is referred to herein as a nucleic acid immunogenic composition or DNA immunogenic composition and is useful for the genetic immunization of vertebrates.

The term, "genetic immunization", as used herein, refers to inoculation of a vertebrate, particularly a mammal, with a nucleic acid immunogenic composition directed against a pathogenic agent, particularly S. aureus, resulting in the generation of an immune response by the vertebrate against S. aureus. A "nucleic acid immunogenic composition" or "DNA immunogenic composition" as used herein, is a nucleic acid construct comprising a nucleic acid molecule encoding a polypeptide antigen, particularly an altered Fnb of S. aureus described herein. The nucleic acid construct can also include transcriptional promoter elements, enhancer elements, splicing signals, termination and polyadenylation signals, and other nucleic acid sequences. The nucleic acid immunogenic composition does not enhance binding of the wild-type Fnb to fibronection or fibrin upon subsequent infection of the vertebrate with *S. aureus*.

The nucleic acid immunogenic composition is produced by standard methods. For example, using known methods, a nucleic acid (e.g., DNA) encoding an altered Fnb of *S. aureus*, is inserted into an expression vector to construct a nucleic acid immunogenic composition (Maniatis et al. 1989).

The individual vertebrate is immunized with the nucleic acid immunogenic composition using standard methods. The vertebrate is immunized (i.e., the composition is administered) subcutaneously, intravenously, intraperitoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, the vertebrate is inoculated with the nucleic acid immunogenic composition through the use of a particle acceleration instrument (a "gene gun"). The form in which it is administered (e.g., capsule, tablet, solution, emulsion) will depend in part on the route by which it is administered. For example, for mucosal administration, nose drops, inhalants or suppositories can be used.

The nucleic acid immunogenic composition can be administered in conjunction with any suitable adjuvant as described above. The adjuvant is administered in a sufficient amount, which is that amount that is sufficient to generate an enhanced immune response to the composition. The adjuvant can be administered prior to, concurrently with, contemporaneously (simultaneously) with, or after inoculation with the nucleic acid immunogenic composition. The adjuvant can also be administered at more than one time. The adjuvant and the nucleic acid immunogenic composition can be administered at approximately the same location on the vertebrate; for example, they are both administered at a marked site on a limb of the vertebrate.

In a particular embodiment, the nucleic acid construct is co-administered with a transfection-facilitating agent. In one embodiment, the transfection-facilitating agent is dioctylglycylspermine (DOGS) (published PCT application publication no. WO96/21356). In another embodiment, the transfection-facilitating agent is a local anesthetic such as bupivacaine (U.S. Pat. No. 5,593,972).

The invention also provides a method of immunizing a vertebrate, e.g., a *S. aureus* seronegative human, against *S. aureus*, comprising administering to the vertebrate a composition comprising an immunologically effective amount of altered Fnb of *S. aureus* described above. Alternatively, the composition comprises a nucleic acid molecule encoding an immunologically effective amount of altered Fnb which retains immunogenicity and which, when incorporated into an immunogenic composition and administered to a vertebrate, is less capable of cross-linking with fibronectin and fibrin, and does not enhance binding of wild-type Fnb with fibronectin and fibrin upon subsequent infection of the vertebrate with *S. aureus*.

Prior to administration in humans, the immunogenic compositions of this invention are evaluated in an animal model. The exemplary, non-limiting animal models will now be described.

In a mouse pyelonephritis model, four week-old female CD-1 mice are inoculated by subcutaneous injection at 0, 3 and 6 weeks with altered Fnb in an appropriate adjuvant. The mice are bled prior to the first inoculation and on week 8. Two days following the final bleed, the mice are challenged by intraperitoneal injection of $3\times10^8$ cfu *S. aureus* Reynolds grown overnight on Columbia salt agar (1× Columbia agar, 0.1% glucose, 1% yeast extract, 0.5% NaCl). Forty-eight hours following challenge, the mice are sacrificed and the bacteria enumerated in the kidneys.

In a rat endocarditis model, three week-old male Sprague-Dawley rats are inoculated by intramuscular injection at 0, 2 and 4 weeks with altered Fnb in an appropriate adjuvant. The rats are bled prior to the first inoculation. On week 6 the rats are bled and undergo surgery to place a polyethylene catheter through the carotid artery and the aortic arch into the left ventricle of the heart. The catheter is held in place with a silk suture and causes the formation of a sterile vegetation. Upon bacterial challenge the vegetation acts as a substrate for bacterial attachment and infection. Two days following surgery the rats are challenged by intravenous injection of $1\times10^5$ cfu *S. aureus* Reynolds grown to mid log phase in tryptic soy broth. Forty-eight hours following challenge, the rats are sacrificed and the bacteria enumerated in the heart.

EXAMPLES

The above disclosure generally describes the present invention. A more complete understanding can be obtained by reference to the following specific Examples. These Examples are described solely for the purpose of illustration and are not intended to limit the scope of the invention.

ABBREVIATIONS

HPLC high performance liquid chromatography;
MALDI-TOF MS matrix-assisted laser desorption/ionization time-of-flight mass spectrometry;
SDS-PAGE sodium dodecyl sulfate polyacrylamide gel electrophoresis;
DTT dithiothreitol;
TCA trichloroacetic acid;
Dansyl 5-dimethylaminonaphthalene-1-sulfonyl;
PTH phenylthiohydantoin.
ECM extracellular matrix proteins
TBS TRIS-buffered saline
PBS sodium phosphate-buffered saline
FXIII Factor XIII or plasma transglutaminase
EDTA sodium salt of ethylenediaminetetraacetic acid
1Q rFnbA recombinant Gln103Ala FnbA mutant
4Q4K rFnbA recombinant Gln103Ala, Gln105Ala, Gln783Ala, Gln830Ala, Lys157Ala, Lys503Ala, Lys620Ala, and Lys762Ala mutant
wt FnbA wild type FnbA

Materials And Methods

Staphylococcal Fibronectin-Binding Protein. The recombinant fibronectin-binding protein A (rFnbA) comprising residues Ala1 through Pro839 from *S. aureus* strain ATCC49525 was produced in *E. coli* and isolated from the soluble fraction of the cell lysate as described previously (Matsuka et al. 2003). Briefly, the fnbA gene encoding FnbA amino acid residues 1-839 was produced by PCR amplification using chromosomal DNA from *S. aureus* strain ATCC49525 as template. The identity of the isolated rFnbA was confirmed using SDS-PAGE, Western blot, and $NH_2$-terminal sequence analysis. Protein concentrations in all experiments were determined using bicinchoninic acid (BCA) assay according to instructions (Pierce Chemical Company, Rockford, Ill.).

Factor XIIIa Catalyzed Incorporation of Dansylcadaverine and Dansyl-PGGQQIV Probes into rFnbA. To incorporate dansylcadaverine (Sigma, St. Louis, Mo.) or dansyl-PGGQ-QIV (custom synthesized by New England Peptide, Inc., Fitchburg, Mass.) into rFnbA, preactivated Factor XIII was used. For this purpose 500 µg/ml of Factor XIII (Haematologic Technologies, Inc., Essex Junction, Vt.) was activated by treatment with 0.25 U/ml of thrombin (Sigma) in TBS, pH 7.4 buffer containing 10 mM dithiothreitol and 20 mM $CaCl_2$. After incubation for 20 min at 37° C., thrombin was inactivated by the addition of hirudin (Sigma) and this mixture was used as Factor XIIIa (Takagi, Aoyama et al. 1995). Factor XIIIa-catalyzed labeling of the reactive glutamine residues within rFnbA was carried out by incubating 1-2 mg of rFnbA for 4 or 18 hours at 37° C. with 2.5 mM dansylcadaverine and Factor XIIIa (30 µg/ml) in 20 mM Tris, pH 7.4, 150 mM NaCl, 5 mM DTT, 5 mM $CaCl_2$ buffer. The labeling of Factor XIIIa-reactive lysine residues was performed by incubating 1-2 mg of rFnbA for 4 or 18 hours at 37° C. with 2 mM dansyl-PGGQQIV and Factor XIIIa (30 µg/ml) in 20 mM Tris, pH 8.5, 15 mM NaCl, 5 mM DTT, 5 mM $CaCl_2$ buffer. The total volume of reaction mixture in both cases was 0.3 ml. At the end of the incubation period, the proteins were precipitated with 7% TCA, harvested by centrifugation (5 min at 14,000×g), and the pellets were extracted repeatedly (8 times) either with 1 ml of ethanol:ether (1:1 vol/vol) to remove unreacted dansylcadaverine or with 1 ml of N,N-dimethylformamide containing 1% N-methylmorpholine and 5% $H_2O$ to remove unreacted dansyl-PGGQQIV probe (Clement, Velasco et al. 1998).

Fragmentation of Dansylcadaverine- and Dansyl-PGGQ-QIV-Labeled rFnbA by Thrombin. Proteolytic fragmentation of dansylcadaverine- or dansyl-PGGQQIV-modified rFnbA was performed using thrombin (Sigma). After the removal of unreacted dansylcadaverine and dansyl-PGGQQIV probes, the modified rFnbA pellets were dissolved in 0.5 ml of TBS, pH 7.4 buffer containing 5 mM $CaCl_2$. Limited proteolysis was carried out by incubating the modified rFnbA with thrombin for 1 hour at 25° C. at an enzyme/substrate ratio of 1:200 (w/w). The reaction was terminated by heating at 95° C. in the presence of 2% SDS, and analyzed by SDS-PAGE.

SDS-PAGE Analysis. Dansylcadaverine- or dansyl-PGGQQIV-modified rFnbA preparations and their thrombin-generated fragments were analyzed by SDS-PAGE using precast 4-20% (BioRad Laboratories, Hercules, Calif.) gradient gels. All SDS-polyacrylamide gels in this study were examined under ultraviolet light and then stained with Coomassie Brilliant Blue R (BioRad Laboratories).

Digestion of Dansylcadaverine- and Dansyl-PGGQQIV-Labeled rFnbA. Enzymatic hydrolysis of the dansylcadaverine-modified rFnbA was achieved by treatment with Glu-C (V-8) protease (Worthington Biochemical Corp., Freehold, N.J.) and L-(tosylamido 2-phenyl)ethyl chloromethyl ketone (TPCK)-treated trypsin (Worthington Biochemical Corp.). Hydrolysis of the dansyl-PGGQQIV-modified rFnbA was performed using Glu-C protease only. Followed by TCA precipitation and extraction, the modified rFnbA pellets were dissolved in 0.3 ml of either TBS, pH 7.4 for cleavage with trypsin or PBS, pH 7.8 for cleavage with Glu-C protease. Enzymatic cleavage was carried out by incubating the modified rFnbA with trypsin or Glu-C protease for 16 h at 37° C. at an enzyme/substrate ratio of 1:20 (w/w). An additional amount of trypsin or Glu-C protease was added to the reaction mixture resulting in a final enzyme/substrate ratio of 1:10 (w/w) and the digestion was continued for another 8 hours at 37° C. The digestion mixture was diluted 1:1 (vol/vol) with 0.2% trifluoroacetic acid, centrifuged at 14,000×g for 5 minutes, and the supernatant was subjected to reverse-phase HPLC.

Reverse Phase HPLC Separation of Dansylcadaverine- and Dansyl-PGGQQIV-Labeled Peptides. Dansylcadaverine- and dansyl-PGGQQIV-labeled peptides were separated on Aquapore RP-300 $C_8$ column (Brownlee Labs, Santa Clara, Calif.) by gradient elution with acetonitrile in 0.1% trifluoroacetic acid. Separation was carried out using a Dynamax HPLC station equipped with a ProStar fluorescence detector (Varian, Walnut Creek, Calif.). Peptides were eluted with a 0-50% linear gradient of acetonitrile over a 90-min interval at a flow rate of 0.5 ml/min. Elution of peptides was detected by monitoring of absorbance at 210 nm and fluorescence at 550 nm with excitation at 350 nm. The fluorescent tracer peaks were collected and after concentration to smaller volumes (50-200 µl) were reinjected to the same column. The second round of elution was performed using a 10-20% or 20-35% linear gradient of acetonitrile over a 60-min interval at a flow rate of 0.5 ml/min. The isolated dansylcadaverine- or dansyl-PGGQQIV-labeled peptides were subjected to mass spectral and $NH_2$-terminal sequence analysis.

Sequence Analysis. The $NH_2$-terminal sequence analysis was performed with an Applied Biosystems model 490 sequenator. Selected samples were also submitted for service analysis to M-Scan Inc. These samples were analyzed using Applied Biosystems model 477A sequenator. The $NH_2$-termini of the isolated peptides were determined by sequencing for up to 18 cycles.

Theoretical Estimation of the Molecular Masses of Peptides. Calculation of the molecular masses of trypsin- and Glu-C proteinase-generated peptides was performed from the known primary sequence of staphylococcal rFnbA using Peptide Companion V1.25 software. The effect of dansylcadaverine (335.50 Da) or dansyl-PGGQQIV (932.00 Da) modification on the mass of the peptide was calculated by the addition of molecular mass of the probe. Since the formation of each $\epsilon$-($\gamma$-glutamyl)lysine isopeptide bond is accompanied by the release of one ammonia (17.04 Da), the final molecular mass values were adjusted accordingly.

Mass Spectral Analysis. The determination of molecular masses of the isolated peptides was performed using MALDI-TOF mass spectrometer Voyager DE-STR (Persepctive Biosystems, Foster City, Calif.). Ions formed by laser desorption at 337 nm ($N_2$ laser) were recorded at an acceleration voltage of 20 kV in the reflector mode. In general, 200 single spectra were accumulated for improving the signal/noise ratio and analyzed by the use of the Data Explorer software supplied with the spectrometer. The $\alpha$-cyano-4-hydroxycinnamic acid (Aldrich Chemical Co., Milwaukee, Wis.) was used as an ultraviolet-absorbing matrix. One µl of a 10 mg/ml solution of the matrix compounds in 70% acetonitrile/0.1% trifluoroacetic acid was mixed with 1 µl peptide solution (5-10 pmole/µl). For MALDI-TOF MS, 1 µl of this mixture was spotted on a stainless steel sample target and dried at room temperature. The mass spectra were calibrated using external standards: bovine serum albumin, human Glu1-fibrinopeptide B, human angiotensin I, and synthetic des-Arg1-bradykinin. The mass accuracy was in the range of 0.1%.

Example 1

Factor XIIIa-Directed Incorporation of Dansylcadaverine and Dansyl-PGGQQIV into rFnbA and Fragmentation of Probe-Decorated Protein by Thrombin It has been reported that fibronectin-binding protein A from *S. aureus* strain ATCC49525 serves as a bifunctional substrate for coagulation Factor XIIIa that contains both reactive Gln and Lys residues (Matsuka et al. 2003). To assess the location of reactive Gln and Lys residues within FnbA, amine donor (dansylcadaverine) or amine acceptor (dansyl-PGGQ-QIV) fluorescent probes were incorporated into rFnbA by the catalytic action of Factor XIIIa. Reactions were carried out for 4 or 18 hours, followed by the removal of unreacted probes and the fragmentation of fluorescent-tracer-labeled rFnbA by thrombin. The existence of a single Arg202-Gly203 peptide bond within FnbA that is sensitive to thrombin attack allows the generation of two fragments representing the N- and C-terminal portions of rFnbA with theoretically estimated molecular masses of 22 and 70.7 kDa, respectively. The products of thrombin-mediated cleavage of rFnbA were evaluated by SDS-PAGE with subsequent examination of the gels under UV light prior to Coomassie Brilliant Blue staining (FIG. 1). Incubation of dansylcadaverine- or dansyl-PGGQQIV-decorated rFnbA with thrombin resulted in the appearance of two discrete fragments, consistent with the hydrolysis of a single peptide bond. The mobility of the thrombin-generated low- and high-molecular mass fragments on SDS-PAGE was somewhat lower than that expected for 22 kDa and 70.7 kDa fragments. This observation, however, is consistent with the overall low mobility on SDS-PAGE of the band corresponding to the parent rFnbA (both non-modified and fluorescent probe-modified), which migrates between the 120 kDa and 203 kDa standards (Matsuka et al. 2003). The molecular mass obtained for rFnbA using mass-spectral analysis was very close to the value estimated from the primary sequence (92.656 kDa), therefore, suggesting abnormally low migration of rFnbA and its fragments on SDS-PAGE.

The modification of rFnbA with dansylcadaverine catalyzed by Factor XIIIa for 4 h resulted in the fluorescence of the band corresponding to monomeric rFnbA (FIGS. 1A and C, lane 1). The thrombin-generated cleavage of the dansylcadaverine-decorated rFnbA and subsequent analysis of the reaction mixture by SDS-PAGE revealed that fluorescence almost entirely localized within the low molecular mass fragment. The band corresponding to the prominent high molecular mass fragment accommodated only a small fraction of the total dansylcadaverine fluorescence (FIGS. 1A and C, lane 2). Similar results were observed with rFnbA modified with dansylcadaverine over the extended, 18-hour period of time (FIGS. 1A and C, lanes 3 and 4). Prolonged incubation of rFnbA with dansylcadaverine and Factor XIIIa also resulted in the appearance of the minor high molecular mass band corresponding to rFnbA dimer (FIGS. 1A and C, lane 3). Incubation of rFnbA in the presence of Factor XIIIa and dansyl-PGGQQIV peptide for 4 hours or 18 hours resulted in the incorporation of the probe in the monomeric rFnbA as well as in the appearance of the bands corresponding to dimers and high molecular mass polymers (FIGS. 1B and D). Nevertheless, it is apparent that under the experimental conditions employed, protein cross-linking was almost completely inhibited and the incorporation of dansylcadaverine and dansyl-PGGQQIV probes occur in the predominantly monomeric form of rFnbA. When the dansyl-PGGQQIV-modified rFnbA was subjected to thrombin-catalyzed cleavage, only the high molecular mass fragment exhibited fluorescence upon UV illumination (FIGS. 1B and D, lanes 2 and 4). Thus, limited proteolysis data revealed that the major glutamine acceptor and lysine donor sites are spatially separated within the polypeptide chain of the rFnbA molecule and located in the N- and C-terminal regions, respectively.

Example 2

Identification of the rFnbA Glutamine Acceptor Sites Involved in Factor XIIIa Cross-Linking Reactions To identify the specific reactive Gln residue(s) within rFnbA, the latter was incubated for 4 and 18 hours in the presence of Factor XIIIa and a molar excess of the fluorescent probe dansylcadaverine. Following the dansylcadaverine labeling reaction, the modified rFnbA preparations were washed from the unreacted probe and then digested with trypsin. HPLC separation of the tryptic peptides produced after a 4 hour Factor XIIIa-catalyzed incorporation of dansylcadaverine into rFnbA revealed a complex profile at 210 nm (FIG. 2A). In contrast, only one major peak with retention time of approximately 44 min was detected in the same sample upon monitoring of fluorescence at 550 nm (FIG. 2B, peak 1). Extension of the incubation time of rFnbA in the presence of Factor XIIIa and dansylcadaverine from 4 hours to 18 hours and subsequent digestion with trypsin did not have an impact either on the elution profile at 210 nm (FIG. 2C) or on intensity or retention time of the major fluorescent peak (FIG. 2D, peak 1). At the same time, extending the time of dansylcadaverine incorporation into rFnbA resulted in the increase of intensities of two minor fluorescent peaks depicted as 2 and 3 (FIG. 2D). The fluorescent tracer-decorated peptides labeled as peak 1 (FIG. 2B) and peaks 1, 2, 3 (FIG. 2D) were collected and after a second passage through a $C_8$ column were characterized by $NH_2$-terminal sequence and mass spectral analysis (Table 2). Sequence analysis of the peptide from the major fluorescent peak 1 revealed that it corresponds to a 13-mer fragment derived from the $NH_2$-terminal portion of the rFnbA. During Edman degradation, the residue in the $12^{th}$ cycle was not detected, while proper sequencing was resumed in the next $13^{th}$ cycle. The $12^{th}$ residue, which did not yield a conventionally recognized amino acid in the Edman procedure, corresponds to Gln103 therefore suggesting that it was modified. Two other Gln residues (Gln95 and Gln97) located in this peptide were released as PTH (phenylthiohydantoin)-derivatives in cycles 4 and 6, respectively. Sequencing data obtained for the tryptic 13-mer peptide (peak 1) are further supported by the results of mass-spectral analysis. The observed mass of this peptide showed m/z 1783.83, corresponding to the calculated mass of the peptide containing a single dansylcadaverine modification, 1783.07 (Table 2). Sequence and mass-spectral analysis of the tryptic peptide from the minor fluorescent peak 3 in FIG. 2D showed that this peptide was also derived from the $NH_2$-terminal region of the FnbA molecule. Upon sequencing, a single Gln residue (Gln105) was not detected in the first cycle, but the registration of PHT-derivatives of the residues shown in Table 2 was resumed in the following cycles, suggesting that Gln105 can be identified as another acceptor site. The observed mass of this peptide corresponded to the theoretical value with a single dansylcadaverine modification (Table 2). The material from peak 2 was not sufficiently homogeneous for $NH_2$-terminal sequencing even after additional passage through a $C_8$ reverse phase column, and therefore, was not positively identified by Edman degradation.

Figure 3:
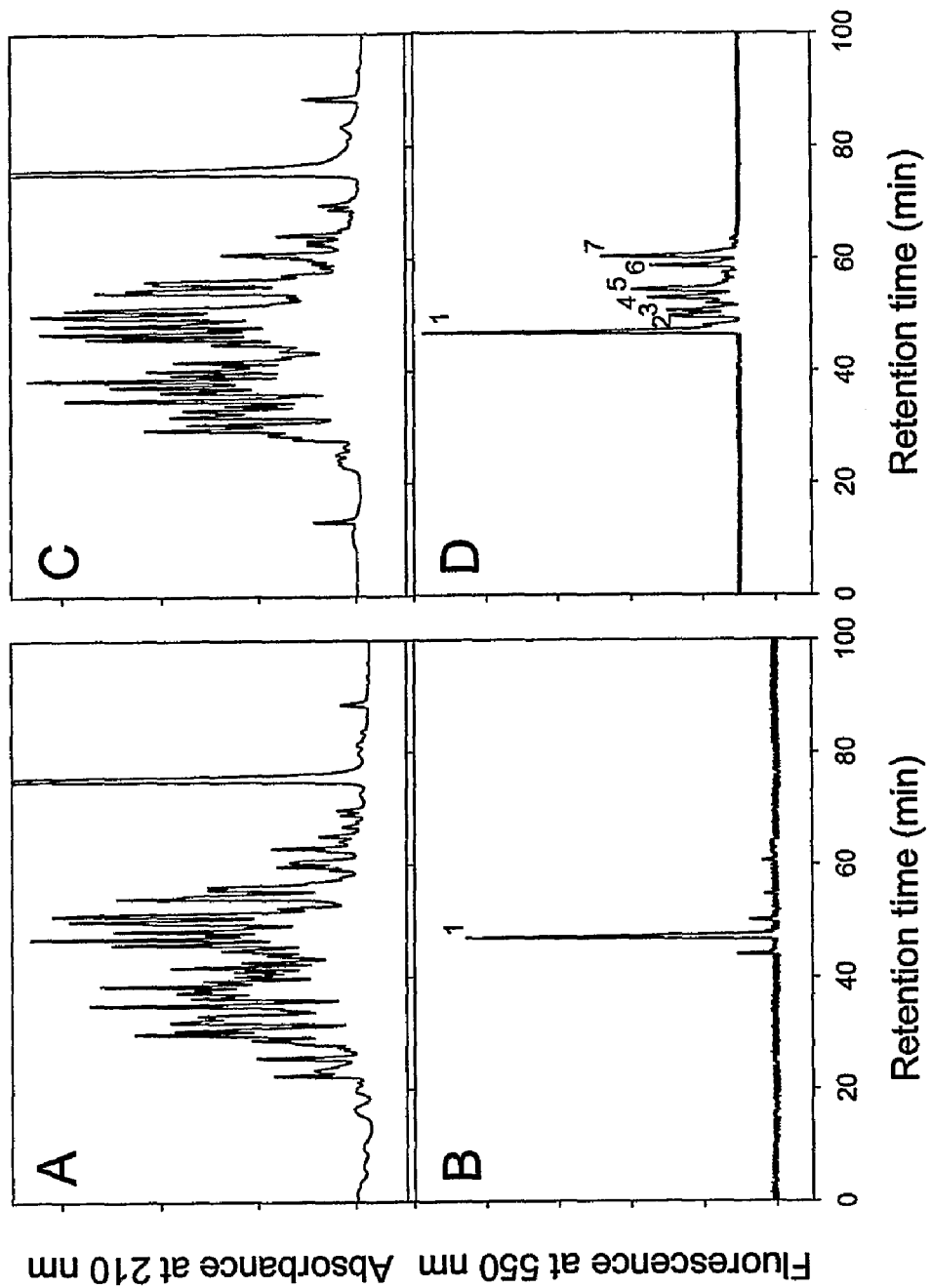
FIG. 3 depicts HPLC separation of dansylcadaverine-labeled peptides from the Glu-C protease digest of Factor XIIIa-modified rFnbA. Factor XIIIa-catalyzed incorporation of dansylcadaverine into rFnbA was carried out for 4 (panels A and B) and 18 hours (panels C and D). The dansylcadaverine-labeled rFnbA preparations were digested by Glu-C protease and the peptides were separated on an Aquapore RP-300 $C_8$ reverse phase column. The elution was monitored by absorbance at 210 nm as well as by fluorescence at 550 nm. Fluorescent peaks 1 (panels B and D), 2, 3, 4, 5, 6 and 7 (panel D) were collected, and after a second round of reverse phase chromatography subjected to $NH_2$-terminal sequence and mass-spectral analysis.

Because some of the predicted tryptic peptides were rather large (particularly those originating from the COOH-terminal portion of the protein), digestion of dansylcadaverine-modified rFnbA was also performed using Glu-C proteinase, which generated smaller and more manageable peptides. The rFnbA and Factor XIIIa were incubated in the presence of dansylcadaverine, as described in "Materials and Methods," and digested with Glu-C proteinase. A single fluorescent peak with a retention time of 46 minutes was repeatedly observed in the Glu-C proteinase digestion mixture after the modification of rFnbA with dansylcadaverine over a 4 hour period (FIG. 3 B, peak 1). The extended, 18-hour incorporation of dansylcadaverine into rFnbA, followed by Glu-C digestion, produced the same major peak 1 and multiple minor peaks designated as 2, 3, 4, 5, 6, and 7 (FIG. 3 D). As shown in Table 2, four peptides were recovered from the Glu-C proteinase digestion mixture and positively identified. The peptides from peaks 1 and 7 contained the same reactive Gln103 and Gln105 residues as those identified in the tryptic digests. Both peptides correspond to the sequence 93-107 and differ only by the number of dansylcadaverine modifications. The peptide from the major fluorescent peak 1 contains one modified Gln103 residue, while both Gln103 and Gln105 are modified in the peptide in peak 7. The Glu-C proteinase digestion also produced two fluorescent peptides derived from the COOH-terminal portion of rFnbA. The peptides from peaks 4 and 6 contained modified Gln830 and Gln783 residues, respectively (Table 2).

The analysis of the several separate dansylcadaverine labeling experiments performed over 4 hours and 18 hours followed by either trypsin or Glu-C proteinase digestion suggested that Gln103 serves as a major amine acceptor site for Factor XIIIa in rFnbA. The high reactivity of the Gln103 site is responsible for the origin of a single major fluorescent peak 1 corresponding to either the tryptic peptide ETTQSQDNSGDQ$_{103}$R (comprising amino acids 92 to 104 of SEQ ID NO:1, the elution profile of which is depicted in FIG. 2B) or Glu-C proteinase-generated TTQSQDNSGDQ$_{103}$RQVD peptide (comprising amino acids 93 to 107 of SEQ ID NO:1, the elution profile of which is depicted in FIG. 3B). Modification of the Gln103 was fully completed after 4 hours of reaction (or earlier), since further incubation with Factor XIIIa did not affect the intensity of peak 1 (FIGS. 2D and 3D). In contrast, recovery of additional fluorescent peptides from the trypsin (peaks 2, 3) or Glu-C proteinase (peaks 4, 6, and 7) digestion mixtures was achieved only upon extended treatment with Factor XIIIa. Intensities of these fluorescent peaks were still significantly lower, compared with that of the major peak 1, indicating that only a fraction of reactive Gln residues at positions 105, 783, and 830 underwent modification. Thus, modification experiments with dansylcadaverine revealed that rFnbA contains one major (Gln103) and three minor (Gnl105, Gln783, and Gln830) Factor XIIIa-reactive amine acceptor sites.

Example 3

Identification of the rFnbA Lysine Donor Sites Involved in Factor XIIIa Cross-Linking Reactions The Factor XIIIa-mediated titration of Lys side chains of rFnbA was performed using the dansyl-PGGQQIV peptide patterned on the N-terminal sequence of fibronectin. The rFnbA was incubated for 4 hours in the presence of Factor XIIIa and dansyl-PGGQQIV probe and then digested with Glu-C proteinase. The HPLC separation of Glu-C proteinase-generated peptides again revealed multiple peaks detected at 210 nm and only a few fluorescent peaks, eluting in the range of approximately 60 minutes (FIGS. 4 A and B). However, with the exception of the peak marked by an asterisk (FIG. 4 B), the degree of labeling and consequently the level of purity of the probe-modified peptides were not sufficient for required sequence analysis. To improve the recovery of dansyl-PGGQQIV-modified peptides, the rFnbA was incubated with Factor XIIIa and dansyl-PGGQQIV probe for 18 hours and digested with Glu-C proteinase as described in "Materials and Methods." The HPLC separation of this digestion mixture produced a total of seven fluorescent peaks (FIG. 4 D). The elution profile of fluorescent peaks 1-7 (FIG. 4 D) was similar to that of the digestion mixture generated after 4 hours of rFnbA modification (FIG. 4 B), suggesting production of the same peptides with a higher degree of labeling. Each of these fluorescent peaks (asterisk-labeled peak from FIG. 4 B and peaks 1-7 from FIG. 4 D) was additionally purified on a reverse-phase C$_8$ column, and then subjected to evaluation by mass-spectral and sequencing analysis. The results of performed analysis are summarized in Table 3. A total of six modified peptides were positively identified using both mass-spectral and sequencing analysis. High confidence sequences were obtained for peaks 4, 5, and 7 fractions, identifying Lys157, Lys620, and Lys503 unambiguously as probe-modified residues (Table 3). During Edman degradation dansyl-PGGQQIV-modified Lys residues are not recognized as conventional PTH-derivatives, and therefore, cannot be detected. Upon sequencing of peak 4 this result was observed in the $2^{nd}$ cycle, while the Val residue was released as PTH-derivative in the $1^{st}$ cycle. Sequencing resumed in the following $3^{rd}$ cycle and continued without interruptions. The Lys residue yielded in the $9^{th}$ cycle further reinforced the conclusion that the modified lysine (Lys157) was present in cycle 2. Analysis of peptides from peaks 5 and 7 revealed the interruption of sequencing in cycles 3 and 2, respectively. Again, these data suggest that Lys620 (cycle 3 in peptide 5) and Lys503 (cycle 2 in peptide 7) were modified by Factor XIIIa. As can be seen from Table 3, the results of NH$_2$-terminal sequence analysis obtained for peaks 4, 5, and 7 are consistent with the observed m/z values. Each of these probe-modified fractions exhibited an m/z value that precisely matched the calculated mass of the respective peptide containing a single dansyl-PGGQQIV modification (Table 3). Each of the fluorescent peaks 1 and 2 represented a mixture of two labeled and unlabeled peptides, present in essentially equal amounts. Reliable reading of the double sequence was achieved by utilizing the known primary sequence of FnbA and the map of predicted cleavage sites. Similarly, reading of a sequence obtained for fluorescent peak 6 was also accomplished by knowing the amino acid sequence of FnbA and the location of predicted cleavage sites catalyzed by Glu-C proteinase. Analysis of the isolated fractions revealed that some dansyl-PGGQQIV-labeled peptides were derived from the same regions of the polypeptide chain. Partial hydrolysis of the Asp160-Val161 peptide bond by Glu-C proteinase resulted in the recovery of a shorter version of probe-modified peptide 1 (fragment 156-160) and a longer peptide 4 (fragment 156-168). Similarly, incomplete hydrolysis of the Asp629-His630 peptide bond resulted in the production of peptide 5 (fragment 618-629) and peptide 6 (fragment 618-634) (Table 3). Thus, Lys157 and Lys620 again were identified as probe-modified residues in fluorescent peaks 1 and 6, respectively. Factor XIIIa-catalyzed modification of Lys762 was demonstrated by the sequencing of the fraction corresponding to fluorescent peak 2. Mass spectral analysis of fractions 1, 2, and 6 provided another line of evidence supporting the results of NH$_2$-terminal sequencing. The mass peaks at m/z 1432.37, 1820.22, and 2614.83 were present in fractions 1, 2, and 6, respectively. The observed masses obtained for fluorescent peaks 1, 2, and 6 corresponded to the theoretical values with a single dansyl-PGGQQIV modification each (Table 3). The fluorescent peak depicted by an asterisk (FIG. 4 B) represented a mixture of two peptides. The reading of this fraction was again achieved by knowing the primary sequence of FnbA. The unlabeled peptide was identified as fragment 266-280 (FIG. 5) while the tracer-containing peptide corresponded to peak 5 on FIG. 4 D and contained the single probe-modified Lys620 (Table 3). The fraction corresponding to peak 3 (FIG. 4 D) appeared to be a mixture of several peptides, sequences of which could not be resolved by Edman degradation. Thus, the treatment of rFnbA with Factor XIIIa in the presence of dansyl-PGGQ-QIV probe resulted in the specific modification of Lys157, Lys503, Lys620, and Lys762, suggesting that these residues serve as amine donor sites.

Example 4

Substitution of Identified Factor XIIIa-Reactive Gln and Lys Residues Using Site-Directed Mutagenesis Replacements of identified reactive Gln and Lys residues were performed by introduction of each mutation separately. For this purpose synthetic oligonucleotides spanning the desired coding region (including Gln to Ala or Lys to Ala changes) were utilized for PCR amplification of the rFnbA gene. Utilization of specific subclones of the 2520 by gene (e.g., a subclone spanning Gln103, Gln105, and Lys157 and one spanning Gln503, Lys620, Lys762, Gln783, and Gln830) simplified "modular stepwise" reconstruction of the altered gene containing all eight mutations. In each instance, after the reconstructed gene was subcloned into an *E. coli* expression vector, the mutated rFnbA gene was sequenced to confirm the presence of the desired mutations. For example, the Gln103 residue of FnbA was changed to Ala using the synthetic oligonucleotide GACAATAGCGGAGAT GCAAGACAAGTAGATTTAATAC set forth in SEQ ID NO:15 (and its complement) to anneal to plasmid pLP1143, which contains nucleotides corresponding to roughly, the 5' half of the wild type fnbA gene. This primer was extended using Pfu Turbo polymerase to create multiple unmethylated copies of the altered region of the fnbA gene (Gln103Ala). After digestion of the methylated template DNA with DpnI, transformation of *E coli* with the products of the above reactions reduces recovery of the original methylated (wild type) copy. Plasmids recovered from the transformation mixture were then sequenced across a portion of the cloned fnbA region to confirm the presence of the desired sequence as set forth in SEQ ID NO:15: GACAATAGCGGAGAT GCAAGACAAGTAGATTTAATAC, with the codon GCA (underlined) substituting an alanine for the original codon for Gln (CCA) in the plasmid fnbA103A. To obtain a full-length fnbA coding sequence, the 5' half of the mutated Gln103Ala fnbA gene contained in plasmid fnbA103A was excised using NcoI and KpnI. The resulting DNA fragment was then cloned into the NcoI and KpnI sites of the pLP1125 (containing the full length wild type fnbA). The product of this ligation (pLP1149) contains the Gln103Ala mutation in the full-length fnbA gene as determined by DNA sequence analysis of the entire 2.517 kb fnbA gene.

In a similar fashion, Lys762 of the wild-type FnbA was replaced by Ala using the synthetic oligonucleotide GAA-GATACAGAGGCAGACAAACCTAAG (set forth in SEQ ID NO:16), in which the codon for Ala (GCA, underlined) replaces the codon for Lys (AAA). This primer was used to anneal to the plasmid pLP1144, which contains nucleotides corresponding to roughly, the 3' half of the wild-type fnbA. After primer extension and transformation of the *E. coli* host, as described above, the presence of the mutated region was confirmed by DNA sequence analysis showing replacement of the Lys codon (AAA) by the codon for Ala (GCA, underlined) in plasmid fnbA762A. The Lys762Ala mutation contained in plasmid fnbA762A was introduced into the full length fnbA gene by digesting plasmid fnbA762A with SpeI and NotI and ligating the resulting fragment into pLP1125 cut with the same enzymes. The resulting recombinant plasmid, pLP1150 contains the Lys762Ala mutation as determined by DNA sequencing of the entire fnbA gene.

The double mutation, fnbAQ103A,Q105A (Gln at 103 and 105 replaced by Ala) was constructed using the synthetic oligonucleotide sequence set forth in SEQ ID NO:17: GGAGATGCAAGAGCAGTAGATTTAATAC, which contains the codon for Ala105 (GCA, underlined) in addition to the Gln103Ala mutation (italicized). This primer was annealed to pLP1149 (fnbAQ103A) and the extension product (plasmid 5'103A+5'105A) sequenced across the portion of the gene containing the mutation. The NcoI, KpnI fragment, containing the double mutation was then used to replace the wild-type sequence in pLP1125 to create pLP1155. The entire fnbA gene contained in pLP1155 was sequenced to confirm the presence of the double mutation. The double mutation Lys620Ala, Lys762Ala was constructed using the oligonucleotide set forth in SEQ ID NO:18: CGAA-GAGTCTACAGCAGGTATTGTAACTG to prime DNA synthesis using the template, plasmid pLP1150. This oligonucleotide contained the GCA codon for Ala620 (underlined) in place of the wild type Lys620 codon. The resulting plasmid contained the original Lys762Ala mutation of pLP1150 plus the Lys620Ala mutation as determined by DNA sequencing. The doubly mutated region was subcloned into pLP1125 with the SpeI, NotI DNA fragment from the double mutant replacing the wild-type sequence. The resulting plasmid, pLP1156 was sequenced across the entire fnbA gene, confirming the presence of the Lys620Ala, Lys762Ala mutations. This procedure is repeated until all of the mutations have been constructed in the two halves of the fnbA gene. Each set of mutations is combined by the subcloning procedure outlined above, resulting in a fnbA gene containing all eight mutations.

Example 5

Evaluation of the Cross-Linking Properties of the rFnbA Mutant

The reduction of reactivity of the mutated rFnbA towards Factor XIIIa is demonstrated using different approaches. The fluorescent low molecular probes, dansylcadaverine and dansyl-PGGQQIV, are utilized for the evaluation of transglutaminase reactivity of the mutated rFnbA. The lack of incorporation of the above probes into the mutated rFnbA by Factor XIIIa indicates the absence of reactive Gln and Lys residues. Demonstration of the reduced or eliminated reactivity of mutated rFnbA towards Factor XIIIa is also performed by the evaluation of its ability to undergo Factor XIIIa-catalyzed cross-linking to human fibronectin and fibrin. The Factor XIIIa-catalyzed incorporation of fluorescent probes as well as the cross-linking reactions to fibronectin or fibrin are also performed with the wild-type rFnbA as a positive control.

In the following examples, site-directed mutagenesis was used to replace the identified reactive Gln and Lys sites to Ala residues and the effect of these mutations was evaluated in FnbA-fibrin and FnbA-fibronectin cross-linking reactions. The major reactive Gln103 site was replaced with Ala in a single residue FnbA mutant, which was designated as 1QFnbA. All of the identified Gln103, 105, 783, 830 and Lys157, 503, 620, 762 sites were substituted with Ala residues in the FnbA mutant, which was designated as 4Q4KFnbA. The Factor XIIIa reactivity of both the 1Q FnbA and 4Q4K FnbA mutants was compared with that of the wild-type FnbA receptor and the results are discussed with regard to the role of the host transglutaminase in staphylococcal adhesion and colonization.

Example 6

Generation of the 1Q FnbA Mutant

Q103A Mutation

The 1533 region of the fnbA gene encoding the $NH_2$-terminal A region (residues 1-511) of staphylococcal FnbA was produced by PCR amplification using chromosomal DNA from S. aureus strain ATCC49525 as template. Amplification was performed using the following forward 5'-GG CCATGGCATCAGAACAAAAGACAACTACAG-3' and reverse 5-CGA GGATCCTTATGTTTCAATTTGCTTGGC-3':PCR primers, having the nucleotide sequences set forth in SEQ ID NO:19 and SEQ ID NO:20, respectively. The forward primer incorporated an Nco I restriction site (underlined) and ATG initiation codon immediately before the coding region of the mature sequence. The reverse primer included a TAA stop codon immediately after the coding segment, followed by a Bam HI site (underlined). The amplified DNA fragment was isolated, treated with Nco I and Bam HI restriction enzymes and subsequently ligated into the pET-28a vector (Novagen, Inc., Madison, Wis.). Mutagenesis of fnbA gene was performed using QuikChange II XL Site-Directed Mutagenesis Kit (Stratagene, La Jolla, Calif.). To synthesize the mutant DNA strand we employed the pET-28a vector containing 1533 by fragment of the fnbA gene as a template. Synthetic oligonucleotide 5'-GACAATAGCGGAGATGCAAGA-CAAGTAGATTTAATAC-3' set forth in SEQ ID NO:21) and its complement were utilized as mutagenic primers. Mutagenic primers contain the GCA codon that replaced CAA to generate the desired Gln→Ala mutation at position 103. Thermal cycling, extension of primers using Pfu Ultra DNA polymerase, and digestion of (hemi)methylated template with endonuclease Dpn I (Stratagene, La Jolla, Calif.) were performed according to manufacturer's instructions. Mutated DNA was transformed into competent XL 10-Gold E. Coli cells (Stratagene) for nick repair. The resultant plasmid DNA was digested with Nco I and Kpn I restriction enzymes and the 680 by DNA fragment of the fnbA gene containing the CAA→GCA mutation was subcloned into pET-28a vector containing the wild-type fnbA gene (FnbA residues 1-839) (Matsuka et al. 2003). Ligation of the mutated 680 by DNA fragment into the pET-28a/fnbA gene vector using Nco I and Kpn I restriction sites resulted in restoration of the 2517 by fnbA gene that encodes mutated FnbA (Q103A FnbA). The resulting pET-28a plasmid (Q103A FnbA mutant) was transformed into BL21 (DE3) E. coli cells for protein expression. The presence of the desired Q103A mutation was confirmed by sequencing the mutated region of fnbA gene.

Example 7

Generation of the 4Q4K FnbA Mutant

Gln103Ala, Gln105Ala, Gln783Ala, Gln830Ala, Lys157Ala, Lys503Ala, Lys620Ala, and Lys762Ala Mutations Introduction of the K762A mutation. The region of the fnbA gene encoding the COOH-terminal region (residues 512-839) of staphylococcal FnbA was produced by PCR amplification using chromosomal DNA from S. aureus strain ATCC49525 as template. Amplification was performed using the following forward 5'-GAG CCATGGATATTAAGAGTGAATTAGG-3' and 5'-CGA GGATCCGGCGTTGTATCTTCTTCAATC-3' reverse PCR primers, having the nucleotide sequences set forth in SEQ ID NO:22 and SEQ ID NO:23, respectively. The forward and reverse primers incorporated an Nco I and Bam HI sites (underlined), respectively. The amplified DNA fragment was isolated, treated with Nco I and Bam HI restriction enzymes and ligated into a pET-28a vector (Novagen, Inc., Madison, Wis.). Synthesis of the mutated DNA strand was performed using the pET-28a vector containing a 984 by fragment of the fnbA gene as a template and synthetic oligonucleotide 5'-GAAGATACAGAGGCAGACAAACCTAAG-3' set forth in SEQ ID NO:24 and its complement as mutagenic primers. Mutagenic primers contained the GCA codon that replaced AAA to generate the desired Lys→Ala mutation at position 762. Mutated DNA was transformed into competent XL 10-Gold E. coli cells (Stratagene, La Jolla, Calif.). The resultant plasmid was digested with Spe I and Not I restriction enzymes and the 612 by mutated DNA fragment was subcloned into pET-28a vector containing full-length wild-type fnbA gene (FnbA residues 1-839).

Introduction of the Q105A and K157A mutations. The Q105A and K157A mutations were generated consecutively using the pET-28a template containing single (Q103A) and double (Q103A, Q105A) mutations in the fnbA gene, respectively. Synthetic oligonucleotides 5'-GGAGATGCAAGA GCAGTAGATTTAATAC-3' (set forth in SEQ ID NO:25) and its complement were employed as mutagenic primers for Q105A mutation, while 5'-GTTTCAGAAGTC GCAGGTACAGATGTG-3' set forth in SEQ ID NO:26 and its complement were utilized for introduction of the K157A mutation. Mutated DNA containing three (Q103A, Q105A, and K157A) mutations was transformed into competent DH 10B E. coli cells (Invitrogen, Carlsbad, Calif.). The resultant plasmid was digested with Nco I and Kpn I restriction enzymes and the 680 by mutated DNA fragment was isolated for subsequent subcloning into the pET-28a vector.

Introduction of the K620A mutation. The K620A mutation was generated using the pET-28a template containing the single (K762A) mutation in fnbA gene. This was achieved using mutagenic oligonucleotide 5'-CGAAGAGTCTACA GCAGGTATTGTAACTG-3' (set forth in SEQ ID NO:27) and its complement. Mutated DNA containing two (K620A and K762A) mutations was transformed into competent DH 10B E. coli cells (Invitrogen, Carlsbad, Calif.). The resultant plasmid was digested with Bsr GI and Spe I restriction enzymes and the 1119 by mutated DNA fragment was isolated and subcloned into the pET-28a vector containing the fnbA gene with the single K762A mutation.

Introduction of the K503A mutation. The K503A mutation was generated using the pET-28a template containing double (K620A, K762A) mutations in the fnbA gene. Synthetic oligonucleotide 5'-GCAGTACGATGCC GCGCAAATTATTGAAAC-3' (set forth in SEQ ID NO:28) and its complement were utilized as mutagenic primers. Mutated DNA was transformed into competent DH 10B E. coli cells (Invitrogen, Carlsbad, Calif.). The resultant plasmid was digested with Kpn I and Spe I restriction enzymes and the 1256 by mutated DNA fragment containing K503A and K620A mutations was isolated for subsequent subcloning into pET-28a vector.

Introduction of the Q783A mutation. The Q783A mutation was generated using the pET-28a template containing double (K620A, K762A) mutations in the fnbA gene. Synthetic oligonucleotide 5'-GACAGTGTGCCA GCAATTCATGGATTC-3' (set forth in SEQ ID NO:29) and its complement were utilized as mutagenic primers. Mutated DNA was transformed into competent DH 10B E. coli cells (Invitrogen, Carlsbad, Calif.). The resultant plasmid was digested with Spe I and Not I restriction enzymes and the 612 by mutated DNA fragment containing two (K762A and Q783A) mutations was isolated for subsequent subcloning into the pET-28a vector.

Three DNA fragments containing seven mutations (680 bp—Q103A, Q105A, K157A; 1265 bp—K503A, K620A; and 612 bp—K762A, Q783A) were ligated into pET-28a vector digested with Nco I and Not I restriction enzymes, resulting in restoration of the 2516 by fnbA gene that encodes Q103A, Q105A, K157A, K503A, K620A, K762A, Q783A FnbA mutant.

Introduction of the Q830A mutation. The Q830A mutation was generated using a pET-28a template containing three (K620A, K762A, and Q783A) mutations in fnbA gene. Synthetic oligonucleotide 5'-CAAAATGAAGGT GCACAAACGATTGAAG-3' set forth in SEQ ID NO:30) and its complement were utilized as mutagenic primers. Mutated DNA was transformed into competent DH 10B E. coli cells (Invitrogen, Carlsbad, Calif.). The resultant plasmid was digested with Spe I and Not I restriction enzymes and the 612 by mutated DNA fragment containing K762A, Q783A, and Q830A mutations was isolated for subcloning into a pET-28a vector. This resulted in restoration of the fnbA gene that encodes FnbA containing a total of eight Q103A, Q105A, K157A, K503A, K620A, K762A, Q783A, and Q830A mutations.

The resultant plasmid DNA was transformed into BL21 (DE3) E. coli cells for protein expression. Each generated DNA fragment containing specific mutation was sequenced prior to subcloning into pET-28a vector. The restored mutated fnbA gene was sequenced once more to confirm the presence of desired mutations and the integrity of the entire coding region.

Proteins. Expression and purification of the wild-type FnbA, and 1Q, and 4Q4K FnbA mutants were performed according to procedures described elsewhere (Matsuka et al. 2003). All isolated FnbA preparations were dialyzed against 20 mM Tris, pH 7.4, 150 mM NaCl, aliquoted, and stored frozen at −20° C.

Antibodies. Anti-rFnbA polyclonal antibodies were generated in rabbits as described earlier (Matsuka et al. 2003). Mouse monoclonal anti-fibrinogen Aα chain (Aα 529-539, clone 1C2-2) antibody was purchased from Accurate Chemical and Scientific Corp. (Westbury, N.Y.). Mouse monoclonal anti-fibronectin antibody (clone 2B6-F9) was obtained from Cedarlane Laboratories (Hornby, Ontario, Canada). Goat anti-rabbit and anti-mouse IgG alkaline phosphatase conjugates were purchased from BioRad Laboratories (Hercules, Calif.).

Theoretical Estimation of the Molecular Masses of Peptides. Calculation of the molecular mass of the peptides produced by Glu-C proteinase was performed from the known primary sequence of staphylococcal rFnbA using Peptide Companion V1.25 software (CSPS Pharmaceuticals, Inc., San Diego, Calif.). The effect of the dansyl-PGGQQIV (930.44 Da) modification on the mass of the peptide was calculated by considering the mass increase due to the probe. Since the formation of each $\epsilon$-($\gamma$-glutamyl)lysine isopeptide bond is accompanied by the release of one ammonia (17.03 Da), the final molecular mass values were adjusted accordingly.

Reversed Phase HPLC Separation of Dansyl-PGGQQIV-Labeled Peptides. Dansyl-PGGQQIV-labeled peptides were separated on Aquapore RP-300 $C_8$ column (Brownlee Labs, San Francisco, Calif.) by gradient elution with acetonitrile in 0.1% trifluoroacetic acid. Separation was carried out using Dynamax HPLC station equipped with ProStar fluorescence detector (Varian, Palo Alto, Calif.). Peptides were eluted with a 0-50% linear gradient of acetonitrile over a 90-minute interval at a flow rate of 0.5 ml/min. Elution of peptides was detected by monitoring of absorbance at 210 nm and fluorescence at 550 nm with excitation at 350 nm. The fluorescent tracer peaks were collected and after concentration to smaller volumes (50-200 µl) were reinjected into the same column. The second round of elution was performed using a 10-20% or 20-35% linear gradient of acetonitrile over a 60-minute interval at a flow rate of 0.5 ml/min. The isolated dansyl-PGGQQIV-labeled peptides were subjected to mass spectral analysis.

Mass Spectral Analysis. The determination of molecular masses of the isolated peptides was performed using MALDI-TOF mass spectrometer Voyager DE-STR (Perseptive Biosystems, Foster City, Calif.). Ions formed by laser desorption at 337 nm ($N_2$ laser) were recorded at an acceleration voltage of 20 kV in the reflector mode. In general, 200 single spectra were accumulated for improving the signal/noise ratio and analyzed by the use of the Data Explorer software. Alpha-cyano-4-hydroxycinnamic acid (Aldrich Chemical Co., St. Louis, Mo.) was used as the matrix. One µl of a 10 mg/ml solution of the matrix compounds in 70% acetonitrile/0.1% trifluoroacetic acid was mixed with 1 µl peptide solution (5-10 pmole/µl). For MALDI-TOF MS, 1 µl of this mixture was spotted on a stainless steel sample target and dried at room temperature. The mass spectra were externally calibrated using human Glu1-fibrinopeptide B, human angiotensin I, and synthetic des-Arg1-bradykinin.

SDS-PAGE and Western Blot Analysis. SDS-PAGE was carried out using precast 3-8% Tris-Acetate gradient gels (Invitrogen, Carlsbad, Calif.). All SDS-polyacrylamide gels in this study were stained with Coomassie Brilliant Blue R (BioRad Laboratories, Hercules, Calif.). For Western Blot analysis protein samples were electroblotted to nitrocellulose membranes and immunostained with the corresponding rabbit polyclonal or mouse monoclonal antibody. The membranes were treated with goat anti-rabbit or anti-mouse alkaline phosphatase-conjugated secondary antibody and the alkaline phosphatase activity was developed with alkaline phosphatase conjugate substrate (BioRad Laboratories, Hercules, Calif.).

Activation of Factor XIII. Activation was achieved by treatment of 500 µg/ml of Factor XIII (Haematologic Technologies, Inc., Essex Junction, Vt.) with 0.25 U/ml of thrombin (Sigma, St. Louis, Mo.) in TBS, pH 7.4 buffer containing 10 mM dithiothreitol and 20 mM CaCl$_2$. After incubation for 20 min at 37° C., thrombin was inactivated by the addition of a molar excess of hirudin (Sigma, St. Louis, Mo.) and this mixture was used as factor XIIIa (Takagi et al. 1995).

Incorporation of Dansylcadaverine and Dansyl-PGGQ-QIV Probes. Activated Factor XIII was employed to incorporate dansylcadaverine (Sigma, St. Louis, Mo.) or dansyl-PGGQQIV (New England Peptide, Inc., Gardner, Mass.) in FnbA species. Dansylcadaverine was utilized to probe Factor XIIIa-reactive glutamines and the peptide dansyl-PGGQQIV was used to probe reactive lysines. Incorporation was carried out by incubating 2 μM of wild-type or mutated rFnbA with 30 μg/ml of Factor XIIIa in the presence of either 2 mM of dansylcadaverine or 2 mM of dansyl-PGGQQIV at 3° C. in 20 mM Tris, pH 7.4, 150 mM NaCl, 5 mM DTT, 5 mM CaCl$_2$ or 20 mM Tris, pH 8.5, 15 mM NaCl, 5 mM DTT, 5 mM CaCl$_2$, respectively. Control reactions were also performed in the same buffers containing 2 mM EDTA. At various times reactions were terminated by the addition of 2% SDS and 10% β-mercaptoethanol, heated at 95° C., and analyzed by SDS-PAGE. Gels were examined under ultraviolet light and then stained with Coomassie brilliant blue.

Cross-Linking to Fibrin. Fibrin polymerization and Factor XIIIa-catalyzed cross-linking of fibrin in the presence or absence of 2 μM of wild-type or mutated FnbA was initiated by the addition of 0.5 U/ml of thrombin to a solution containing 5 μM of human fibrinogen (Calbiochem, San Diego, Calif.) and 15 μg/ml of Factor XIII. Cross-linking reactions were carried out in TBS, pH 7.4 buffer containing 5 mM CaCl$_2$ at 37° C. At various times the reactions were terminated by the addition of 20 mM Tris, pH 7.2, 9 M urea, 40 mM dithiothreitol, 2% SDS. The clots were solubilized at 37° C. for 30 minutes, heated at 95° C., and samples were analyzed by SDS-PAGE/Western blotting.

Cross-Linking to Fibronectin. The cross-linking reaction with fibronectin was initiated by the addition of 15 μg/ml of activated Factor XIII to a solution containing 1 μM of wild-type or mutated FnbA and 2 μM of human plasma fibronectin (Sigma, St. Louis, Mo.). The reactions were carried out in TBS, pH 7.4 buffer containing 5 mM CaCl$_2$ at 37° C. At various times thereafter cross-linking reactions were terminated by the addition of 2% SDS and 10% β-mercaptoethanol, heated at 95° C., and analyzed by SDS-PAGE/Western blotting.

Kinetics of Cross-Linking. The kinetics of Factor XIIIa-mediated cross-linking of FnbA species to fibrin and fibronectin was examined by densitometric analysis of the gels stained with Coomassie brilliant blue. Laser densitometry was performed using a Personal Densitometer SI (Molecular Dynamics, Piscataway, N.J.). Each gel was scanned and the generated images were analyzed using ImageQuant 5.2 software. The rate of reactions was evaluated by the decrease of FnbA upon its cross-linking to fibrin or fibronectin. The relative amount of FnbA in the reaction mixture was determined using the area beneath the peak corresponding to the FnbA band and then plotted as a function of time.

Results

Incorporation of Dansylcadaverine and Dansyl-PGGQ-QIV Probes. The wild-type and mutated (IQ, 4Q4K) forms of FnbA comprising residues Ala1 through Pro839 (FIG. 7A) were produced in E coli using the pET-28a expression vector and isolated from the soluble fraction of bacterial lysate as described earlier (Matsuka et al. 2003). Each of the isolated proteins exhibited a single band on SDS-PAGE (FIG. 7B) and displayed a single NH$_2$-terminal sequence starting at ASE-QKTTTVE (set forth in SEQ ID NO:32). To examine if the replacement of identified Gln and Lys sites with Ala residues affected FnbA reactivity towards Factor XIIIa, a series of experiments were designed in which the wild-type and mutated forms (IQ and 4Q4K) of FnbA were tested as substrates for Factor XIIIa. Comparison of Factor XIIIa reactivity of the wild-type FnbA with that of the 1Q and 4Q4K FnbA mutants was initially performed using dansylcadaverine and dansyl-PGGQQIV probes (FIG. 8). At various times, aliquots of reaction mixtures with dansylcadaverine or dansyl-PGGQ-QIV were collected, analyzed by SDS-PAGE, and examined under ultraviolet light prior to staining with Coomassie blue. In the presence of Factor XIIIa and a molar excess of dansylcadaverine, the band corresponding to the wild-type FnbA undergoes a continual increase of fluorescence reflecting the enzymatic attachment of increasing molecules of the probe (FIG. 8A). Under the same experimental conditions, incorporation of dansylcadaverine into the 1Q FnbA mutant was drastically reduced, suggesting that Gln at position 103 indeed acts as a major reactive Gln site in FnbA. Further reduction in fluorescence intensity was observed with the 4Q4K rFnbA mutant in which all four identified reactive Gln residues (Gln 103, Gln 105, Gln783, and Gln 830) were replaced with Ala (FIG. 8A). Incubation of the 4Q4K FnbA mutant with dansylcadaverine and Factor XIIIa for 60 minutes, however, resulted in a weak but detectable incorporation of the probe (FIG. 8A). The residual reactivity of the 4Q4K FnbA mutant observed in the reaction with dansylcadaverine may indicate the presence in FnbA of an additional minor reactive Gln site(s).

Factor XIIIa-catalyzed incorporation of the dansyl-PGGQ-QIV probe into the wild-type FnbA is demonstrated in FIG. 8 B. When the 1Q FnbA mutant was assayed in the same reaction, its protein band exhibited fluorescence intensity that was slightly higher when compared with that of the wild-type FnbA (FIG. 8). This result suggests that substitution of the major reactive Gln103 with Ala resulted in a more efficient dansyl-PGGQQIV labeling of the Lys sites within the 1Q FnbA mutant. This effect is attributed to the high reactivity of the Gln103 site, which might effectively compete with the dansyl-PGGQQIV peptide probe by participating in intra- and/or intermolecular protein cross-linking. Occurrence of protein cross-linking upon incorporation of the dansyl-PG-GQQIV probe in the wild-type FnbA is supported by the presence of low mobility bands detectable under ultraviolet light and upon staining with Coomassie blue (FIG. 8 B). Factor XIIIa incorporated the dansyl-PGGQQIV probe in the 4Q4K FnbA mutant at a reduced rate and with lower efficiency, suggesting that mutated Lys157, Lys503, Lys620, and Lys762 serve as amine donor sites. It is apparent, however, that the overall reduction of Factor XIIIa reactivity observed with 4Q4K FnbA mutant towards dansyl-PGGQQIV probe was not as significant as it was towards dansylcadaverine. This indicates that additional reactive Lys site(s) remain available for enzymatic modification with the dansyl-PGGQ-QIV probe.

Factor XIIIa-Mediated Cross-Linking to Fibrin. Factor XIIIa reactivity of the 1Q and 4Q4K FnbA mutants was evaluated in a fibrin cross-linking reaction. In a control reaction, wild-type FnbA undergoes cross-linking to the fibrin α chain which results in the formation of high molecular mass heterocomplexes (Matsuka et al. 2003). Cross-linking was accompanied by the depletion of the band corresponding to the wild-type FnbA and by the appearance of a prominent band with an apparent molecular mass corresponding to the FnbA-α chain heterodimer (FIGS. 9 A, B, and C, band a). The products of cross-linking reaction (bands a, b, c, and d)

reacted with both anti-FnbA polyclonal antibody and anti-fibrinogen α chain monoclonal antibody (FIGS. 9 B and C), suggesting that these complexes are composed of covalently attached FnbA and fibrin α chain. Under the same experimental conditions, both FnbA mutants (1Q and 4Q4K) exhibited extremely low Factor XIIIa cross-linking reactivity. Only traces of FnbA mutant-α fibrin chain heterodimer were detected upon Coomassie blue staining (FIG. 9 A) or upon immunostaining with anti-FnbA polyclonal antibody (FIG. 9 B) and anti-fibrinogen α chain monoclonal antibody (FIG. 9 C). The consumption of the wild-type and mutated FnbA species upon incubation with fibrin and Factor XIIIa was evaluated using densitometric analysis (FIG. 10). As shown in FIG. 10, the wild-type FnbA reacted at a much higher rate than the 1Q or 4Q4K FnbA mutants. After 120 minutes of incubation, the amount of free (uncross-linked) 1Q or 4Q4K FnbA mutant remaining was about 85% more compared with that of the wild-type FnbA. These data suggest that the Gln site at position 103 is mostly responsible for Factor XIIIa-catalyzed attachment of FnbA to fibrin α chains. The obtained data also indicate that both the 1Q and 4Q4K FnbA mutants exhibit about 85% reduction of reactivity in cross-linking reaction with fibrin.

Factor XIIIa-Mediated Cross-Linking to Fibronectin. The reactivity of the 1Q and 4Q4K FnbA mutants was also tested in reactions with plasma fibronectin. For this purpose SDS-PAGE and Western blot analysis were again utilized to assay reactivity of the FnbA mutants. Upon incubation with fibronectin the bands corresponding to the wild-type or mutated forms of FnbA were steadily depleted as proteins became cross-linked into high-molecular mass heterocomplexes (FIGS. 11A, B, and C). Formation of covalently cross-linked high molecular mass complexes consisting of the wild-type or mutated FnbA and fibronectin was evident from the results of Western blot analysis using anti-FnbA polyclonal antibody (FIG. 11B) and anti-fibronectin monoclonal antibody (FIG. 11 C). Both SDS-PAGE and Western blot revealed little difference between reactivity of the wild-type and mutated FnbA species (FIG. 11). However, when the kinetics of the reaction was assayed using densitometric analysis the difference in the rate of cross-linking became apparent (FIG. 12). The 1Q FnbA mutant reacted at a rate close to that of the wild type FnbA, while the 4Q4K FnbA mutant exhibited a slower rate of cross-linking. After 360 minutes of incubation, the amount of free (uncross-linked) 4Q4K FnbA mutant remaining was about 35% less when compared with that of the wild-type FnbA or 1Q FnbA mutant. These data suggest that the Lys sites at positions 157, 503, 620, and 762 are involved in Factor XIIIa-mediated cross-linking of FnbA with fibronectin and totally contribute about 35% of the reactivity of FnbA. The data also indicate that additional unidentified reactive Lys residue(s) of FnbA are involved in cross-linking with fibronectin.

Identification of Lys 702 as an Additional Reactive Site in FnbA. The results of the labeling experiments with the dansyl-PGGQQIV probe and cross-linking with fibronectin suggest that additional reactive Lys site(s) remain available for Factor XIIIa in the 4Q4K FnbA mutant. As was reported earlier (U.S. patent application 60/573,724 and Anderson et al. 2004) for the identification of Factor XIIIa-reactive Lys sites, a procedure was employed that utilized labeling of FnbA with dansyl-PGGQQIV (Parameswaran et al. 1990; Lorand et al. (1992). Using dansyl-PGGQQIV as a fluorescent tracer we labeled FnbA with the probe, digested the modified protein with Glu-C proteinase and performed HPLC separation of labeled FnbA peptides. Subsequent mass spectral and $NH_2$-terminal sequence analysis of the isolated fluorescent peaks (tracer-containing peptides) resulted in the identification of all but one peak (designated as peak 3) (Anderson et al. 2004). To identify the additional reactive Lys site(s) in FnbA the material corresponding to fluorescent peak 3 was further purified using reversed phased HPLC and then subjected to mass spectral analysis. The analysis of the probe-modified material from peak 3 revealed the presence of a peptide with an observed mass $[M+H]^+$ of 1941.98 (FIG. 13). This value corresponds to a calculated mass of the 9-mer NSHVDIKSE peptide (set forth in SEQ ID NO:33) containing a single dansyl-PGGQQIV modification (Table 4). The NSHVDIKSE peptide is originated from the COOH-terminal region of FnbA and contains a single Lys residue at position 702. Therefore, Lys702 was identified as a probe-modified residue that is targeted by Factor XIIIa. Multiple sequence alignment of known FnbA and FnbB species from different *S. aureus* strains revealed that Lys702 is extremely conserved and present in all analyzed sequences (FIG. 14). The Lys702 site is situated in the region that is located between the Du and D1 fibronectin-binding repeats of FnbA (FIG. 7) and, therefore, should be readily available for cross-linking with Gln3 of fibronectin. Furthermore, the newly identified Lys702 along with reactive Lys620 (Anderson et al. 2004) are the only two Lys sites that are found in all analyzed FnbA and FnbB sequences. Both Lys620 (fluorescent peak 5, FIG. 11 D [7]) and Lys702 (fluorescent peak 3, FIG. 11D (Anderson et al. 2004)) sites also exhibited the highest reactivity toward the dansyl-PGGQQIV probe. The observed high reactivity of the newly identified Lys702 and its high degree of preservation in FnbA and FnbB sequences suggest the importance of this site for Factor XIIIa catalyzed cross-linking reactions.

It should be understood that the foregoing discussion and examples merely present a detailed description of certain embodiments. It therefore should be apparent to those of ordinary skill in the art that various modifications and equivalents can be made without departing from the spirit and scope of the invention.

All journal articles, other references, patents and patent applications that are identified in this patent application are incorporated by reference in their entirety.

REFERENCES

Matsuka et al. "*Staphylococcus aureus* Fibronectin-Binding Protein Serves as a Substrate for Coagulation Factor XIIIa: Evidence for Factor XIIIa-Catalyzed Covalent Cross-Linking to Fibronectin and Fibrin." *Biochemistry* 42, 14643-14652 (2003).

Aeschlimann, D. and Paulsson, M. "Transglutaminases: Protein Cross-Linking Enzymes in Tissues and Body Fluids." *Thrombosis and Haemostasis* 71, 402-415 (1994).

Gorman J. J. and Folk, J. E. "Structural features of glutamine substrates for transglutaminases: Specificities of human plasma factor XIIIa and guinea pig liver enzyme toward syntheticpeptides.". *J. Biol. Chem.* 256, 2712-2715 (1981).

Gorman J. J. and Folk, J. E. "Structural features of glutamine substrates for transglutaminases: Role of extended interactions in the specificity of human plasma factor XIIIa and guinea pig liver enzyme." *J. Biol. Chem.* 259, 9007-9010 (1984).

Fesus L., Metsis M. L., Muszbek L. and Koteliansky, V. E. "Transglutaminase-sensitive glutamine residues of human plasma fibronectin revealed by studying its proteolytic fragments." *Eur. J. Biochem.* 154, 371-374 (1986).

Henschen, A. and J. McDonagh. "Fibrinogen, fibrin and factor XIII." *Blood coagulation*. H. C. Hemker. Amsterdam, Elsevier science Publishers: 171-241 (1986).

Lorand, L. "Factor XIII: Structure, Activation, and Interactions with Fibrinogen and Fibrin." *Ann. N.Y. Acad. Sci.* 936: 291-311 (2001).

Lorand, L. and R. M. Graham. "Transglutaminases: Crosslinking Enzymes with Pleiotropic Functions." *Nature* 4: 140-156 (2003).

Signas, C., G. Raucci, et al. "Nucleotide sequence of the gene for a fibronectin-binding protein from *Staphylococcus aureus*: Use of this peptide sequence in the synthesis of biologically active peptides." *Proceedings of the National Academy of Sciences of the United States of America* 86: 699-703 (1989).

Schneewind, O., A. Fowler, et al. "Structure of the Cell Wall Anchor of Surface Proteins in *Staphylococcus aureus*." *Science* 268 (5207): 103-106 (1995).

Lorand, L., N. G. Rule, et al. (1968). "Amine Specificity in Transpeptidation. Inhibition of Fibrin Cross-Linking." *Biochemistry* 7: 1214-1223 (1968).

Lorand, L., G. E. Siefring, et al. "Dansylcadaverine Specific Staining for Transamidating Enzymes." *Analytical Biochemistry* 93: 453-458 (1979).

Parameswaran, K., P. Velasco, et al. "Labeling of ε-lysine crosslinking sites in proteins with peptide substrates of factor XIIIa and transglutaminase." *Proc. Natl. Acad. Sci. USA* 87: 8472-8475 (1990).

Lorand, L., K. Parameswaran, et al. "Biotinylated Peptides Containing a Factor XIIIa or Tissue Transglutaminase-Reactive Glutaminyl Residue That Block Protein Cross-linking Phenomena by Becoming Incorporated into Amine Donor Sites." *Bioconjugate Chem.* 3:37-41 (1992).

Sobel, J. H. and M. A. Gawinowicz. "Identification of the Alpha Chain Lysine Donor Sites Involved in Factor XIIIa Fibrin Cross-linking." *J. Biol. Chem.* 271: 19288-19297 (1996).

Cottrell, B. A., D. D. Strong, et al. "Amino acid sequence studies on the alpha-chain of human fibrinogen. Exact location of cross-linking acceptor sites." *Biochemistry* 18: 5405-5410 (1979).

McDonagh, R. P., J. McDonagh, et al. "Amino acid sequence of the factor XIIIa acceptor site in bovine plasma fibronectin." *FEBS Lett* 127: 174-178 (1981).

Matsuka, Y., L. Medved, et al. "Factor XIIIa-Catalyzed Cross-linking of Recombinant Alpha C Fragments of Human Fibrinogen." *Biochemistry* 35: 5810-5816 (1996).

House-Pompeo, K., Y. Xu, et al. "Conformational Changes in the Fibronectin Binding MSCRAMMs Are Induced by Ligand Binding." *J. Biol. Chem.* 271: 1379-1384 (1996).

Penkett, C. J., C. Redfield, et al. "NMR Analysis of Main-chain Conformational Preferences in an Unfolded Fibronectin-binding Protein." *J. Mol. Biol.* 274: 152-159 (1997).

Penkett, C. J., C. Redfield, et al. "Structural and Dynamical Characterization of a Biologically Active Unfolded Fibronectin-Binding Protein from *Staphylococcus aureus*." *Biochemistry* 37: 17054-17067 (1998).

Grootjans, J. J., P. J. T. A. Groenen, et al. "Substrate Requirements for Transglutaminases. Influence of the Amino Acid Residue Preceding the Amine Donor." *J. Biol. Chem.* 270: 22855-22858 (1995).

Jonsson, K., C. Signas, et al. "Two different genes encode fibronectin-binding proteins in *Staphylococcus aureus*: the complete nucleotide sequence and characterization of the second gene." *Eur. J. Biochem.* 202: 1041-1048 (1991).

Baba, T., Takeuchi, F., Yuzawa, H., Aoki, K., Oguchi, A. Nagai, Y., Iwama, N., Asano, K., Naimi, T., Kuroda, H., Cui, L., Yamamoto, K., and Hiramatsu, K. "Genome and virulence determinants of high virulence community-acquired MRSA" *The Lancet* 359, p. 1819-1827 (2002).

Kuroda, M., T. Ohta, et al. "Whole genome sequencing of meticillin-resistant *Staphylococcus aureus*." *The Lancet* 357: 1225-1240 (2001).

Thompson J. D., Higgins, D. G., Gibson, T. J. "CLUSTAL W: improving the sensitivity of progressive multiple sequence alignment through sequence weighting, position-specific gap penalties and weight matrix choice." *Nucleic Acids Research* 22, p. 4673-4680 (1994).

Mosesson, M. W. (1992). "The roles of fibrinogen and fibrin in hemostasis and thrombosis." *Semin. Hematol.* 29: 177-188 (1992).

Grinnel, F., M. Feld, et al. "Fibroblast Adhesion to Fibrinogen and Fibrin Substrata: Requirement for Cold-Insoluble Globulin (Plasma Fibronectin)." *Cell* 19: 517-525 (1980).

Knox, P., S. Crooks, et al. "Role of Fibronectin in the Migration of Fibroblasts into Plasma Clots." *The Journal of Cell Biology* 102: 2318-2323 (1986).

Corbett, S. A., L. Lee, et al. "Covalent Cross-linking of Fibronectin to Fibrin Is Required for Maximal Cell Adhesion to a Fibronectin-Fibrin Matrix." *J. Biol. Chem.* 272: 24999-25005 (1997).

Matsuka, Y. V., L. V. Medved, et al. "The N-terminal Fibrin-binding Site of Fibronectin Is Formed by Interacting Fourth and Fifth Finger Domains." *The Journal of Biological Chemistry.* 269 (13): 9539-9546 (1994).

Matsuka, Y., M. Migliorini, et al. "Cross-Linking of Fibronectin to C-Terminal Fragments of the Fibrinogen α-Chain by Factor XIIIa." *J Prot Chem* 16: 739-745 (1997).

U.S. Pat. No. 5,320,951

U.S. Pat. No. 5,571,514

U.S. Pat. No. 5,175,096

U.S. Pat. No. 5,652,217

Cunningham and Wells, *Science* 244:1081-1085 (1989).

Bowie et al., *Science* 247:1306-1310 (1990).

*Current Protocols in Molecular Biology*, John Wiley & Sons, NY, 6.3.1-6.3.6 (1989).

Goeddel, *Gene Expression Technology: Methods in Enzymology* 185, Academic Press, San Diego, Calif. (1990).

Broach, et al., *Experimental Manipulation of Gene Expression*, ed. M. Inouye, Academic Press (1983), p. 83.

Sambrook et al., *Molecular Cloning: A Laboratory Manual*, $2^{nd}$ ed., Cold Spring Harbor Laboratory Press (1989), Chapters 16 and 17.

Wong, *Chemistry of Protein Conjugation*, CRC Press, Ann Arbor Mich. (1991).

Bernatowicz and Matsueda, *Analytical Biochemistry* 155:95-102 (1986).

Frisch et al., *Bioconjugate Chem.* 7:180-186 (1996).

Boeckler et al., *J. Immunological Methods* 191:1-10 (1996).

Maniatis et al., *Molecular Cloning: A Laboratory Manual*, $2^{nd}$ ed., Cold Spring Harbor Laboratory Press (1989).

WO 96/21356

U.S. Pat. No. 5,593,972

Takagi, J., T. Aoyama, et al. "Identification of factor-XIIIa-reactive glutaminyl residues in the propolypeptide of bovine von Willebrand factor." *Eur. J. Biochem.* 232:773-777 (1995).

Clement, S., P. T. Velasco, et al. "The intermediate filament protein, vimentin, in the lens is a target for cross-linking by transglutaminase." *J Biol Chem* 273 (13): 7604-9 (1998).

F. D. Lowy, *The New England Journal of Medicine* 339: 520-532 (1998).

J. M. Patti, B. L. Allen, M. J. McGavin and M. Hook, *Annu. Rev. Microbiol.* 48:585-617 (1994).

R. A. S. Ariens, T.-S. Lai, J. W. Weisel, C. S. Greenberg and P. J. Grant, *Blood* 100: 743-754 (2002).

E. T. Anderson, L. Fletcher, A. Severin, E. Murphy, S. M. Baker and Y. V. Matsuka, *Biochemistry* 43:11842-11852 (2004).

TABLE 1

Factor XIII Substrates

| Substrate | Cross-linking site | Substances with which it is cross-linked | Known or potential function |
|---|---|---|---|
| Fibrin(ogen) γ-chain[52-54] | Gln398, Gln399, and Lys406 | Itself and α-chain | Clot stabilization |
| Fibrin(ogen) α-chain[58-62] | Gln221, Gln237, Gln328, Gln366, and 15 potential lysines from Lys208 to Lys606 | Itself and γ-chain | Clot stabilization |
| α2-Antiplasmin[67-80] | Gln2 | Lys303, fibrin α-chain | Resistance to fibrinolysis |
| TAFI[150] | Gln2, Gln5, Gln292 | Fibrin, itself | Resistance to fibrinolysis |
| PAI-2[151,152] | — | Lys148, Lys230, Lys413 fibrin α-chain | Resistance to fibrinolysis |
| Fibronectin[72,73] | Gln3 | Itself, fibrin, collagen | Migration of calls into the clot; wound healing |
| Collagen[72,80] | — | Fibronectin, fibrin | Stabilization of extracellular matrix |
| Von Willebrand factor[153,154] | — | Fibrin, collagen | Platelet adhesion to the clot |
| Vitronectin[155,156] | Gln93 | — | — |
| Thrombospondin[157] | — | Fibrin | — |
| Factor V[158,159] | — | Fibrin, platelets | Increased thrombin generation at the clot surface |
| Actin[160,161] | — | Fibrin | Clot retraction, stabilization of the platelet cytoskeleton |
| Myosin[162] | — | Itself | Clot retraction, stabilization of the platelet cytoskeleton |
| Vinculin[163] | — | Fibrin | Clot retraction, stabilization of the platelet cytoskeleton |
| $α_{IIb}β_3$[164] | — | Fibrin | Stabilization of the platelet-fibrin clot |

TAFI indicates thrombin-activatable fibrinolysis inhibitor,
PAI-2, plasminogen activator inhibitor 2.

Ariens, R. A. et al. *Blood* (2002) 100, 743-754

TABLE 2

Summary of the NH$_2$-terminal sequence and mass-spectral analysis of dansylcadaverine-modified peptides derived from rFnbA.

| Proteinease | Peak | Retention time (min) | Amino acid sequence | Peptide fragment | Observed mass (m/z) | Calculated mass (Da) |
|---|---|---|---|---|---|---|
| Trypsin | 1 | 43.84 | ETTQSQDNSGD[Q]R | 92-104 | 1783.83 | 1783.07 |
|  | 3 | 64.52 | [Q]VDLIPK | 105-111 | 1130.68 | 1129.94 |
| Glu-C | 1 | 46.75 | TTQSQDNSGD[Q]RQVD | 93-107 | 1996.82 | 1996.18 |
|  | 4 | 53.02 | G[Q]QTIEE | 829-835 | 1122.50 | 1121.83 |
|  | 6 | 58.63 | SVP[Q]IHGFNKHNE | 780-792 | 1825.01 | 1824.20 |
|  | 7 | 60.29 | TTQSQDNSGD[Q]R[Q]VD | 93-107 | 2316.05 | 2314.64 |

[Q] - Indicates an Edman cycle without recovery of a known amino acid and assigned to be factor XIIIa-derivatized Gln. The calculated mass of tryptic peptides 1 and 3, and Glu-C proteinase peptides 1, 4, and 6 include the mass of one incorporated dansylcadaverine molecule. The calculated mass of Glu-C proteinase peptide 7 includes the mass of two incorporated dansylcadaverine molecules (see Materials and Methods). Tryptic peptide from fluorescent peak 2 and Glu-C proteinase peptides from fluorescent peaks 2, 3, and 5 were not positively identified.

TABLE 3

Summary of the NH$_2$-terminal sequence and mass-spectral analysis of dansyl-PGGQQIV-modified peptides derived from rFnbA.

| Proteinease | Peak | Retention time (min) | Amino acid sequence | Peptide fragment | Observed mass (m/z) | Calculated mass (Da) |
|---|---|---|---|---|---|---|
| Glu-C | 1 | 57.18 | V[K]GTD | 156-160 | 1432.37 | 1432.51 |
|  | 2 | 58.55 | [K]DKPKYE | 762-768 | 1820.22 | 1821.44 |
|  | 4 | 60.24 | V[K]GTDVTSKVTVE | 156-168 | 2276.73 | 2276.70 |
|  | 5 (*) | 62.29 | ST[K]GIVTGAVSD | 618-629 | 2047.97 | 2048.55 |

TABLE 3-continued

Summary of the NH₂-terminal sequence and mass-spectral analysis
of dansyl-PGGQQIV-modified peptides derived from rFnbA.

| Proteinease | Peak | Retention time (min) | Amino acid sequence | Peptide fragment | Observed mass (m/z) | Calculated mass (Da) |
|---|---|---|---|---|---|---|
|  | 6 | 62.98 | ST[K]GIVTGAVSDHTTVE | 618-634 | 2614.83 | 2615.82 |
|  | 7 | 63.77 | A[K]QIIE | 502-507 | 1614.23 | 1615.37 |

[K] - Indicates an Edman cycle without recovery of a known amino acid and assigned to be Factor XIIIa-derivatized Lys. The calculated mass includes the mass of one incorporated dansyl-PGGQQIV molecule (see Materials and Methods). Peptide from fluorescent peak 3 was not positively identified.

TABLE 4

Mass-spectral analysis of dansyl-PGGQQIV-modified
peptide derived from rFnbA by Glu-C proteinase.

| Peak | Retention time (min) | Amino acid sequence | Peptide fragment | Observed [M + H]⁺ | Calculated [M + H]⁺ |
|---|---|---|---|---|---|
| 3 | 59.46 | NSHVDIKSE | 696-704 | 1941.98 | 1941.90 |

The calculated mass includes the mass of one incorporated dansyl-PGGQQIV molecule (see Materials and Methods).

What is claimed is:

1. An isolated, altered *Staphylococcus aureus* (*S. aureus*) fibronectin-binding protein A (FnbA), wherein the alteration is a substitution of glutamine (Gln) 103 in FnbA of *S. aureus* having the amino acid sequence set forth in SEQ ID NO: 1.

2. The isolated, altered FnbA of claim 1, further comprising a substitution at each of residues Gln105, Lys157, Lys503, Lys620, Lys702, Lys762, Gln783 and Gln830.

3. An immunogenic composition comprising a physiologically acceptable vehicle and an isolated, altered *S. aureus* fibronectin-binding protein A (FnbA), wherein the alteration is a substitution of Gln103 in FnbA of *S. aureus* of having the amino acid sequence set forth in SEQ ID NO:1.

4. The immunogenic composition of claim 3, further comprising an adjuvant.

5. The immunogenic composition of claim 3, wherein the isolated, altered *S. aureus* FnbA further comprises a substitution at each of Gln105, Lys157, Lys503, Lys620, Lys702, Lys762, Gln783 and Gln830 of the FnbA of *S. aureus* having the amino acid sequence set forth in SEQ ID NO:1.

6. The immunogenic composition of claim 5, further comprising an adjuvant.

7. A method of inducing an immune response in a vertebrate against *S. aureus*, comprising administering to the vertebrate a composition comprising a physiologically acceptable vehicle and an immunologically effective amount of an isolated, altered FnbA of *S. aureus*, wherein the alteration is a substitution of Gln103 in FnbA of *S. aureus* having the amino acid sequence set forth in SEQ ID NO: 1.

8. The method of claim 7, wherein the vertebrate is a seronegative human.

9. A method of inducing an immune response in a vertebrate against *S. aureus*, comprising administering to the vertebrate a composition comprising a physiologically acceptable vehicle and an immunologically effective amount of an isolated, altered FnbA of *S. aureus*, wherein the alteration is a substitution of Gln103, Gln105, Lys157, Lys503, Lys620, Lys702, Lys762, Gln783 and Gln830 in FnbA of *S. aureus* having the amino acid sequence set forth in SEQ ID NO:1.

10. The method of claim 9, wherein the vertebrate is a seronegative human.

* * * * *

SEQUENCE LISTING

<160> NUMBER OF SEQ ID NOS: 33

<210> SEQ ID NO 1
<211> LENGTH: 839
<212> TYPE: PRT
<213> ORGANISM: Staphylococcus aureus

<400> SEQUENCE: 1

```
Ala Ser Glu Gln Lys Thr Thr Thr Val Glu Glu Asn Gly Asn Ser Thr
 1               5                  10                  15

Thr Asp Asn Lys Val Ser Glu Thr Gln Thr Thr Thr Asn Val Asn
                20                  25                  30

His Ile Glu Glu Thr Gln Ser Tyr Asn Ala Thr Val Thr Glu Gln Pro
            35                  40                  45

Ser Asn Ala Thr Gln Val Thr Thr Glu Glu Ala Pro Lys Ala Val Gln
        50                  55                  60

Ala Pro Gln Thr Ala Gln Pro Ala Asn Val Glu Lys Val Lys Glu Glu
65                  70                  75                  80

Val Val Lys Glu Glu Ala Lys Pro Gln Val Lys Glu Thr Thr Gln Ser
                85                  90                  95

Gln Asp Asn Ser Gly Asp Gln Arg Gln Val Asp Leu Ile Pro Lys Lys
            100                 105                 110

Ala Thr Gln Asn Gln Val Ala Glu Thr Gln Val Glu Val Ala Gln Pro
        115                 120                 125

Arg Thr Val Ser Glu Ser Lys Pro Arg Val Thr Arg Ser Ala Asp Val
    130                 135                 140

Val Glu Ala Lys Glu Gly Met Gly Val Ser Glu Val Lys Gly Thr Asp
145                 150                 155                 160

Val Thr Ser Lys Val Thr Val Glu Ser Gly Ser Ile Glu Ala Pro Gln
                165                 170                 175

Gly Asn Lys Val Glu Pro His Ala Gly Gln Arg Val Val Leu Lys Tyr
            180                 185                 190
```

-continued

```
Lys Leu Lys Phe Ala Asp Gly Leu Lys Arg Gly Asp Tyr Phe Asp Phe
        195                 200                 205

Thr Leu Ser Asn Asn Val Asn Thr Tyr Gly Val Ser Thr Ala Arg Lys
        210                 215                 220

Val Pro Glu Ile Lys Asn Gly Ser Val Val Met Ala Thr Gly Glu Ile
225                 230                 235                 240

Leu Gly Asn Gly Asn Ile Arg Tyr Thr Phe Thr Asn Glu Ile Glu His
                245                 250                 255

Lys Val Glu Val Thr Ala Asn Leu Glu Ile Asn Leu Phe Ile Asp Pro
            260                 265                 270

Lys Thr Val Gln Ser Asp Gly Glu Gln Lys Ile Thr Ser Lys Leu Asn
        275                 280                 285

Gly Glu Glu Thr Glu Lys Thr Ile Pro Val Val Tyr Asn Pro Gly Val
        290                 295                 300

Ser Asn Ser Tyr Thr Asn Val Asn Gly Ser Ile Glu Thr Phe Asn Lys
305                 310                 315                 320

Glu Ser Asn Lys Phe Thr His Ile Ala Tyr Ile Lys Pro Met Asn Gly
                325                 330                 335

Asn Gln Ser Asn Thr Val Ser Val Thr Gly Thr Leu Thr Glu Gly Ser
            340                 345                 350

Asn Leu Ala Gly Gly Gln Pro Thr Val Lys Val Tyr Glu Tyr Leu Gly
        355                 360                 365

Lys Lys Asp Glu Leu Pro Gln Ser Val Tyr Ala Asn Thr Ser Asp Thr
        370                 375                 380

Asn Lys Phe Lys Asp Val Thr Asn Glu Met Asn Gly Lys Leu Ser Val
385                 390                 395                 400

Gln Asp Asn Gly Ser Tyr Ser Leu Asn Leu Asp Lys Leu Asp Lys Thr
                405                 410                 415

Tyr Val Ile His Tyr Thr Gly Glu Tyr Leu Gln Gly Ser Asp Gln Val
            420                 425                 430

Asn Phe Arg Thr Glu Leu Tyr Gly Tyr Pro Glu Arg Ala Tyr Lys Ser
        435                 440                 445

Tyr Tyr Val Tyr Gly Gly Tyr Arg Leu Thr Trp Asp Asn Gly Leu Val
450                 455                 460

Leu Tyr Ser Asn Lys Ala Asp Gly Asn Gly Lys Asn Gly Gln Ile Ile
465                 470                 475                 480

Gln Asn Asn Asp Phe Glu Tyr Lys Glu Asp Thr Ala Lys Gly Thr Met
                485                 490                 495

Ser Gly Gln Tyr Asp Ala Lys Gln Ile Ile Glu Thr Glu Glu Asn Gln
            500                 505                 510

Asp Asn Thr Pro Leu Asp Ile Asp Tyr His Thr Ala Ile Asp Gly Glu
        515                 520                 525

Gly Gly Tyr Val Asp Gly Tyr Ile Glu Thr Ile Glu Glu Thr Asp Ser
        530                 535                 540

Ser Ala Ile Asp Ile Asp Tyr His Thr Ala Val Asp Ser Glu Ala Gly
545                 550                 555                 560

His Val Gly Gly Tyr Thr Glu Ser Ser Glu Glu Ser Asn Pro Ile Asp
                565                 570                 575

Phe Glu Glu Ser Thr His Glu Asn Ser Lys His His Ala Asn Val Val
            580                 585                 590

Glu Tyr Glu Glu Asp Thr Asn Pro Gly Gly Gly Gln Val Thr Thr Glu
        595                 600                 605
```

```
Ser Asn Leu Val Glu Phe Asp Glu Glu Ser Thr Lys Gly Ile Val Thr
        610                 615                 620

Gly Ala Val Ser Asp His Thr Thr Val Glu Asp Thr Lys Glu Tyr Thr
625                 630                 635                 640

Thr Glu Ser Asn Leu Ile Glu Leu Val Asp Glu Leu Pro Glu Glu His
                645                 650                 655

Gly Gln Ala Gln Gly Pro Ile Glu Glu Ile Thr Glu Asn Asn His His
            660                 665                 670

Ile Ser His Ser Gly Leu Gly Thr Glu Asn Gly His Gly Asn Tyr Gly
        675                 680                 685

Val Ile Glu Glu Ile Glu Glu Asn Ser His Val Asp Ile Lys Ser Glu
690                 695                 700

Leu Gly Tyr Glu Gly Gly Gln Asn Ser Gly Asn Gln Ser Phe Glu Glu
705                 710                 715                 720

Asp Thr Glu Glu Asp Lys Pro Lys Tyr Glu Gln Gly Gly Asn Ile Val
                725                 730                 735

Asp Ile Asp Phe Asp Ser Val Pro Gln Ile Gln Gly Gln Asn Asn Gly
            740                 745                 750

Asn Gln Ser Phe Glu Glu Asp Thr Glu Lys Asp Lys Pro Lys Tyr Glu
        755                 760                 765

Gln Gly Gly Asn Ile Ile Asp Ile Asp Phe Asp Ser Val Pro Gln Ile
770                 775                 780

His Gly Phe Asn Lys His Asn Glu Ile Ile Glu Glu Asp Thr Asn Lys
785                 790                 795                 800

Asp Lys Pro Asn Tyr Gln Phe Gly His Asn Ser Val Asp Phe Glu
                805                 810                 815

Glu Asp Thr Leu Pro Lys Val Ser Gly Gln Asn Glu Gly Gln Gln Thr
            820                 825                 830

Ile Glu Glu Asp Thr Thr Pro
        835

<210> SEQ ID NO 2
<211> LENGTH: 1038
<212> TYPE: PRT
<213> ORGANISM: Staphylococcus aureus

<400> SEQUENCE: 2

Val Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala Ser Glu Gln Lys Thr Thr Thr Val Glu Glu Asn
        35                  40                  45

Gly Asn Ser Ala Thr Asp Asn Lys Thr Ser Glu Thr Gln Thr Thr Ala
    50                  55                  60

Thr Asn Val Asn His Ile Glu Thr Gln Ser Tyr Asn Ala Thr Val
65                  70                  75                  80

Thr Glu Gln Pro Ser Asn Ala Thr Gln Val Thr Thr Glu Glu Ala Pro
                85                  90                  95

Lys Ala Val Gln Ala Pro Gln Thr Ala Gln Pro Ala Asn Val Glu Thr
            100                 105                 110

Val Lys Glu Glu Glu Lys Pro Gln Val Lys Glu Thr Thr Gln Pro Gln
        115                 120                 125

Asp Asn Ser Gly Asn Gln Arg Gln Val Asp Leu Thr Pro Lys Lys Val
    130                 135                 140
```

-continued

```
Thr Gln Asn Gln Gly Thr Glu Thr Gln Val Glu Val Ala Gln Pro Arg
145                 150                 155                 160

Thr Ala Ser Glu Ser Lys Pro Arg Val Thr Arg Ser Ala Asp Val Ala
            165                 170                 175

Glu Ala Lys Glu Ala Ser Asp Val Ser Glu Val Lys Gly Thr Asp Val
        180                 185                 190

Thr Ser Lys Val Thr Val Glu Ser Gly Ser Ile Glu Ala Pro Gln Gly
    195                 200                 205

Asn Lys Val Glu Pro His Ala Gly Gln Arg Val Leu Lys Tyr Lys
210                 215                 220

Leu Lys Phe Ala Asp Gly Leu Lys Arg Gly Asp Tyr Phe Asp Phe Thr
225                 230                 235                 240

Leu Ser Asn Asn Val Asn Thr Tyr Gly Val Ser Thr Ala Arg Lys Val
                245                 250                 255

Pro Glu Ile Lys Asn Gly Ser Val Val Met Ala Thr Gly Glu Ile Leu
            260                 265                 270

Gly Asn Gly Asn Ile Arg Tyr Thr Phe Thr Asn Glu Ile Glu His Lys
        275                 280                 285

Val Glu Val Thr Ala Asn Leu Glu Ile Asn Leu Phe Ile Asp Pro Lys
    290                 295                 300

Thr Val Gln Ser Asn Gly Glu Gln Lys Ile Thr Ser Lys Leu Asn Gly
305                 310                 315                 320

Glu Glu Thr Glu Lys Thr Ile Pro Val Val Tyr Asn Pro Gly Val Ser
                325                 330                 335

Asn Ser Tyr Thr Asn Val Asn Gly Ser Ile Glu Thr Phe Asn Lys Glu
            340                 345                 350

Ser Asn Lys Phe Thr His Ile Ala Tyr Ile Lys Pro Met Asn Gly Asn
        355                 360                 365

Gln Ser Asn Thr Val Ser Val Thr Gly Thr Leu Thr Glu Gly Ser Asn
    370                 375                 380

Leu Ala Gly Gly Gln Pro Thr Val Lys Val Tyr Glu Tyr Leu Gly Lys
385                 390                 395                 400

Lys Asp Glu Leu Pro Gln Ser Val Tyr Ala Asn Thr Ser Asp Thr Asn
                405                 410                 415

Lys Phe Lys Asp Val Thr Lys Glu Met Asn Gly Lys Leu Ser Val Gln
            420                 425                 430

Asp Asn Gly Ser Tyr Ser Leu Asn Leu Asp Lys Leu Asp Lys Thr Tyr
        435                 440                 445

Val Ile His Tyr Thr Gly Glu Tyr Leu Gln Gly Ser Asp Gln Val Asn
    450                 455                 460

Phe Arg Thr Glu Leu Tyr Gly Tyr Pro Glu Arg Ala Tyr Lys Ser Tyr
465                 470                 475                 480

Tyr Val Tyr Gly Gly Tyr Arg Leu Thr Trp Asp Asn Gly Leu Val Leu
                485                 490                 495

Tyr Ser Asn Lys Ala Asp Gly Asn Gly Lys Asn Gly Gln Ile Ile Gln
            500                 505                 510

Asp Asn Asp Phe Glu Tyr Lys Glu Asp Thr Ala Lys Gly Thr Met Ser
        515                 520                 525

Gly Gln Tyr Asp Ala Lys Gln Ile Ile Glu Thr Glu Asn Gln Asp
    530                 535                 540

Asn Thr Pro Leu Asp Ile Asp Tyr His Thr Ala Ile Asp Gly Glu Gly
545                 550                 555                 560
```

-continued

```
Gly Tyr Val Asp Gly Tyr Ile Glu Thr Ile Glu Thr Asp Ser Ser
                565                 570                 575

Ala Ile Asp Ile Asp Tyr His Thr Ala Val Asp Ser Glu Val Gly His
            580                 585                 590

Val Gly Gly Tyr Thr Glu Ser Ser Glu Glu Ser Asn Pro Ile Asp Phe
            595                 600                 605

Glu Glu Ser Thr His Glu Asn Ser Lys His His Ala Asp Val Val Glu
610                 615                 620

Tyr Glu Glu Asp Thr Asn Pro Gly Gly Gln Val Thr Thr Glu Ser
625                 630                 635                 640

Asn Leu Val Glu Phe Asp Glu Ser Thr Lys Gly Ile Val Thr Gly
            645                 650                 655

Ala Val Ser Asp His Thr Thr Ile Glu Asp Thr Lys Glu Tyr Thr Thr
            660                 665                 670

Glu Ser Asn Leu Ile Glu Leu Val Asp Glu Leu Pro Glu Glu His Gly
            675                 680                 685

Gln Ala Gln Gly Pro Ile Glu Glu Ile Thr Glu Asn Asn His His Ile
690                 695                 700

Ser His Ser Gly Leu Gly Thr Glu Asn Gly His Gly Asn Tyr Gly Val
705                 710                 715                 720

Ile Glu Glu Ile Glu Glu Asn Ser His Val Asp Ile Lys Ser Glu Leu
                725                 730                 735

Gly Tyr Glu Gly Gly Gln Asn Ser Gly Asn Gln Ser Phe Glu Glu Asp
            740                 745                 750

Thr Glu Glu Asp Lys Pro Lys Tyr Glu Gln Gly Gly Asn Ile Val Asp
            755                 760                 765

Ile Asp Phe Asp Ser Val Pro Gln Ile His Gly Gln Asn Lys Gly Asp
            770                 775                 780

Gln Ser Phe Glu Glu Asp Thr Glu Lys Asp Lys Pro Lys Tyr Glu His
785                 790                 795                 800

Gly Gly Asn Ile Ile Asp Ile Asp Phe Asp Ser Val Pro Gln Ile His
                805                 810                 815

Gly Phe Asn Lys His Asn Glu Ile Ile Glu Glu Asp Thr Asn Lys Asp
            820                 825                 830

Lys Pro Asn Tyr Gln Phe Gly Gly His Asn Ser Val Asp Phe Glu Glu
            835                 840                 845

Asp Thr Leu Pro Lys Val Ser Gly Gln Asn Glu Gly Gln Gln Thr Ile
850                 855                 860

Glu Glu Asp Thr Thr Pro Pro Thr Pro Pro Thr Pro Glu Val Pro Ser
865                 870                 875                 880

Glu Pro Glu Thr Pro Met Pro Pro Thr Pro Glu Val Pro Ser Glu Pro
                885                 890                 895

Glu Thr Pro Thr Pro Pro Thr Pro Glu Val Pro Ser Glu Pro Glu Thr
            900                 905                 910

Pro Thr Pro Pro Thr Pro Glu Val Pro Ser Glu Pro Glu Thr Pro Thr
            915                 920                 925

Pro Pro Thr Pro Glu Val Pro Ser Glu Pro Glu Thr Pro Thr Pro Pro
            930                 935                 940

Thr Pro Glu Val Pro Ala Glu Pro Gly Lys Pro Val Pro Pro Ala Lys
945                 950                 955                 960

Glu Glu Pro Lys Lys Pro Ser Lys Pro Val Glu Gln Gly Lys Val Val
                965                 970                 975

Thr Pro Val Ile Glu Ile Asn Glu Lys Val Lys Ala Val Ala Pro Thr
```

-continued

```
                980                 985                 990
Lys Lys Ala Gln Ser Lys Ser Glu Leu Pro Glu Thr  Gly Gly Glu
        995                 1000                1005

Glu Ser  Thr Asn Lys Gly Met  Leu Phe Gly Gly Leu  Phe Ser Ile
        1010                1015                1020

Leu Gly  Leu Ala Leu Leu Arg  Arg Asn Lys Lys Asn  Asn Lys Ala
        1025                1030                1035

<210> SEQ ID NO 3
<211> LENGTH: 1038
<212> TYPE: PRT
<213> ORGANISM: Staphylococcus aureus

<400> SEQUENCE: 3

Val Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala Ala Ser Glu Gln Lys Thr Thr Thr Val Glu Glu Asn
        35                  40                  45

Gly Asn Ser Ala Thr Asp Asn Lys Thr Ser Glu Thr Gln Thr Thr Ala
    50                  55                  60

Thr Asn Val Asn His Ile Glu Glu Thr Gln Ser Tyr Asn Ala Thr Val
65                  70                  75                  80

Thr Glu Gln Pro Ser Asn Ala Thr Gln Val Thr Thr Glu Glu Ala Pro
                85                  90                  95

Lys Ala Val Gln Ala Pro Gln Thr Ala Gln Pro Ala Asn Val Glu Thr
            100                 105                 110

Val Lys Glu Glu Glu Lys Pro Gln Val Lys Glu Thr Thr Gln Pro Gln
        115                 120                 125

Asp Asn Ser Gly Asn Gln Arg Gln Val Asp Leu Thr Pro Lys Lys Val
    130                 135                 140

Thr Gln Asn Gln Gly Thr Glu Thr Gln Val Glu Val Ala Gln Pro Arg
145                 150                 155                 160

Thr Ala Ser Glu Ser Lys Pro Arg Val Thr Arg Ser Ala Asp Val Ala
                165                 170                 175

Glu Ala Lys Glu Ala Ser Asp Val Ser Glu Val Lys Gly Thr Asp Val
            180                 185                 190

Thr Ser Lys Val Thr Val Glu Ser Gly Ser Ile Glu Ala Pro Gln Gly
        195                 200                 205

Asn Lys Val Glu Pro His Ala Gly Gln Arg Val Val Leu Lys Tyr Lys
    210                 215                 220

Leu Lys Phe Ala Asp Gly Leu Lys Arg Gly Asp Tyr Phe Asp Phe Thr
225                 230                 235                 240

Leu Ser Asn Asn Val Asn Thr Tyr Gly Val Ser Thr Ala Arg Lys Val
                245                 250                 255

Pro Glu Ile Lys Asn Gly Ser Val Val Met Ala Thr Gly Glu Ile Leu
            260                 265                 270

Gly Asn Gly Asn Ile Arg Tyr Thr Phe Thr Asn Glu Ile Glu His Lys
        275                 280                 285

Val Glu Val Thr Ala Asn Leu Glu Ile Asn Leu Phe Ile Asp Pro Lys
    290                 295                 300

Thr Val Gln Ser Asn Gly Glu Gln Lys Ile Thr Ser Lys Leu Asn Gly
305                 310                 315                 320
```

```
Glu Glu Thr Glu Lys Thr Ile Pro Val Val Tyr Asn Pro Gly Val Ser
            325                 330                 335

Asn Ser Tyr Thr Asn Val Asn Gly Ser Ile Glu Thr Phe Asn Lys Glu
            340                 345                 350

Ser Asn Lys Phe Thr His Ile Ala Tyr Ile Lys Pro Met Asn Gly Asn
            355                 360                 365

Gln Ser Asn Thr Val Ser Val Thr Gly Thr Leu Thr Glu Gly Ser Asn
        370                 375                 380

Leu Ala Gly Gly Gln Pro Thr Val Lys Val Tyr Glu Tyr Leu Gly Lys
385                 390                 395                 400

Lys Asp Glu Leu Pro Gln Ser Val Tyr Ala Asn Thr Ser Asp Thr Asn
                405                 410                 415

Lys Phe Lys Asp Val Thr Lys Glu Met Asn Gly Lys Leu Ser Val Gln
            420                 425                 430

Asp Asn Gly Ser Tyr Ser Leu Asn Leu Asp Lys Leu Asp Lys Thr Tyr
            435                 440                 445

Val Ile His Tyr Thr Gly Glu Tyr Leu Gln Gly Ser Asp Gln Val Asn
        450                 455                 460

Phe Arg Thr Glu Leu Tyr Gly Tyr Pro Glu Arg Ala Tyr Lys Ser Tyr
465                 470                 475                 480

Tyr Val Tyr Gly Gly Tyr Arg Leu Thr Trp Asp Asn Gly Leu Val Leu
                485                 490                 495

Tyr Ser Asn Lys Ala Asp Gly Asn Gly Lys Asn Gly Gln Ile Ile Gln
            500                 505                 510

Asp Asn Asp Phe Glu Tyr Lys Glu Asp Thr Ala Lys Gly Thr Met Ser
            515                 520                 525

Gly Gln Tyr Asp Ala Lys Gln Ile Ile Glu Thr Glu Asn Gln Asp
        530                 535                 540

Asn Thr Pro Leu Asp Ile Asp Tyr His Thr Ala Ile Asp Gly Glu Gly
545                 550                 555                 560

Gly Tyr Val Asp Gly Tyr Ile Glu Thr Ile Glu Glu Thr Asp Ser Ser
                565                 570                 575

Ala Ile Asp Ile Asp Tyr His Thr Ala Val Asp Ser Glu Val Gly His
            580                 585                 590

Val Gly Gly Tyr Thr Glu Ser Ser Glu Glu Ser Asn Pro Ile Asp Phe
        595                 600                 605

Glu Glu Ser Thr His Glu Asn Ser Lys His His Ala Asp Val Val Glu
            610                 615                 620

Tyr Glu Glu Asp Thr Asn Pro Gly Gly Gly Gln Val Thr Thr Glu Ser
625                 630                 635                 640

Asn Leu Val Glu Phe Asp Glu Glu Ser Thr Lys Gly Ile Val Thr Gly
                645                 650                 655

Ala Val Ser Asp His Thr Thr Ile Glu Asp Thr Lys Glu Tyr Thr Thr
            660                 665                 670

Glu Ser Asn Leu Ile Glu Leu Val Asp Glu Leu Pro Glu Glu His Gly
        675                 680                 685

Gln Ala Gln Gly Pro Ile Glu Glu Ile Thr Glu Asn His His Ile
            690                 695                 700

Ser His Ser Gly Leu Gly Thr Glu Asn Gly His Gly Asn Tyr Gly Val
705                 710                 715                 720

Ile Glu Glu Ile Glu Glu Asn Ser His Val Asp Ile Lys Ser Glu Leu
                725                 730                 735

Gly Tyr Glu Gly Gly Gln Asn Ser Gly Asn Gln Ser Phe Glu Glu Asp
```

-continued

```
                740                 745                 750
Thr Glu Glu Asp Lys Pro Lys Tyr Glu Gln Gly Gly Asn Ile Val Asp
            755                 760                 765
Ile Asp Phe Asp Ser Val Pro Gln Ile His Gly Gln Asn Lys Gly Asp
        770                 775                 780
Gln Ser Phe Glu Glu Asp Thr Glu Lys Asp Lys Pro Lys Tyr Glu His
785                 790                 795                 800
Gly Gly Asn Ile Ile Asp Ile Asp Phe Asp Ser Val Pro Gln Ile His
                805                 810                 815
Gly Phe Asn Lys His Asn Glu Ile Ile Glu Asp Thr Asn Lys Asp
            820                 825                 830
Lys Pro Asn Tyr Gln Phe Gly Gly His Asn Ser Val Asp Phe Glu Glu
        835                 840                 845
Asp Thr Leu Pro Lys Val Ser Gly Gln Asn Glu Gly Gln Gln Thr Ile
850                 855                 860
Glu Glu Asp Thr Thr Pro Thr Pro Thr Pro Glu Val Pro Ser
865                 870                 875                 880
Glu Pro Glu Thr Pro Met Pro Pro Thr Pro Glu Val Pro Ser Glu Pro
                885                 890                 895
Glu Thr Pro Thr Pro Pro Thr Pro Glu Val Pro Ser Glu Pro Glu Thr
            900                 905                 910
Pro Thr Pro Pro Thr Pro Glu Val Pro Ser Glu Pro Glu Thr Pro Thr
        915                 920                 925
Pro Pro Thr Pro Glu Val Pro Ser Glu Pro Glu Thr Pro Thr Pro Pro
930                 935                 940
Thr Pro Glu Val Pro Ala Glu Pro Gly Lys Pro Val Pro Pro Ala Lys
945                 950                 955                 960
Glu Glu Pro Lys Lys Pro Ser Lys Pro Val Glu Gln Gly Lys Val Val
                965                 970                 975
Thr Pro Val Ile Glu Ile Asn Glu Lys Val Lys Ala Val Ala Pro Thr
            980                 985                 990
Lys Lys Ala Gln Ser Lys Lys Ser Glu Leu Pro Glu Thr Gly Gly Glu
        995                 1000                1005
Glu Ser Thr Asn Lys Gly Met Leu Phe Gly Gly Leu Phe Ser Ile
    1010                1015                1020
Leu Gly Leu Ala Leu Leu Arg Arg Asn Lys Lys Asn Asn Lys Ala
    1025                1030                1035

<210> SEQ ID NO 4
<211> LENGTH: 1015
<212> TYPE: PRT
<213> ORGANISM: Staphylococcus aureus

<400> SEQUENCE: 4

Val Lys Asn Asn Leu Arg Tyr Gly Ile Arg Lys His Lys Leu Gly Ala
1               5                   10                  15
Ala Ser Val Phe Leu Gly Thr Met Ile Val Gly Met Gly Gln Asp
            20                  25                  30
Lys Glu Ala Ala Ala Ser Glu Gln Lys Thr Thr Thr Val Glu Glu Asn
        35                  40                  45
Gly Asn Ser Ala Thr Glu Asn Lys Val Asn Glu Thr Gln Thr Thr Thr
    50                  55                  60
Thr Asn Val Asn Thr Ile Asp Glu Thr Gln Ser Tyr Ser Ala Thr Ala
65                  70                  75                  80
```

```
Thr Glu Gln Pro Ser Asn Ala Thr Gln Val Thr Thr Glu Glu Ala Pro
                85                  90                  95

Lys Ala Val Gln Ala Pro Gln Thr Ala Gln Pro Ala Asn Leu Glu Thr
                100                 105                 110

Val Lys Glu Glu Val Val Lys Glu Ala Lys Pro Gln Val Lys Glu
            115                 120                 125

Thr Thr Gln Ser Gln Asp Asn Ser Gly Asp Gln Arg Gln Val Asp Leu
        130                 135                 140

Thr Pro Lys Lys Ala Thr Gln Asn Gln Val Ala Glu Thr Gln Val Glu
145                 150                 155                 160

Val Ala Gln Pro Arg Thr Ala Ser Glu Ser Lys Pro Arg Val Thr Arg
                165                 170                 175

Ser Ala Asp Val Val Glu Ala Lys Glu Ala Ser Asp Glu Lys Val Glu
            180                 185                 190

Thr Gly Thr Asp Val Thr Ser Lys Val Thr Val Glu Ser Gly Ser Ile
        195                 200                 205

Glu Ala Pro Gln Gly Asn Lys Val Glu Pro His Ala Gly Gln Arg Val
        210                 215                 220

Val Leu Lys Tyr Lys Leu Lys Phe Ala Asp Gly Leu Lys Arg Gly Asp
225                 230                 235                 240

Tyr Phe Asp Phe Thr Leu Ser Asn Asn Val Asn Thr Tyr Gly Val Ser
                245                 250                 255

Thr Ala Arg Lys Val Pro Glu Ile Lys Asn Gly Ser Val Val Met Ala
            260                 265                 270

Thr Gly Glu Ile Leu Gly Asn Gly Asn Ile Arg Tyr Thr Phe Thr Asn
        275                 280                 285

Glu Ile Glu His Lys Val Glu Val Thr Ala Asn Leu Glu Ile Asn Leu
        290                 295                 300

Phe Ile Asp Pro Lys Thr Val Gln Ser Asn Gly Glu Gln Lys Ile Thr
305                 310                 315                 320

Ser Lys Leu Asn Gly Glu Glu Thr Glu Lys Thr Ile Pro Val Val Tyr
                325                 330                 335

Asn Pro Gly Val Ser Asn Ser Tyr Thr Asn Val Asn Gly Ser Ile Glu
            340                 345                 350

Thr Phe Asn Lys Glu Ser Asn Lys Phe Thr His Ile Ala Tyr Ile Lys
        355                 360                 365

Pro Met Asn Gly Asn Gln Ser Asn Thr Val Ser Val Thr Gly Thr Leu
        370                 375                 380

Thr Glu Gly Ser Asn Leu Ala Gly Gly Gln Pro Thr Val Lys Val Tyr
385                 390                 395                 400

Glu Tyr Leu Gly Lys Lys Asp Glu Leu Pro Gln Ser Val Tyr Ala Asn
                405                 410                 415

Thr Ser Asp Thr Asn Lys Phe Lys Asp Val Thr Lys Glu Met Asn Gly
            420                 425                 430

Lys Leu Ser Val Gln Asp Asn Gly Ser Tyr Ser Leu Asn Leu Asp Lys
        435                 440                 445

Leu Asp Lys Thr Tyr Val Ile His Tyr Thr Gly Glu Tyr Leu Gln Gly
        450                 455                 460

Ser Asp Gln Val Asn Phe Arg Thr Glu Leu Tyr Gly Tyr Pro Glu Arg
465                 470                 475                 480

Ala Tyr Lys Ser Tyr Tyr Val Tyr Gly Gly Tyr Arg Leu Thr Trp Asp
                485                 490                 495

Asn Gly Leu Val Leu Tyr Ser Asn Lys Ala Asp Gly Asn Gly Lys Asn
```

-continued

```
                500                 505                 510
Gly Gln Ile Ile Gln Asn Asn Asp Phe Glu Tyr Lys Glu Asp Thr Ala
            515                 520                 525
Lys Gly Thr Met Ser Gly Gln Tyr Asp Ala Lys Gln Ile Ile Glu Thr
        530                 535                 540
Glu Glu Asn Gln Asp Asn Thr Pro Leu Asp Ile Asp Tyr His Thr Ala
545                 550                 555                 560
Ile Asp Gly Glu Gly Gly Tyr Val Asp Gly Tyr Ile Glu Thr Ile Glu
                565                 570                 575
Glu Thr Asp Ser Ser Ala Ile Asp Ile Asp Tyr His Thr Ala Val Asp
            580                 585                 590
Ser Glu Ala Gly His Val Gly Gly Tyr Thr Glu Ser Ser Glu Glu Ser
        595                 600                 605
Asn Pro Ile Asp Phe Glu Glu Ser Thr His Glu Asn Ser Lys His His
        610                 615                 620
Ala Asp Val Val Glu Tyr Glu Glu Asp Thr Asn Pro Gly Gly Gly Gln
625                 630                 635                 640
Val Thr Thr Glu Ser Asn Leu Val Glu Phe Asp Glu Glu Ser Thr Lys
                645                 650                 655
Gly Ile Val Thr Gly Ala Val Ser Asp His Thr Thr Ile Glu Asp Thr
            660                 665                 670
Lys Glu Tyr Thr Thr Glu Ser Asn Leu Ile Glu Leu Val Asp Glu Leu
        675                 680                 685
Pro Glu Glu His Gly Gln Ala Gln Gly Pro Ile Glu Glu Ile Thr Glu
        690                 695                 700
Asn Asn His His Ile Ser His Ser Gly Leu Gly Thr Glu Asn Gly His
705                 710                 715                 720
Gly Asn Tyr Gly Val Ile Glu Glu Ile Glu Glu Asn Ser His Val Asp
                725                 730                 735
Ile Lys Ser Glu Leu Gly Tyr Glu Gly Gly Gln Asn Ser Gly Asn Gln
            740                 745                 750
Ser Phe Glu Glu Asp Thr Glu Glu Asp Lys Pro Lys Tyr Glu Gln Gly
        755                 760                 765
Gly Asn Ile Val Asp Ile Asp Phe Asp Ser Val Pro Gln Ile Gln Gly
    770                 775                 780
Gln Asn Asn Gly Asn Gln Ser Phe Glu Glu Asp Thr Glu Lys Asp Lys
785                 790                 795                 800
Pro Lys Tyr Glu Gln Gly Gly Asn Ile Ile Asp Ile Asp Phe Asp Ser
                805                 810                 815
Val Pro Gln Ile His Gly Phe Asn Lys His Thr Glu Ile Ile Glu Glu
            820                 825                 830
Asp Thr Asn Lys Asp Lys Pro Asn Tyr Gln Phe Gly Gly His Asn Ser
        835                 840                 845
Val Asp Phe Glu Glu Asp Thr Leu Pro Lys Val Ser Gly Gln Asn Glu
    850                 855                 860
Gly Gln Gln Thr Ile Glu Glu Asp Thr Pro Pro Thr Pro Pro Thr
865                 870                 875                 880
Pro Glu Val Pro Ser Glu Pro Glu Thr Pro Thr Pro Pro Thr Pro Glu
                885                 890                 895
Val Pro Ser Glu Pro Glu Thr Pro Thr Pro Thr Pro Glu Val Pro
            900                 905                 910
Ser Glu Pro Glu Thr Pro Thr Pro Pro Thr Pro Glu Val Pro Ala Glu
        915                 920                 925
```

```
Pro Gly Lys Pro Val Pro Ala Lys Glu Pro Lys Pro Ser
        930                 935                 940
Lys Pro Val Glu Gln Gly Lys Val Val Thr Pro Val Ile Glu Ile Asn
945                 950                 955                 960
Glu Lys Val Lys Ala Val Ala Pro Thr Lys Ala Gln Ser Lys Lys
                965                 970                 975
Ser Glu Leu Pro Glu Thr Gly Gly Glu Ser Thr Asn Lys Gly Met
            980                 985                 990
Leu Phe Gly Gly Leu Phe Ser Ile Leu Gly Leu Ala Leu Leu Arg Arg
            995                 1000                1005
Asn Lys  Lys Asn Asn Lys Ala
    1010                1015

<210> SEQ ID NO 5
<211> LENGTH: 1023
<212> TYPE: PRT
<213> ORGANISM: Staphylococcus aureus

<400> SEQUENCE: 5

Leu His Leu Lys Gly Asp Ile Ile Val Lys Asn Asn Leu Arg Tyr Gly
1               5                   10                  15
Ile Arg Lys His Lys Leu Gly Ala Ala Ser Val Phe Leu Gly Thr Met
            20                  25                  30
Ile Val Val Gly Met Gly Gln Asp Lys Glu Ala Ala Ala Ser Glu Gln
        35                  40                  45
Lys Thr Thr Thr Val Glu Glu Asn Gly Asn Ser Ala Thr Glu Asn Lys
    50                  55                  60
Val Asn Glu Thr Gln Thr Thr Thr Asn Val Asn Thr Ile Asp Glu
65                  70                  75                  80
Thr Gln Ser Tyr Ser Ala Thr Ala Thr Glu Gln Pro Ser Asn Ala Thr
                85                  90                  95
Gln Val Thr Thr Glu Glu Ala Pro Lys Ala Val Gln Ala Pro Gln Thr
            100                 105                 110
Ala Gln Pro Ala Asn Leu Glu Thr Val Lys Glu Val Val Lys Glu
        115                 120                 125
Glu Ala Lys Pro Gln Val Lys Glu Thr Thr Gln Ser Gln Asp Asn Ser
    130                 135                 140
Gly Asp Gln Arg Gln Val Asp Leu Thr Pro Lys Lys Ala Thr Gln Asn
145                 150                 155                 160
Gln Val Ala Glu Thr Gln Val Glu Val Ala Gln Pro Arg Thr Ala Ser
                165                 170                 175
Glu Ser Lys Pro Arg Val Thr Arg Ser Ala Asp Val Val Glu Ala Lys
            180                 185                 190
Glu Ala Ser Asp Glu Lys Val Glu Thr Gly Thr Asp Val Thr Ser Lys
        195                 200                 205
Val Thr Val Glu Ser Gly Ser Ile Glu Ala Pro Gln Gly Asn Lys Val
    210                 215                 220
Glu Pro His Ala Gly Gln Arg Val Val Leu Lys Tyr Lys Leu Lys Phe
225                 230                 235                 240
Ala Asp Gly Leu Lys Arg Gly Asp Tyr Phe Asp Phe Thr Leu Ser Asn
                245                 250                 255
Asn Val Asn Thr Tyr Gly Val Ser Thr Ala Arg Lys Val Pro Glu Ile
            260                 265                 270
Lys Asn Gly Ser Val Val Met Ala Thr Gly Glu Ile Leu Gly Asn Gly
```

-continued

```
                275                 280                 285
Asn Ile Arg Tyr Thr Phe Thr Asn Glu Ile Glu His Lys Val Glu Val
290                 295                 300
Thr Ala Asn Leu Glu Ile Asn Leu Phe Ile Asp Pro Lys Thr Val Gln
305                 310                 315                 320
Ser Asn Gly Glu Gln Lys Ile Thr Ser Lys Leu Asn Gly Glu Thr
                325                 330                 335
Glu Lys Thr Ile Pro Val Val Tyr Asn Pro Gly Val Ser Asn Ser Tyr
                340                 345                 350
Thr Asn Val Asn Gly Ser Ile Glu Thr Phe Asn Lys Glu Ser Asn Lys
                355                 360                 365
Phe Thr His Ile Ala Tyr Ile Lys Pro Met Asn Gly Asn Gln Ser Asn
                370                 375                 380
Thr Val Ser Val Thr Gly Thr Leu Thr Glu Gly Ser Asn Leu Ala Gly
385                 390                 395                 400
Gly Gln Pro Thr Val Lys Val Tyr Glu Tyr Leu Gly Lys Lys Asp Glu
                405                 410                 415
Leu Pro Gln Ser Val Tyr Ala Asn Thr Ser Asp Thr Asn Lys Phe Lys
                420                 425                 430
Asp Val Thr Lys Glu Met Asn Gly Lys Leu Ser Val Gln Asp Asn Gly
                435                 440                 445
Ser Tyr Ser Leu Asn Leu Asp Lys Leu Asp Lys Thr Tyr Val Ile His
                450                 455                 460
Tyr Thr Gly Glu Tyr Leu Gln Gly Ser Asp Gln Val Asn Phe Arg Thr
465                 470                 475                 480
Glu Leu Tyr Gly Tyr Pro Glu Arg Ala Tyr Lys Ser Tyr Tyr Val Tyr
                485                 490                 495
Gly Gly Tyr Arg Leu Thr Trp Asp Asn Gly Leu Val Leu Tyr Ser Asn
                500                 505                 510
Lys Ala Asp Gly Asn Gly Lys Asn Gly Gln Ile Ile Gln Asn Asn Asp
                515                 520                 525
Phe Glu Tyr Lys Glu Asp Thr Ala Lys Gly Thr Met Ser Gly Gln Tyr
                530                 535                 540
Asp Ala Lys Gln Ile Ile Glu Thr Glu Glu Asn Gln Asp Asn Thr Pro
545                 550                 555                 560
Leu Asp Ile Asp Tyr His Thr Ala Ile Asp Gly Glu Gly Gly Tyr Val
                565                 570                 575
Asp Gly Tyr Ile Glu Thr Ile Glu Glu Thr Asp Ser Ser Ala Ile Asp
                580                 585                 590
Ile Asp Tyr His Thr Ala Val Asp Ser Glu Ala Gly His Val Gly Gly
                595                 600                 605
Tyr Thr Glu Ser Ser Glu Glu Ser Asn Pro Ile Asp Phe Glu Glu Ser
                610                 615                 620
Thr His Glu Asn Ser Lys His His Ala Asp Val Glu Tyr Glu Glu
625                 630                 635                 640
Asp Thr Asn Pro Gly Gly Gly Gln Val Thr Thr Glu Ser Asn Leu Val
                645                 650                 655
Glu Phe Asp Glu Glu Ser Thr Lys Gly Ile Val Thr Gly Ala Val Ser
                660                 665                 670
Asp His Thr Thr Ile Glu Asp Thr Lys Glu Tyr Thr Thr Glu Ser Asn
                675                 680                 685
Leu Ile Glu Leu Val Asp Glu Leu Pro Glu Glu His Gly Gln Ala Gln
                690                 695                 700
```

Gly Pro Ile Glu Glu Ile Thr Glu Asn Asn His His Ile Ser His Ser
705                 710                 715                 720

Gly Leu Gly Thr Glu Asn Gly His Gly Asn Tyr Gly Val Ile Glu Glu
                725                 730                 735

Ile Glu Glu Asn Ser His Val Asp Ile Lys Ser Glu Leu Gly Tyr Glu
            740                 745                 750

Gly Gly Gln Asn Ser Gly Asn Gln Ser Phe Glu Glu Asp Thr Glu Glu
        755                 760                 765

Asp Lys Pro Lys Tyr Glu Gln Gly Asn Ile Val Asp Ile Asp Phe
770                 775                 780

Asp Ser Val Pro Gln Ile Gln Gly Gln Asn Asn Gly Asn Gln Ser Phe
785                 790                 795                 800

Glu Glu Asp Thr Glu Lys Asp Lys Pro Lys Tyr Glu Gln Gly Gly Asn
                805                 810                 815

Ile Ile Asp Ile Asp Phe Asp Ser Val Pro Gln Ile His Gly Phe Asn
            820                 825                 830

Lys His Thr Glu Ile Ile Glu Glu Asp Thr Asn Lys Asp Lys Pro Asn
835                 840                 845

Tyr Gln Phe Gly Gly His Asn Ser Val Asp Phe Glu Glu Asp Thr Leu
850                 855                 860

Pro Lys Val Ser Gly Gln Asn Glu Gly Gln Gln Thr Ile Glu Glu Asp
865                 870                 875                 880

Thr Thr Pro Pro Thr Pro Thr Pro Glu Val Pro Ser Glu Pro Glu
                885                 890                 895

Thr Pro Thr Pro Pro Thr Pro Glu Val Pro Ser Glu Pro Glu Thr Pro
                900                 905                 910

Thr Pro Pro Thr Pro Glu Val Pro Ser Glu Pro Glu Thr Pro Thr Pro
            915                 920                 925

Pro Thr Pro Glu Val Pro Ala Glu Pro Gly Lys Pro Val Pro Pro Ala
        930                 935                 940

Lys Glu Glu Pro Lys Lys Pro Ser Lys Pro Val Glu Gln Gly Lys Val
945                 950                 955                 960

Val Thr Pro Val Ile Glu Ile Asn Glu Lys Val Lys Ala Val Ala Pro
                965                 970                 975

Thr Lys Lys Ala Gln Ser Lys Lys Ser Glu Leu Pro Glu Thr Gly Gly
            980                 985                 990

Glu Glu Ser Thr Asn Lys Gly Met Leu Phe Gly Gly Leu Phe Ser Ile
        995                 1000                1005

Leu Gly Leu Ala Leu Leu Arg Arg Asn Lys Lys Asn Asn Lys Ala
    1010                1015                1020

<210> SEQ ID NO 6
<211> LENGTH: 1018
<212> TYPE: PRT
<213> ORGANISM: Staphylococcus aureus

<400> SEQUENCE: 6

Val Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala Ala Ser Glu Gln Lys Thr Thr Thr Val Glu Glu Asn
        35                  40                  45

Gly Asn Ser Ala Thr Asp Asn Lys Thr Ser Glu Thr Gln Thr Thr Ala

```
               50                  55                  60
Thr Asn Val Asn His Ile Glu Glu Thr Gln Ser Tyr Asn Ala Thr Val
 65                  70                  75                  80

Thr Glu Gln Pro Ser Asn Ala Thr Gln Val Thr Thr Glu Glu Ala Pro
                 85                  90                  95

Lys Ala Val Gln Ala Pro Gln Thr Ala Gln Pro Ala Asn Ile Glu Thr
                100                 105                 110

Val Lys Glu Glu Val Val Lys Glu Ala Lys Pro Gln Val Lys Glu
            115                 120                 125

Thr Thr Gln Ser Gln Asp Asn Ser Gly Asp Gln Arg Gln Val Asp Leu
130                 135                 140

Thr Pro Lys Lys Ala Thr Gln Asn Gln Val Ala Glu Thr Gln Val Glu
145                 150                 155                 160

Val Ala Gln Pro Arg Thr Ala Ser Glu Ser Lys Pro Arg Val Thr Arg
                165                 170                 175

Ser Ala Asp Val Ala Glu Ala Lys Glu Ala Ser Asn Ala Lys Val Glu
            180                 185                 190

Thr Gly Thr Asp Val Thr Ser Lys Val Thr Val Glu Ile Gly Ser Ile
            195                 200                 205

Glu Gly His Asn Asn Thr Asn Lys Val Glu Pro His Ala Gly Gln Arg
210                 215                 220

Ala Val Leu Lys Tyr Lys Leu Lys Phe Glu Asn Gly Leu His Gln Gly
225                 230                 235                 240

Asp Tyr Phe Asp Phe Thr Leu Ser Asn Asn Val Asn Thr His Gly Val
                245                 250                 255

Ser Thr Ala Arg Lys Val Pro Glu Ile Lys Asn Gly Ser Val Val Met
            260                 265                 270

Ala Thr Gly Glu Val Leu Glu Gly Gly Lys Ile Arg Tyr Thr Phe Thr
            275                 280                 285

Asn Asp Ile Glu Asp Lys Val Asp Val Thr Ala Glu Leu Glu Ile Asn
290                 295                 300

Leu Phe Ile Asp Pro Lys Thr Val Gln Thr Asn Gly Asn Gln Thr Ile
305                 310                 315                 320

Thr Ser Thr Leu Asn Glu Glu Gln Ser Lys Glu Leu Asp Val Lys
                325                 330                 335

Tyr Lys Asp Gly Ile Gly Asn Tyr Tyr Ala Asn Leu Asn Gly Ser Ile
            340                 345                 350

Glu Thr Phe Asn Lys Ala Asn Asn Arg Phe Ser His Val Ala Phe Ile
            355                 360                 365

Lys Pro Asn Asn Gly Lys Thr Thr Ser Val Thr Val Thr Gly Thr Leu
370                 375                 380

Met Lys Gly Ser Asn Gln Asn Gly Asn Gln Pro Lys Val Arg Ile Phe
385                 390                 395                 400

Glu Tyr Leu Gly Asn Asn Glu Asp Ile Ala Lys Ser Val Tyr Ala Asn
                405                 410                 415

Thr Thr Asp Thr Ser Lys Phe Lys Glu Val Thr Ser Asn Met Ser Gly
            420                 425                 430

Asn Leu Asn Leu Gln Asn Asn Gly Ser Tyr Ser Leu Asn Ile Glu Asn
            435                 440                 445

Leu Asp Lys Thr Tyr Val Val His Tyr Asp Gly Glu Tyr Leu Asn Gly
450                 455                 460

Thr Asp Glu Val Asp Phe Arg Thr Gln Met Val Gly His Pro Glu Gln
465                 470                 475                 480
```

```
Leu Tyr Lys Tyr Tyr Asp Arg Gly Tyr Thr Leu Thr Trp Asp Asn
            485                 490                 495

Gly Leu Val Leu Tyr Ser Asn Lys Ala Asn Gly Asn Gly Lys Asn Gly
            500                 505                 510

Pro Ile Ile Gln Asn Asn Lys Phe Glu Tyr Lys Glu Asp Thr Ile Lys
            515                 520                 525

Glu Thr Leu Thr Gly Gln Tyr Asp Lys Asn Leu Val Thr Thr Val Glu
            530                 535                 540

Glu Glu Tyr Asp Ser Ser Thr Leu Asp Ile Asp Tyr His Thr Ala Ile
545                 550                 555                 560

Asp Gly Gly Gly Gly Tyr Val Asp Gly Tyr Ile Glu Thr Ile Glu Glu
                565                 570                 575

Thr Asp Ser Ser Ala Ile Asp Ile Asp Tyr His Thr Ala Val Asp Ser
            580                 585                 590

Glu Ala Gly His Val Gly Gly Tyr Thr Glu Ser Ser Glu Glu Ser Asn
            595                 600                 605

Pro Ile Asp Phe Glu Glu Ser Thr His Glu Asn Ser Lys His His Ala
            610                 615                 620

Asp Val Val Glu Tyr Glu Glu Asp Thr Asn Pro Gly Gly Gly Gln Val
625                 630                 635                 640

Thr Thr Glu Ser Asn Leu Val Glu Phe Asp Glu Glu Ser Thr Lys Gly
            645                 650                 655

Ile Val Thr Gly Ala Val Ser Asp His Thr Thr Val Glu Asp Thr Lys
            660                 665                 670

Glu Tyr Thr Thr Glu Ser Asn Leu Ile Glu Leu Val Asp Glu Leu Pro
            675                 680                 685

Glu Glu His Gly Gln Ala Gln Gly Pro Val Glu Glu Ile Thr Glu Asn
            690                 695                 700

Asn His His Ile Ser His Ser Gly Leu Gly Thr Glu Asn Gly His Gly
705                 710                 715                 720

Asn Tyr Asp Val Ile Glu Glu Ile Glu Glu Asn Ser His Val Asp Ile
            725                 730                 735

Lys Ser Glu Leu Gly Tyr Glu Gly Gly Gln Asn Ser Gly Asn Gln Ser
            740                 745                 750

Phe Glu Glu Asp Thr Glu Glu Asp Lys Pro Lys Tyr Glu Gln Gly Gly
            755                 760                 765

Asn Ile Val Asp Ile Asp Phe Asp Ser Val Pro Gln Ile His Gly Gln
            770                 775                 780

Asn Lys Gly Asn Gln Ser Phe Glu Glu Asp Thr Glu Lys Asp Lys Pro
785                 790                 795                 800

Lys Tyr Glu His Gly Gly Asn Ile Ile Asp Ile Asp Phe Asp Ser Val
            805                 810                 815

Pro His Ile His Gly Phe Asn Lys His Thr Glu Ile Ile Glu Glu Asp
            820                 825                 830

Thr Asn Lys Asp Lys Pro Ser Tyr Gln Phe Gly Gly His Asn Ser Val
            835                 840                 845

Asp Phe Glu Glu Asp Thr Leu Pro Lys Val Ser Gly Gln Asn Glu Gly
            850                 855                 860

Gln Gln Thr Ile Glu Glu Asp Thr Thr Pro Pro Ile Val Pro Pro Thr
865                 870                 875                 880

Pro Pro Thr Pro Glu Val Pro Ser Glu Pro Glu Thr Pro Thr Pro Pro
            885                 890                 895
```

```
Thr Pro Glu Val Pro Ser Glu Pro Thr Pro Thr Pro Thr Pro
            900                 905                 910

Glu Val Pro Ser Glu Pro Glu Thr Pro Thr Pro Thr Pro Glu Val
            915                 920                 925

Pro Ala Glu Pro Gly Lys Pro Val Pro Ala Lys Glu Glu Pro Lys
            930                 935                 940

Lys Pro Ser Lys Pro Val Glu Gln Gly Lys Val Val Thr Pro Val Ile
945                 950                 955                 960

Glu Ile Asn Glu Lys Val Lys Ala Val Ala Pro Thr Lys Lys Pro Gln
                965                 970                 975

Ser Lys Lys Ser Glu Leu Pro Glu Thr Gly Gly Glu Ser Thr Asn
            980                 985                 990

Lys Gly Met Leu Phe Gly Gly Leu Phe Ser Ile Leu Gly Leu Ala Leu
            995                 1000                1005

Leu Arg Arg Asn Lys Lys Asn His Lys Ala
            1010                1015

<210> SEQ ID NO 7
<211> LENGTH: 1018
<212> TYPE: PRT
<213> ORGANISM: Staphylococcus aureus

<400> SEQUENCE: 7

Val Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
                20                  25                  30

Lys Glu Ala Ala Ser Glu Gln Lys Thr Thr Thr Val Glu Glu Asn
            35                  40                  45

Gly Asn Ser Ala Thr Asp Asn Lys Thr Ser Glu Thr Gln Thr Thr Ala
        50                  55                  60

Thr Asn Val Asn His Ile Glu Glu Thr Gln Ser Tyr Asn Ala Thr Val
65                  70                  75                  80

Thr Glu Gln Pro Ser Asn Ala Thr Gln Val Thr Thr Glu Glu Ala Pro
                85                  90                  95

Lys Ala Val Gln Ala Pro Gln Thr Ala Gln Pro Ala Asn Ile Glu Thr
            100                 105                 110

Val Lys Glu Glu Val Val Lys Glu Ala Lys Pro Gln Val Lys Glu
            115                 120                 125

Thr Thr Gln Ser Gln Asp Asn Ser Gly Asp Gln Arg Gln Val Asp Leu
        130                 135                 140

Thr Pro Lys Lys Ala Thr Gln Asn Gln Val Ala Glu Thr Gln Val Glu
145                 150                 155                 160

Val Ala Gln Pro Arg Thr Ala Ser Glu Ser Lys Pro Arg Val Thr Arg
                165                 170                 175

Ser Ala Asp Val Ala Glu Ala Lys Ala Ser Asn Ala Lys Val Glu
            180                 185                 190

Thr Gly Thr Asp Val Thr Ser Lys Val Thr Val Glu Ile Gly Ser Ile
        195                 200                 205

Glu Gly His Asn Asn Thr Asn Lys Val Glu Pro His Ala Gly Gln Arg
            210                 215                 220

Ala Val Leu Lys Tyr Lys Leu Lys Phe Glu Asn Gly Leu His Gln Gly
225                 230                 235                 240

Asp Tyr Phe Asp Phe Thr Leu Ser Asn Asn Val Asn Thr His Gly Val
                245                 250                 255
```

-continued

```
Ser Thr Ala Arg Lys Val Pro Glu Ile Lys Asn Gly Ser Val Val Met
            260                 265                 270

Ala Thr Gly Glu Val Leu Glu Gly Lys Ile Arg Tyr Thr Phe Thr
        275                 280                 285

Asn Asp Ile Glu Asp Lys Val Asp Val Thr Ala Glu Leu Glu Ile Asn
    290                 295                 300

Leu Phe Ile Asp Pro Lys Thr Val Gln Thr Asn Gly Asn Gln Thr Ile
305                 310                 315                 320

Thr Ser Thr Leu Asn Glu Glu Gln Thr Ser Lys Glu Leu Asp Val Lys
                325                 330                 335

Tyr Lys Asp Gly Ile Gly Asn Tyr Tyr Ala Asn Leu Asn Gly Ser Ile
            340                 345                 350

Glu Thr Phe Asn Lys Ala Asn Asn Arg Phe Ser His Val Ala Phe Ile
        355                 360                 365

Lys Pro Asn Asn Gly Lys Thr Thr Ser Val Thr Val Thr Gly Thr Leu
    370                 375                 380

Met Lys Gly Ser Asn Gln Asn Gly Asn Gln Pro Lys Val Arg Ile Phe
385                 390                 395                 400

Glu Tyr Leu Gly Asn Asn Glu Asp Ile Ala Lys Ser Val Tyr Ala Asn
                405                 410                 415

Thr Thr Asp Thr Ser Lys Phe Lys Glu Val Thr Ser Asn Met Ser Gly
            420                 425                 430

Asn Leu Asn Leu Gln Asn Asn Gly Ser Tyr Ser Leu Asn Ile Glu Asn
        435                 440                 445

Leu Asp Lys Thr Tyr Val Val His Tyr Asp Gly Glu Tyr Leu Asn Gly
    450                 455                 460

Thr Asp Glu Val Asp Phe Arg Thr Gln Met Val Gly His Pro Glu Gln
465                 470                 475                 480

Leu Tyr Lys Tyr Tyr Tyr Asp Arg Gly Tyr Thr Leu Thr Trp Asp Asn
                485                 490                 495

Gly Leu Val Leu Tyr Ser Asn Lys Ala Asn Gly Asn Glu Lys Asn Gly
            500                 505                 510

Pro Ile Ile Gln Asn Asn Lys Phe Glu Tyr Lys Glu Asp Thr Ile Lys
        515                 520                 525

Glu Thr Leu Thr Gly Gln Tyr Asp Lys Asn Leu Val Thr Thr Val Glu
    530                 535                 540

Glu Glu Tyr Asp Ser Ser Thr Leu Asp Ile Asp Tyr His Thr Ala Ile
545                 550                 555                 560

Asp Gly Gly Gly Gly Tyr Val Asp Gly Tyr Ile Glu Thr Ile Glu Glu
                565                 570                 575

Thr Asp Ser Ser Ala Ile Asp Ile Asp Tyr His Thr Ala Val Asp Ser
            580                 585                 590

Glu Ala Gly His Val Gly Gly Tyr Thr Glu Ser Ser Glu Glu Ser Asn
        595                 600                 605

Pro Ile Asp Phe Glu Glu Ser Thr His Glu Asn Ser Lys His His Ala
    610                 615                 620

Asp Val Val Glu Tyr Glu Glu Asp Thr Asn Pro Gly Gly Gly Gln Val
625                 630                 635                 640

Thr Thr Glu Ser Asn Leu Val Glu Phe Asp Glu Glu Ser Thr Lys Gly
                645                 650                 655

Ile Val Thr Gly Ala Val Ser Asp His Thr Thr Val Glu Asp Thr Lys
            660                 665                 670
```

Glu Tyr Thr Thr Glu Ser Asn Leu Ile Glu Leu Val Asp Glu Leu Pro
                675                 680                 685

Glu Glu His Gly Gln Ala Gln Gly Pro Val Glu Ile Thr Lys Asn
690                 695                 700

Asn His His Ile Ser His Ser Gly Leu Gly Thr Glu Asn Gly His Gly
705                 710                 715                 720

Asn Tyr Asp Val Ile Glu Glu Ile Glu Glu Asn Ser His Val Asp Ile
                725                 730                 735

Lys Ser Glu Leu Gly Tyr Glu Gly Gly Gln Asn Ser Gly Asn Gln Ser
                740                 745                 750

Phe Glu Glu Asp Thr Glu Glu Asp Lys Pro Lys Tyr Glu Gln Gly Gly
                755                 760                 765

Asn Ile Val Asp Ile Asp Phe Asp Ser Val Pro Gln Ile His Gly Gln
770                 775                 780

Asn Lys Gly Asn Gln Ser Phe Glu Glu Asp Thr Glu Lys Asp Lys Pro
785                 790                 795                 800

Lys Tyr Glu His Gly Gly Asn Ile Ile Asp Ile Asp Phe Asp Ser Val
                805                 810                 815

Pro His Ile His Gly Phe Asn Lys His Thr Glu Ile Ile Glu Glu Asp
                820                 825                 830

Thr Asn Lys Asp Lys Pro Ser Tyr Gln Phe Gly Gly His Asn Ser Val
835                 840                 845

Asp Phe Glu Glu Asp Thr Leu Pro Lys Val Ser Gly Gln Asn Glu Gly
850                 855                 860

Gln Gln Thr Ile Glu Glu Asp Thr Thr Pro Ile Val Pro Pro Thr
865                 870                 875                 880

Pro Pro Thr Pro Glu Val Pro Ser Glu Pro Glu Thr Pro Thr Pro Pro
                885                 890                 895

Thr Pro Glu Val Pro Ser Glu Pro Glu Thr Pro Thr Pro Thr Pro
                900                 905                 910

Glu Val Pro Ser Glu Pro Glu Thr Pro Thr Pro Thr Pro Glu Val
                915                 920                 925

Pro Ala Glu Pro Gly Lys Pro Val Pro Pro Ala Lys Glu Glu Pro Lys
930                 935                 940

Lys Pro Ser Lys Pro Val Glu Gln Gly Lys Val Val Thr Pro Val Ile
945                 950                 955                 960

Glu Ile Asn Glu Lys Val Lys Ala Val Ala Pro Thr Lys Lys Pro Gln
                965                 970                 975

Ser Lys Lys Ser Glu Leu Pro Glu Thr Gly Gly Glu Glu Ser Thr Asn
                980                 985                 990

Lys Gly Met Leu Phe Gly Gly Leu Phe Ser Ile Leu Gly Leu Ala Leu
                995                 1000                1005

Leu Arg Arg Asn Lys Lys Asn His Lys Ala
    1010                1015

<210> SEQ ID NO 8
<211> LENGTH: 973
<212> TYPE: PRT
<213> ORGANISM: Staphylococcus aureus

<400> SEQUENCE: 8

Leu His Leu Lys Gly Asp Ile Ile Val Lys Asn Asn Leu Arg Tyr Gly
1               5                   10                  15

Ile Arg Lys His Lys Leu Gly Ala Ala Ser Val Phe Leu Gly Thr Met
                20                  25                  30

```
Ile Val Ile Gly Met Gly Gln Asp Lys Glu Ala Ala Ser Glu Gln
         35                  40                  45

Lys Thr Thr Thr Val Glu Glu Asn Gly Asn Ser Ala Thr Asp Asn Lys
 50                  55                  60

Val Ser Glu Thr Gln Thr Thr Thr Asn Val Asn Thr Ile Asp Glu
 65                  70                  75                  80

Thr Gln Ser Tyr Ser Ala Thr Ala Thr Glu Gln Pro Ser Asn Ala Thr
                 85                  90                  95

Gln Val Thr Thr Glu Glu Ala Pro Lys Ala Val Gln Ala Pro Gln Thr
                100                 105                 110

Ala Gln Pro Ala Asn Val Glu Thr Val Lys Glu Glu Val Lys Glu
            115                 120                 125

Glu Ala Asn Pro Gln Val Lys Glu Thr Thr Gln Ser Gln Asp Asn Ser
            130                 135                 140

Gly Asp Gln Arg Gln Val Asp Leu Thr Pro Lys Lys Ala Thr Gln Asn
145                 150                 155                 160

Gln Val Ala Glu Thr Gln Val Glu Val Ala Gln Pro Arg Thr Ala Leu
                165                 170                 175

Glu Ser Lys Pro Arg Val Thr Arg Ser Thr Asp Val Ala Glu Ala Lys
                180                 185                 190

Glu Ala Ser Asp Ala Lys Val Glu Thr Gly Thr Asp Val Thr Ser Lys
            195                 200                 205

Val Thr Val Glu Asp Glu Ser Lys Ile Glu Ala Pro Lys Gly Asn Asn
            210                 215                 220

Val Gln Pro His Glu Gly Gln Arg Val Val Leu Lys Tyr Lys Leu Lys
225                 230                 235                 240

Phe Gln Asp Gly Leu Lys Thr Gly Asp Tyr Phe Asp Phe Thr Leu Ser
                245                 250                 255

Asn Asn Val Asn Thr His Gly Val Ala Thr Thr Arg Lys Val Pro Asp
            260                 265                 270

Ile Lys Asn Gly Ser Leu Val Met Ala Lys Gly Gln Val Leu Asp Asn
            275                 280                 285

Gly Arg Ile Arg Tyr Thr Phe Thr Asp Tyr Ile Lys Asp Lys Val Asn
            290                 295                 300

Val Thr Ala Asn Leu Glu Ile Asn Leu Phe Ile Asp Pro Lys Thr Val
305                 310                 315                 320

Gln Ser Asn Gly Gln Gln Thr Ile Thr Ser Lys Leu Asn Gly Lys Glu
                325                 330                 335

Thr Ser Gly Thr Met Gln Ile Thr Tyr Lys Asp Gly Val Lys Asn Gln
                340                 345                 350

Tyr Thr Asn Val Asn Gly Ser Ile Glu Thr Phe Asp Lys Glu Lys Asn
            355                 360                 365

Lys Phe Thr His Val Ala Tyr Ile Lys Pro Ile Asn Gly Asn Asn Ser
            370                 375                 380

Asp Ser Val Thr Val Thr Gly Met Leu Thr Gln Gly Ser Asn Glu Asn
385                 390                 395                 400

Gly Thr Gln Pro Asn Val Lys Ile Tyr Glu Tyr Val Gly Val Glu Asn
                405                 410                 415

Gly Leu Pro Gln Ser Val Tyr Ala Asn Thr Val Asp Ser Thr Gln Leu
            420                 425                 430

Lys Asp Val Thr Asn Gln Met Gly Asp Lys Leu Lys Val Gln Asn Asn
            435                 440                 445
```

-continued

```
Gly Ser Tyr Ser Leu Asn Phe Asp Lys Leu Asp Lys Thr Tyr Val Ile
    450                 455                 460

His Tyr Thr Gly Asp Tyr Leu Asn Gly Thr Ser Glu Val Asn Phe Arg
465                 470                 475                 480

Thr Gln Leu Thr Gly Tyr Pro Glu Asn Arg Tyr Lys Thr Tyr Tyr Tyr
                485                 490                 495

Tyr Asn Asn Gly Tyr Thr Leu Thr Trp Asp Asn Gly Leu Val Leu Tyr
            500                 505                 510

Ser Asn Lys Ala Asn Gly Asp Gly Lys Tyr Gly Pro Ile Val Asp Ser
        515                 520                 525

Asn Asn Phe Glu Phe Ser Glu Asp Ser Gly Asn Gly Ser Ile Ser Gly
        530                 535                 540

Gln Tyr Asp Ala Lys Gln Ile Ile Glu Thr Glu Glu Asn Gln Asp Asn
545                 550                 555                 560

Thr Pro Leu Asp Ile Asp Tyr His Thr Ala Ile Asp Gly Glu Gly Gly
                565                 570                 575

Tyr Val Asp Gly Tyr Ile Glu Thr Ile Glu Glu Thr Asp Ser Ser Ala
            580                 585                 590

Ile Asp Ile Asp Tyr His Thr Ala Val Asp Ser Glu Ala Gly His Val
        595                 600                 605

Gly Gly Tyr Thr Glu Ser Ser Glu Glu Ser Asn Pro Ile Asp Phe Glu
    610                 615                 620

Glu Ser Thr His Glu Asn Ser Lys His His Ala Asp Val Val Glu Tyr
625                 630                 635                 640

Glu Glu Asp Thr Asn Pro Gly Gly Gly Gln Val Thr Thr Glu Ser Asn
                645                 650                 655

Leu Val Glu Phe Asp Glu Glu Ser Thr Lys Gly Ile Val Thr Gly Ala
            660                 665                 670

Val Ser Asp His Thr Thr Val Glu Asp Thr Lys Glu Tyr Thr Thr Glu
        675                 680                 685

Ser Asn Leu Ile Glu Leu Val Asp Glu Leu Pro Glu Glu His Gly Gln
        690                 695                 700

Ala Gln Gly Pro Val Glu Glu Ile Thr Glu Asn His His Ile Ser
705                 710                 715                 720

His Ser Gly Leu Gly Thr Glu Asn Gly His Gly Asn Tyr Gly Val Ile
                725                 730                 735

Glu Glu Ile Glu Glu Asn Ser His Val Asp Ile Lys Ser Glu Leu Gly
            740                 745                 750

Tyr Glu Gly Gly Gln Asn Ser Gly Asn Gln Ser Phe Glu Glu Asp Thr
        755                 760                 765

Glu Glu Asp Lys Pro Lys Tyr Glu Gln Gly Gly Asn Ile Ile Asp Ile
        770                 775                 780

Asp Phe Asp Ser Val Pro Gln Ile His Gly Phe Asn Lys His Asn Glu
785                 790                 795                 800

Ile Ile Glu Glu Asp Thr Asn Lys Asp Lys Pro Asn Tyr Gln Phe Gly
                805                 810                 815

Gly His Asn Ser Val Asp Phe Glu Glu Asp Thr Leu Pro Lys Val Ser
            820                 825                 830

Gly Gln Asn Glu Gly Gln Gln Thr Ile Glu Glu Asp Thr Thr Pro Pro
        835                 840                 845

Thr Pro Pro Thr Pro Glu Val Pro Ser Glu Pro Gly Thr Pro Thr Pro
850                 855                 860

Pro Thr Pro Glu Val Pro Ser Glu Pro Gly Lys Pro Thr Pro Pro Thr
```

```
                865                 870                 875                 880
Pro Glu Val Pro Ala Glu Pro Gly Lys Pro Val Pro Ala Lys Glu
                    885                 890                 895
Glu Pro Lys Lys Pro Ser Lys Pro Val Glu Gln Gly Lys Val Val Thr
                900                 905                 910
Pro Val Ile Glu Ile Asn Glu Lys Val Lys Ala Val Ala Pro Thr Lys
                915                 920                 925
Gln Lys Gln Ala Lys Lys Ser Glu Leu Pro Glu Thr Gly Gly Glu
                930                 935                 940
Ser Thr Asn Lys Gly Met Leu Phe Gly Gly Leu Phe Ser Ile Leu Gly
945                 950                 955                 960
Leu Ala Leu Leu Arg Arg Asn Lys Lys Asn His Lys Ala
                965                 970

<210> SEQ ID NO 9
<211> LENGTH: 961
<212> TYPE: PRT
<213> ORGANISM: Staphylococcus aureus

<400> SEQUENCE: 9

Val Lys Ser Asn Leu Arg Tyr Gly Ile Arg Lys His Lys Leu Gly Ala
1               5                   10                  15
Ala Ser Val Phe Leu Gly Thr Met Ile Val Gly Met Gly Gln Glu
                20                  25                  30
Lys Glu Ala Ala Ala Ser Glu Gln Asn Asn Thr Thr Val Glu Glu Ser
            35                  40                  45
Gly Ser Ser Ala Thr Glu Ser Lys Ala Ser Glu Thr Gln Thr Thr Thr
        50                  55                  60
Asn Asn Val Asn Thr Ile Asp Glu Thr Gln Ser Tyr Ser Ala Thr Ser
65                  70                  75                  80
Thr Glu Gln Pro Ser Lys Ser Thr Gln Val Thr Thr Glu Glu Ala Pro
                85                  90                  95
Thr Thr Val Gln Ala Pro Lys Val Glu Thr Glu Met Lys Ser Gln Glu
                100                 105                 110
Asp Leu Pro Ser Glu Lys Val Ala Asp Lys Glu Thr Thr Gly Thr Gln
            115                 120                 125
Val Asp Ile Ala Gln Pro Ser Asn Val Ser Glu Ile Lys Pro Arg Met
        130                 135                 140
Lys Arg Ser Ala Asp Val Thr Ala Val Ser Glu Lys Glu Val Ala Glu
145                 150                 155                 160
Glu Ala Lys Ala Thr Gly Thr Asp Val Thr Asn Lys Val Glu Val Thr
                165                 170                 175
Glu Ser Ser Leu Glu Gly His Asn Lys Asp Ser Asn Ile Val Asn Pro
                180                 185                 190
His Asn Ala Gln Arg Val Thr Leu Lys Tyr Lys Trp Lys Phe Gly Glu
            195                 200                 205
Gly Ile Lys Ala Gly Asp Tyr Phe Asp Phe Thr Leu Ser Asp Asn Val
        210                 215                 220
Glu Thr His Gly Ile Ser Thr Leu Arg Lys Val Pro Glu Ile Lys Ser
225                 230                 235                 240
Ser Thr Glu Asp Lys Val Met Ala Asn Gly Gln Val Ile Asn Glu Arg
                245                 250                 255
Thr Ile Arg Tyr Thr Phe Thr Asp Tyr Ile Asn Asn Lys Lys Asp Leu
                260                 265                 270
```

```
Thr Ala Glu Leu Asn Leu Asn Leu Phe Ile Asp Pro Thr Val Thr
        275                 280                 285

Lys Gln Gly Ser Gln Lys Val Glu Val Thr Leu Gly Gln Asn Lys Val
290                 295                 300

Ser Lys Glu Phe Asp Ile Lys Tyr Leu Asp Gly Val Lys Asp Arg Met
305                 310                 315                 320

Gly Val Thr Val Asn Gly Arg Ile Asp Thr Leu Asn Lys Glu Glu Gly
                325                 330                 335

Lys Phe Ser His Phe Ala Tyr Val Lys Pro Asn Asn Gln Ser Leu Thr
                340                 345                 350

Ser Val Thr Val Thr Gly Gln Val Thr Ser Gly Tyr Lys Gln Ser Ala
                355                 360                 365

Asn Asn Pro Thr Val Lys Val Tyr Lys His Ile Gly Ser Asp Glu Leu
370                 375                 380

Ala Glu Ser Val Tyr Ala Lys Leu Asp Asp Thr Ser Lys Phe Glu Asp
385                 390                 395                 400

Val Thr Glu Lys Val Asn Leu Ser Tyr Thr Ser Asn Gly Gly Tyr Thr
                405                 410                 415

Leu Asn Leu Gly Asp Leu Asp Asn Ser Lys Asp Tyr Val Ile Lys Tyr
                420                 425                 430

Glu Gly Glu Tyr Asp Gln Asn Ala Lys Asp Leu Asn Phe Arg Thr His
                435                 440                 445

Leu Ser Gly Tyr His Lys Tyr Tyr Pro Tyr Tyr Pro Tyr Tyr Pro Tyr
450                 455                 460

Tyr Pro Val Gln Leu Thr Trp Asn Asn Gly Val Ala Phe Tyr Ser Asn
465                 470                 475                 480

Asn Ala Lys Gly Asp Gly Lys Asp Lys Pro Asn Asp Pro Ile Ile Glu
                485                 490                 495

Lys Ser Glu Pro Ile Asp Leu Asp Ile Lys Ser Glu Pro Pro Val Glu
                500                 505                 510

Lys His Glu Leu Thr Gly Thr Ile Glu Glu Ser Asn Asp Ser Lys Pro
                515                 520                 525

Ile Asp Phe Glu Tyr His Thr Ala Val Glu Gly Ala Glu Gly His Ala
530                 535                 540

Glu Gly Ile Ile Glu Thr Glu Asp Ser Ile His Val Asp Phe Glu
545                 550                 555                 560

Glu Ser Thr His Glu Asn Ser Lys His His Ala Asp Val Val Glu Tyr
                565                 570                 575

Glu Glu Asp Thr Asn Pro Gly Gly Gly Gln Val Thr Thr Glu Ser Asn
                580                 585                 590

Leu Val Glu Phe Asp Glu Glu Ser Thr Lys Gly Ile Val Thr Gly Ala
                595                 600                 605

Val Ser Asp His Thr Thr Val Glu Asp Thr Lys Glu Tyr Thr Thr Glu
610                 615                 620

Ser Asn Leu Ile Glu Leu Val Asp Glu Leu Pro Glu Glu His Gly Gln
625                 630                 635                 640

Ala Gln Gly Pro Ile Glu Glu Ile Thr Glu Asn Asn His His Ile Ser
                645                 650                 655

His Ser Gly Leu Gly Thr Glu Asn Gly His Gly Asn Tyr Gly Val Ile
                660                 665                 670

Asp Glu Ile Glu Glu Asn Ser His Val Asp Ile Lys Ser Glu Leu Gly
                675                 680                 685

Tyr Glu Gly Gly Gln Asn Ser Gly Asn Gln Ser Phe Glu Glu Asp Thr
```

-continued

```
            690                 695                 700
Glu Glu Asp Lys Pro Lys Tyr Glu Gln Gly Gly Asn Ile Val Asp Ile
705                 710                 715                 720

Asp Phe Asp Ser Val Pro Gln Ile His Gly Gln Asn Gly Asn Gln
                725                 730                 735

Ser Phe Glu Glu Asp Thr Glu Asp Lys Pro Lys Tyr Glu Gln Gly
            740                 745                 750

Gly Asn Ile Ile Asp Ile Asp Phe Asp Ser Val Pro Gln Ile His Gly
                755                 760                 765

Phe Asn Lys His Asn Glu Ile Ile Glu Glu Asp Thr Asn Lys Asp Lys
770                 775                 780

Pro Asn Tyr Gln Phe Gly Gly His Asn Ser Val Asp Phe Glu Glu Asp
785                 790                 795                 800

Thr Leu Pro Lys Val Ser Gly Gln Asn Glu Gly Gln Gln Thr Ile Glu
                805                 810                 815

Glu Asp Thr Thr Pro Pro Thr Pro Pro Thr Pro Glu Val Pro Ser Glu
                820                 825                 830

Pro Glu Thr Pro Thr Pro Thr Pro Glu Val Pro Ser Glu Pro Gly
            835                 840                 845

Glu Pro Thr Pro Pro Lys Pro Glu Val Pro Ser Glu Pro Glu Thr Pro
850                 855                 860

Val Pro Pro Thr Pro Glu Val Pro Ser Glu Pro Gly Lys Pro Val Pro
865                 870                 875                 880

Pro Ala Lys Glu Glu Pro Lys Lys Pro Ser Pro Val Glu Gln Gly
                885                 890                 895

Lys Val Val Thr Pro Val Ile Glu Ile Asn Glu Lys Val Lys Ala Val
                900                 905                 910

Ala Pro Thr Lys Gln Lys Gln Ser Lys Lys Ser Glu Leu Pro Glu Thr
                915                 920                 925

Gly Gly Glu Glu Ser Thr Asn Lys Gly Met Leu Phe Gly Gly Leu Phe
                930                 935                 940

Ser Ile Leu Gly Leu Val Leu Leu Arg Arg Asn Lys Lys Asn Asn Lys
945                 950                 955                 960

Ala

<210> SEQ ID NO 10
<211> LENGTH: 961
<212> TYPE: PRT
<213> ORGANISM: Staphylococcus aureus

<400> SEQUENCE: 10

Val Lys Ser Asn Leu Arg Tyr Gly Ile Arg Lys His Lys Leu Gly Ala
1               5                   10                  15

Ala Ser Val Phe Leu Gly Thr Met Ile Val Gly Met Gly Gln Glu
                20                  25                  30

Lys Glu Ala Ala Ala Ser Glu Gln Asn Asn Thr Thr Val Glu Glu Ser
            35                  40                  45

Gly Ser Ser Ala Thr Glu Ser Lys Ala Ser Glu Thr Gln Thr Thr
        50                  55                  60

Asn Asn Val Asn Thr Ile Asp Glu Thr Gln Ser Tyr Ser Ala Thr Ser
65                  70                  75                  80

Thr Glu Gln Pro Ser Lys Ser Thr Gln Val Thr Thr Glu Glu Ala Pro
                85                  90                  95

Thr Thr Val Gln Ala Pro Lys Val Glu Thr Glu Met Lys Ser Gln Glu
```

-continued

```
            100                 105                 110
Asp Leu Pro Ser Glu Lys Val Ala Asp Lys Glu Thr Thr Gly Thr Gln
            115                 120                 125
Val Asp Ile Ala Gln Pro Ser Asn Val Ser Glu Ile Lys Pro Arg Met
130                 135                 140
Lys Arg Ser Ala Asp Val Thr Ala Val Ser Glu Lys Glu Val Ala Glu
145                 150                 155                 160
Glu Ala Lys Ala Thr Gly Thr Asp Val Thr Asn Lys Val Glu Val Thr
                    165                 170                 175
Glu Ser Ser Leu Glu Gly His Asn Lys Asp Ser Asn Ile Val Asn Pro
            180                 185                 190
His Asn Ala Gln Arg Val Thr Leu Lys Tyr Lys Trp Lys Phe Gly Glu
            195                 200                 205
Gly Ile Lys Ala Gly Asp Tyr Phe Asp Phe Thr Leu Ser Asp Asn Val
            210                 215                 220
Glu Thr His Gly Ile Ser Thr Leu Arg Lys Val Pro Glu Ile Lys Ser
225                 230                 235                 240
Ser Thr Glu Asp Lys Val Met Ala Asn Gly Gln Val Ile Asn Glu Arg
                    245                 250                 255
Thr Ile Arg Tyr Thr Phe Thr Asp Tyr Ile Asn Asn Lys Lys Asp Leu
            260                 265                 270
Thr Ala Glu Leu Asn Leu Asn Leu Phe Ile Asp Pro Thr Thr Val Thr
            275                 280                 285
Lys Gln Gly Ser Gln Lys Val Glu Val Thr Leu Gly Gln Asn Lys Val
            290                 295                 300
Ser Lys Glu Phe Asp Ile Lys Tyr Leu Asp Gly Val Lys Asp Arg Met
305                 310                 315                 320
Gly Val Thr Val Asn Gly Arg Ile Asp Thr Leu Asn Lys Glu Glu Gly
                    325                 330                 335
Lys Phe Ser His Phe Ala Tyr Val Lys Pro Asn Asn Gln Ser Leu Thr
            340                 345                 350
Ser Val Thr Val Thr Gly Gln Val Thr Ser Gly Tyr Lys Gln Ser Ala
            355                 360                 365
Asn Asn Pro Thr Val Lys Val Tyr Lys His Ile Gly Ser Asp Glu Leu
            370                 375                 380
Ala Glu Ser Val Tyr Ala Lys Leu Asp Asp Thr Ser Lys Phe Glu Asp
385                 390                 395                 400
Val Thr Glu Lys Val Asn Leu Ser Tyr Thr Ser Asn Gly Gly Tyr Thr
                    405                 410                 415
Leu Asn Leu Gly Asp Leu Asp Asn Ser Lys Asp Tyr Val Ile Lys Tyr
            420                 425                 430
Glu Gly Glu Tyr Asp Gln Asn Ala Lys Asp Leu Asn Phe Arg Thr His
            435                 440                 445
Leu Ser Gly Tyr His Lys Tyr Tyr Pro Tyr Tyr Pro Tyr Tyr Pro Tyr
            450                 455                 460
Tyr Pro Val Gln Leu Thr Trp Asn Asn Gly Val Ala Phe Tyr Ser Asn
465                 470                 475                 480
Asn Ala Lys Gly Asp Gly Lys Asp Lys Pro Asn Asp Pro Ile Ile Glu
                    485                 490                 495
Lys Ser Glu Pro Ile Asp Leu Asp Ile Lys Ser Glu Pro Pro Val Glu
            500                 505                 510
Lys His Glu Leu Thr Gly Thr Ile Glu Glu Ser Asn Asp Ser Lys Pro
            515                 520                 525
```

-continued

```
Ile Asp Phe Glu Tyr His Thr Ala Val Glu Gly Ala Glu Gly His Ala
530                 535                 540

Glu Gly Ile Ile Glu Thr Glu Asp Ser Ile His Val Asp Phe Glu
545                 550                 555                 560

Glu Ser Thr His Glu Asn Ser Lys His His Ala Asp Val Val Glu Tyr
                565                 570                 575

Glu Glu Asp Thr Asn Pro Gly Gly Gln Val Thr Thr Glu Ser Asn
            580                 585                 590

Leu Val Glu Phe Asp Glu Glu Ser Thr Lys Gly Ile Val Thr Gly Ala
                595                 600                 605

Val Ser Asp His Thr Thr Val Glu Asp Thr Lys Glu Tyr Thr Thr Glu
610                 615                 620

Ser Asn Leu Ile Glu Leu Val Asp Glu Leu Pro Glu Glu His Gly Gln
625                 630                 635                 640

Ala Gln Gly Pro Ile Glu Glu Ile Thr Glu Asn Asn His His Ile Ser
                645                 650                 655

His Ser Gly Leu Gly Thr Glu Asn Gly His Gly Asn Tyr Gly Val Ile
                660                 665                 670

Asp Glu Ile Glu Glu Asn Ser His Val Asp Ile Lys Ser Glu Leu Gly
                675                 680                 685

Tyr Glu Gly Gly Gln Asn Ser Gly Asn Gln Ser Phe Glu Glu Asp Thr
690                 695                 700

Glu Glu Asp Lys Pro Lys Tyr Glu Gln Gly Gly Asn Ile Val Asp Ile
705                 710                 715                 720

Asp Phe Asp Ser Val Pro Gln Ile His Gly Gln Asn Asn Gly Asn Gln
                725                 730                 735

Ser Phe Glu Glu Asp Thr Glu Asp Lys Pro Lys Tyr Glu Gln Gly
                740                 745                 750

Gly Asn Ile Ile Asp Ile Asp Phe Asp Ser Val Pro Gln Ile His Gly
                755                 760                 765

Phe Asn Lys His Asn Glu Ile Ile Glu Glu Asp Thr Asn Lys Asp Lys
770                 775                 780

Pro Asn Tyr Gln Phe Gly Gly His Asn Ser Val Asp Phe Glu Glu Asp
785                 790                 795                 800

Thr Leu Pro Lys Val Ser Gly Gln Asn Glu Gly Gln Gln Thr Ile Glu
                805                 810                 815

Glu Asp Thr Thr Pro Thr Pro Thr Pro Glu Val Pro Ser Glu
                820                 825                 830

Pro Glu Thr Pro Thr Pro Thr Pro Glu Val Pro Ser Glu Pro Gly
                835                 840                 845

Glu Pro Thr Pro Pro Lys Pro Glu Val Pro Ser Glu Pro Glu Thr Pro
                850                 855                 860

Val Pro Pro Thr Pro Glu Val Pro Ser Glu Pro Gly Lys Pro Val Pro
865                 870                 875                 880

Pro Ala Lys Glu Glu Pro Lys Lys Pro Ser Lys Pro Val Glu Gln Gly
                885                 890                 895

Lys Val Val Thr Pro Val Ile Glu Ile Asn Glu Lys Val Lys Ala Val
                900                 905                 910

Ala Pro Thr Lys Gln Lys Gln Ser Lys Lys Ser Glu Leu Pro Glu Thr
                915                 920                 925

Gly Gly Glu Glu Ser Thr Asn Lys Gly Met Leu Phe Gly Gly Leu Phe
930                 935                 940
```

```
Ser Ile Leu Gly Leu Val Leu Arg Arg Asn Lys Lys Asn Asn Lys
945                 950                 955                 960

Ala
```

```
<210> SEQ ID NO 11
<211> LENGTH: 943
<212> TYPE: PRT
<213> ORGANISM: Staphylococcus aureus

<400> SEQUENCE: 11

Val Lys Ser Asn Leu Arg Tyr Gly Ile Arg Lys His Lys Leu Gly Ala
1               5                   10                  15

Ala Ser Val Phe Leu Gly Thr Met Ile Val Gly Met Gly Gln Glu
            20                  25                  30

Lys Glu Ala Ala Ala Ser Glu Gln Asn Asn Thr Thr Val Glu Glu Ser
            35                  40                  45

Gly Ser Ser Ala Thr Glu Arg Lys Ala Ser Glu Thr Gln Thr Thr Thr
        50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
                85                  90                  95

Thr Thr Val Gln Ala Pro Lys Val Glu Thr Ser Arg Val Asp Leu Pro
            100                 105                 110

Ser Glu Lys Val Ala Asp Lys Glu Thr Thr Gly Thr Gln Val Asp Thr
        115                 120                 125

Ala Gln Pro Ser Asn Val Ser Glu Ile Lys Pro Arg Met Lys Arg Ser
    130                 135                 140

Thr Asp Val Thr Ala Val Thr Glu Lys Glu Val Glu Glu Ala Lys
145                 150                 155                 160

Ala Thr Gly Thr Asp Val Thr Ser Lys Val Glu Val Glu Glu Gly Ser
                165                 170                 175

Glu Ile Val Gly His Asn Asn Lys Glu Thr Asn Val Val Asn Pro His
            180                 185                 190

Asn Ala Glu Arg Val Thr Leu Lys Tyr Lys Trp Lys Phe Glu Asp Gly
        195                 200                 205

Ile Lys Pro Gly Asp Tyr Phe Asp Phe Thr Leu Ser Asn Asn Val Glu
    210                 215                 220

Thr His Gly Ile Ser Pro Leu Arg Lys Val Pro Asp Ile Lys Ser Lys
225                 230                 235                 240

Asp Asp Asn Ile Leu Ala Val Gly Lys Val Met Asp Glu Arg Lys Ile
                245                 250                 255

Arg Tyr Thr Phe Thr Asp Tyr Ile Asn Asn Lys Asn Asn Leu Met Ala
            260                 265                 270

Glu Leu Asn Leu Asn Leu Phe Ile Asp Pro Thr Thr Val Thr Lys Gln
        275                 280                 285

Gly Lys Gln Thr Val Glu Val Lys Leu Gly Glu Asn Lys Ile Ser Lys
    290                 295                 300

Glu Phe Asp Ile Lys Tyr Leu Asp Gly Val Lys Asp Asn Trp Gly Val
305                 310                 315                 320

Thr Val Asn Gly Arg Ile Thr Leu Leu Asp Lys Glu Asn Ser Lys Ile
                325                 330                 335

His His Leu Ala Tyr Ile Asn Pro Lys Lys Ser Asp Met Thr Ser Ile
            340                 345                 350
```

-continued

```
Thr Ile Asn Gly Phe Phe Ala Lys Gly Gly Leu Tyr Thr Gly Asn Val
            355                 360                 365

Pro Thr Val Lys Val Tyr Glu Tyr Leu Arg Ser Asp Glu Leu Pro Glu
        370                 375                 380

Ser Val Tyr Ala Asn Thr Asn Asp Gln Glu Lys Phe Lys Asp Val Thr
385                 390                 395                 400

Asn Asp Met Ser Asp Lys Leu Thr Leu Ser Glu Asn Gly Ser Tyr Lys
                405                 410                 415

Leu Thr Leu Asp Ala Leu Asn Lys Lys Ser Tyr Val Val Ser Phe Glu
            420                 425                 430

Gly Lys Tyr Asn Glu Asn Asp Lys Glu Leu Leu Phe Arg Thr Asn Leu
        435                 440                 445

His Gly Tyr His Ala Asn Tyr Gly Tyr Tyr Tyr Tyr Pro Val Ser
    450                 455                 460

Leu Thr Trp Asp Asn Gly Val Ala Phe Tyr Ser Asn Asn Ala Gln Gly
465                 470                 475                 480

Asp Gly Lys Asp Lys Pro Asn Asp Pro Ile Ile Glu Lys Ser Glu Pro
                485                 490                 495

Ile Glu Leu Asp Ile Lys Ser Glu Pro Pro Val Glu Lys His Glu Leu
            500                 505                 510

Thr Gly Thr Ile Glu Glu Ser Asn Asp Ser Lys Pro Ile Asp Phe Glu
        515                 520                 525

Tyr His Thr Ala Val Glu Gly Val Glu Gly His Ala Glu Gly Ile Ile
    530                 535                 540

Glu Thr Glu Glu Asp Ser Ile His Val Asp Phe Glu Glu Ser Thr His
545                 550                 555                 560

Glu Asn Ser Lys His His Ala Asp Val Val Glu Tyr Glu Glu Asp Thr
                565                 570                 575

Asn Pro Gly Gly Gly Gln Val Ile Thr Glu Ser Asn Leu Val Glu Phe
            580                 585                 590

Asp Glu Glu Ser Thr Lys Gly Ile Leu Thr Gly Ala Val Ser Asp His
        595                 600                 605

Thr Thr Val Glu Asp Thr Lys Glu Tyr Thr Thr Glu Ser Asn Leu Ile
    610                 615                 620

Glu Leu Val Asp Glu Leu Pro Glu Glu His Gly Gln Ala Gln Gly Pro
625                 630                 635                 640

Ile Glu Glu Ile Thr Glu Asn Asn His His Ile Ser His Ser Gly Leu
                645                 650                 655

Gly Thr Glu Asn Gly His Gly Asn Tyr Gly Val Ile Glu Glu Ile Glu
            660                 665                 670

Glu Asn Ser His Val Asp Ile Lys Ser Glu Leu Gly Tyr Glu Gly Gly
        675                 680                 685

Gln Asn Ser Gly Asn Gln Ser Phe Glu Glu Asp Thr Glu Glu Asp Lys
    690                 695                 700

Pro Lys Tyr Glu Gln Gly Gly Asn Ile Val Asp Ile Asp Phe Asp Ser
705                 710                 715                 720

Val Pro Gln Ile His Gly Gln Asn Lys Gly Asp Gln Ser Phe Glu Glu
                725                 730                 735

Asp Thr Glu Lys Asp Lys Pro Lys Tyr Glu His Gly Gly Asn Ile Ile
            740                 745                 750

Asp Ile Asp Phe Asp Ser Val Pro His Ile His Gly Phe Asn Lys His
        755                 760                 765

Thr Glu Ile Ile Glu Glu Asp Thr Asn Lys Asp Lys Pro Asn Tyr Gln
```

```
                 770                 775                 780
Phe Gly Gly His Asn Ser Val Asp Phe Glu Asp Thr Leu Pro Gln
785                 790                 795                 800

Val Ser Gly His Asn Glu Gly Gln Gln Thr Ile Glu Glu Asp Thr Thr
                805                 810                 815

Leu Pro Thr Pro Pro Thr Pro Glu Val Pro Ser Glu Pro Glu Thr Pro
                820                 825                 830

Thr Pro Pro Thr Pro Glu Val Pro Ser Glu Pro Glu Thr Pro Thr Pro
                835                 840                 845

Pro Thr Pro Glu Val Pro Ala Glu Pro Gly Lys Pro Val Pro Pro Ala
850                 855                 860

Lys Glu Glu Pro Lys Lys Pro Ser Lys Pro Val Glu Gln Gly Lys Val
865                 870                 875                 880

Val Thr Pro Val Ile Glu Ile Asn Glu Lys Val Lys Ala Val Ala Pro
                885                 890                 895

Thr Lys Lys Ala Gln Ser Lys Lys Ser Glu Leu Pro Glu Thr Gly Gly
                900                 905                 910

Glu Glu Ser Thr Asn Lys Gly Ile Leu Phe Gly Gly Leu Phe Ser Ile
                915                 920                 925

Leu Gly Phe Ala Leu Leu Arg Arg Asn Lys Lys Asn His Lys Ala
                930                 935                 940

<210> SEQ ID NO 12
<211> LENGTH: 957
<212> TYPE: PRT
<213> ORGANISM: Staphylococcus aureus

<400> SEQUENCE: 12

Val Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
                20                  25                  30

Lys Glu Ala Ala Ala Ser Glu Gln Asn Asn Thr Thr Val Glu Glu Ser
                35                  40                  45

Gly Ser Ser Ala Thr Glu Arg Lys Ala Ser Glu Thr Gln Thr Thr Thr
        50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
                85                  90                  95

Thr Thr Val Gln Ala Pro Lys Val Glu Thr Ser Arg Val Asp Leu Pro
                100                 105                 110

Ser Glu Lys Val Ala Asp Lys Glu Thr Thr Gly Thr Gln Val Asp Thr
            115                 120                 125

Ala Gln Pro Ser Asn Val Ser Glu Ile Lys Pro Arg Met Lys Arg Ser
        130                 135                 140

Thr Asp Val Thr Ala Val Thr Glu Lys Glu Val Val Glu Glu Ala Lys
145                 150                 155                 160

Ala Thr Gly Thr Asp Val Thr Ser Lys Val Glu Val Glu Glu Gly Ser
                165                 170                 175

Glu Ile Val Gly His Asn Asn Lys Glu Thr Asn Val Val Asn Pro His
                180                 185                 190

Asn Ala Glu Arg Val Thr Leu Lys Tyr Lys Trp Lys Phe Glu Asp Gly
            195                 200                 205
```

-continued

```
Ile Lys Pro Gly Asp Tyr Phe Asp Phe Thr Leu Ser Asn Asn Val Glu
    210                 215                 220
Thr His Gly Ile Ser Pro Leu Arg Lys Val Pro Asp Ile Lys Ser Lys
225                 230                 235                 240
Asp Asp Asn Ile Leu Ala Val Gly Lys Val Met Asp Glu Arg Lys Ile
                245                 250                 255
Arg Tyr Thr Phe Thr Asp Tyr Ile Asn Asn Lys Asn Asn Leu Met Ala
                260                 265                 270
Glu Leu Asn Leu Asn Leu Phe Ile Asp Pro Thr Thr Val Thr Lys Gln
            275                 280                 285
Gly Lys Gln Thr Val Glu Val Lys Leu Gly Glu Asn Lys Ile Ser Lys
        290                 295                 300
Glu Phe Asp Ile Lys Tyr Leu Asp Gly Val Lys Asp Asn Trp Gly Val
305                 310                 315                 320
Thr Val Asn Gly Arg Ile Thr Leu Leu Asp Lys Glu Asn Ser Lys Ile
                325                 330                 335
His His Leu Ala Tyr Ile Asn Pro Lys Lys Ser Asp Met Thr Ser Ile
                340                 345                 350
Thr Ile Asn Gly Phe Phe Ala Lys Gly Gly Leu Tyr Thr Gly Asn Val
            355                 360                 365
Pro Thr Val Lys Val Tyr Glu Tyr Leu Arg Ser Asp Glu Leu Pro Glu
370                 375                 380
Ser Val Tyr Ala Asn Thr Asn Asp Gln Glu Lys Phe Lys Asp Val Thr
385                 390                 395                 400
Asn Asp Met Ser Asp Lys Leu Thr Leu Ser Glu Asn Gly Ser Tyr Lys
                405                 410                 415
Leu Thr Leu Asp Ala Leu Asn Lys Lys Ser Tyr Val Val Ser Phe Glu
                420                 425                 430
Gly Lys Tyr Asn Glu Asn Asp Lys Glu Leu Leu Phe Arg Thr Asn Leu
        435                 440                 445
His Gly Tyr His Ala Asn Tyr Gly Tyr Tyr Tyr Tyr Pro Val Ser
    450                 455                 460
Leu Thr Trp Asp Asn Gly Val Ala Phe Tyr Ser Asn Asn Ala Gln Gly
465                 470                 475                 480
Asp Gly Lys Asp Lys Pro Asn Asp Pro Ile Ile Glu Lys Ser Glu Pro
                485                 490                 495
Ile Glu Leu Asp Ile Lys Ser Glu Pro Val Glu Lys His Glu Leu
                500                 505                 510
Thr Gly Thr Ile Glu Glu Ser Asn Asp Ser Lys Pro Ile Asp Phe Glu
        515                 520                 525
Tyr His Thr Ala Val Glu Gly Val Glu Gly His Ala Glu Gly Ile Ile
    530                 535                 540
Glu Thr Glu Glu Asp Ser Ile His Val Asp Phe Glu Glu Ser Thr His
545                 550                 555                 560
Glu Asn Ser Lys His His Ala Asp Val Val Glu Tyr Glu Glu Asp Thr
                565                 570                 575
Asn Pro Gly Gly Gly Gln Val Ile Thr Glu Ser Asn Leu Val Glu Phe
            580                 585                 590
Asp Glu Glu Ser Thr Lys Gly Ile Leu Thr Gly Ala Val Ser Asp His
            595                 600                 605
Thr Thr Val Glu Asp Thr Lys Glu Tyr Thr Thr Glu Ser Asn Leu Ile
        610                 615                 620
Glu Leu Val Asp Glu Leu Pro Glu Glu His Gly Gln Ala Gln Gly Pro
```

```
                625                 630                 635                 640
Ile Glu Glu Ile Thr Glu Asn Asn His His Ile Ser His Ser Gly Leu
                    645                 650                 655
Gly Thr Glu Asn Gly His Gly Asn Tyr Gly Val Ile Glu Glu Ile Glu
                660                 665                 670
Glu Asn Ser His Val Asp Ile Lys Ser Glu Leu Gly Tyr Glu Gly Gly
                675                 680                 685
Gln Asn Ser Gly Asn Gln Ser Phe Glu Glu Asp Thr Glu Glu Asp Lys
            690                 695                 700
Pro Lys Tyr Glu Gln Gly Gly Asn Ile Val Asp Ile Asp Phe Asp Ser
705                 710                 715                 720
Val Pro Gln Ile His Gly Gln Asn Lys Gly Asp Gln Ser Phe Glu Glu
                    725                 730                 735
Asp Thr Glu Lys Asp Lys Pro Lys Tyr Glu His Gly Gly Asn Ile Ile
                740                 745                 750
Asp Ile Asp Phe Asp Ser Val Pro His Ile His Gly Phe Asn Lys His
                755                 760                 765
Thr Glu Ile Ile Glu Glu Asp Thr Asn Lys Asp Lys Pro Asn Tyr Gln
770                 775                 780
Phe Gly Gly His Asn Ser Val Asp Phe Glu Glu Asp Thr Leu Pro Gln
785                 790                 795                 800
Val Ser Gly His Asn Glu Gly Gln Gln Thr Ile Glu Glu Asp Thr Thr
                    805                 810                 815
Pro Pro Thr Pro Pro Thr Pro Glu Val Pro Ser Glu Pro Glu Thr Pro
                820                 825                 830
Thr Pro Pro Thr Pro Glu Val Pro Ser Glu Pro Glu Thr Pro Thr Pro
            835                 840                 845
Pro Thr Pro Glu Val Pro Ser Glu Pro Glu Thr Pro Thr Pro Pro Thr
            850                 855                 860
Pro Glu Val Pro Ala Glu Pro Gly Lys Pro Val Pro Pro Ala Lys Glu
865                 870                 875                 880
Glu Pro Lys Lys Pro Ser Lys Pro Val Glu Gln Gly Lys Val Val Thr
                    885                 890                 895
Pro Val Ile Glu Ile Asn Glu Lys Val Lys Ala Val Ala Pro Thr Lys
                900                 905                 910
Lys Ala Gln Ser Lys Lys Ser Glu Leu Pro Glu Thr Gly Gly Glu Glu
            915                 920                 925
Ser Thr Asn Lys Gly Ile Leu Phe Gly Gly Leu Phe Ser Ile Leu Gly
            930                 935                 940
Phe Ala Leu Leu Arg Arg Asn Lys Lys Asn His Lys Ala
945                 950                 955

<210> SEQ ID NO 13
<211> LENGTH: 940
<212> TYPE: PRT
<213> ORGANISM: Staphylococcus aureus

<400> SEQUENCE: 13

Val Lys Ser Asn Leu Arg Tyr Gly Ile Arg Lys His Lys Leu Gly Ala
1               5                   10                  15
Ala Ser Val Phe Leu Gly Thr Met Ile Val Val Gly Met Gly Gln Glu
                20                  25                  30
Lys Glu Ala Ala Ala Ser Glu Gln Asn Asn Thr Thr Val Glu Glu Ser
            35                  40                  45
```

-continued

```
Gly Ser Ser Ala Thr Glu Ser Lys Ala Ser Glu Thr Gln Thr Thr Thr
        50                  55                  60

Asn Asn Val Asn Thr Ile Asp Glu Thr Gln Ser Tyr Ser Ala Thr Ser
 65                  70                  75                  80

Thr Glu Gln Pro Ser Gln Ser Thr Gln Val Thr Thr Glu Glu Ala Pro
                 85                  90                  95

Lys Thr Val Gln Ala Pro Lys Val Glu Thr Ser Arg Val Asp Leu Pro
                100                 105                 110

Ser Glu Lys Val Ala Asp Lys Glu Thr Thr Gly Thr Gln Val Asp Ile
            115                 120                 125

Ala Gln Pro Ser Asn Val Ser Glu Ile Lys Pro Arg Met Lys Arg Ser
        130                 135                 140

Thr Asp Val Thr Ala Val Ala Glu Lys Glu Val Val Glu Glu Thr Lys
145                 150                 155                 160

Ala Thr Gly Thr Asp Val Thr Asn Lys Val Glu Val Glu Glu Gly Ser
                165                 170                 175

Glu Ile Val Gly His Lys Gln Asp Thr Asn Val Val Asn Pro His Asn
                180                 185                 190

Ala Glu Arg Val Thr Leu Lys Tyr Lys Trp Lys Phe Gly Glu Gly Ile
            195                 200                 205

Lys Ala Gly Asp Tyr Phe Asp Phe Thr Leu Ser Asp Asn Val Glu Thr
        210                 215                 220

His Gly Ile Ser Thr Leu Arg Lys Val Pro Glu Ile Lys Ser Thr Asp
225                 230                 235                 240

Gly Gln Val Met Ala Thr Gly Glu Ile Ile Gly Glu Arg Lys Val Arg
                245                 250                 255

Tyr Thr Phe Lys Glu Tyr Val Gln Glu Lys Lys Asp Leu Thr Ala Glu
                260                 265                 270

Leu Ser Leu Asn Leu Phe Ile Asp Pro Thr Thr Val Thr Gln Lys Gly
            275                 280                 285

Asn Gln Asn Val Glu Val Lys Leu Gly Glu Thr Thr Val Ser Lys Ile
        290                 295                 300

Phe Asn Ile Gln Tyr Leu Gly Gly Val Arg Asp Asn Trp Gly Val Thr
305                 310                 315                 320

Ala Asn Gly Arg Ile Asp Thr Leu Asn Lys Val Asp Gly Lys Phe Ser
                325                 330                 335

His Phe Ala Tyr Met Lys Pro Asn Asn Gln Ser Leu Ser Ser Val Thr
                340                 345                 350

Val Thr Gly Gln Val Thr Lys Gly Asn Lys Pro Gly Val Asn Asn Pro
            355                 360                 365

Thr Val Lys Val Tyr Lys His Ile Gly Ser Asp Leu Ala Glu Ser
        370                 375                 380

Val Tyr Ala Lys Leu Asp Asp Val Ser Lys Phe Glu Asp Val Thr Asp
385                 390                 395                 400

Asn Met Ser Leu Asp Phe Asp Thr Asn Gly Gly Tyr Ser Leu Asn Phe
                405                 410                 415

Asn Asn Leu Asp Gln Ser Lys Asn Tyr Val Ile Lys Tyr Glu Gly Tyr
            420                 425                 430

Tyr Asp Ser Asn Ala Ser Asn Leu Glu Phe Gln Thr His Leu Phe Gly
        435                 440                 445

Tyr Tyr Asn Tyr Tyr Thr Ser Asn Leu Thr Trp Lys Asn Gly Val
    450                 455                 460

Ala Phe Tyr Ser Asn Asn Ala Gln Gly Asp Gly Lys Asp Lys Leu Lys
```

-continued

```
            465                 470                 475                 480
Glu Pro Ile Ile Glu His Ser Thr Pro Ile Glu Leu Glu Phe Lys Ser
                        485                 490                 495
Glu Pro Pro Val Glu Lys His Glu Leu Thr Gly Thr Ile Glu Glu Ser
                500                 505                 510
Asn Asp Ser Lys Pro Ile Asp Phe Glu Tyr His Thr Ala Val Glu Gly
            515                 520                 525
Ala Glu Gly His Ala Glu Gly Thr Ile Glu Thr Glu Glu Asp Ser Ile
        530                 535                 540
His Val Asp Phe Glu Glu Ser Thr His Glu Asn Ser Lys His His Ala
545                 550                 555                 560
Asp Val Val Glu Tyr Glu Glu Asp Thr Asn Pro Gly Gly Gly Gln Val
                565                 570                 575
Thr Thr Glu Ser Asn Leu Val Glu Phe Asp Glu Asp Ser Thr Lys Gly
                580                 585                 590
Ile Val Thr Gly Ala Val Ser Asp His Thr Thr Ile Glu Asp Thr Lys
            595                 600                 605
Glu Tyr Thr Thr Glu Ser Asn Leu Ile Glu Leu Val Asp Glu Leu Pro
        610                 615                 620
Glu Glu His Gly Gln Ala Gln Gly Pro Ile Glu Glu Ile Thr Glu Asn
625                 630                 635                 640
Asn His His Ile Ser His Ser Gly Leu Gly Thr Glu Asn Gly His Gly
                645                 650                 655
Asn Tyr Gly Val Ile Glu Glu Ile Glu Glu Asn Ser His Val Asp Ile
                660                 665                 670
Lys Ser Glu Leu Gly Tyr Glu Gly Gly Gln Asn Ser Gly Asn Gln Ser
            675                 680                 685
Phe Glu Glu Asp Thr Glu Glu Asp Lys Pro Lys Tyr Glu Gln Gly Gly
        690                 695                 700
Asn Ile Val Asp Ile Asp Phe Asp Ser Val Pro Gln Ile His Gly Gln
705                 710                 715                 720
Asn Asn Gly Asn Gln Ser Phe Glu Glu Asp Thr Glu Lys Asp Lys Pro
                725                 730                 735
Lys Tyr Glu Gln Gly Gly Asn Ile Ile Asp Ile Asp Phe Asp Ser Val
            740                 745                 750
Pro His Ile His Gly Phe Asn Lys His Thr Glu Ile Ile Glu Glu Asp
        755                 760                 765
Thr Asn Lys Asp Lys Pro Asn Tyr Gln Phe Gly Gly His Asn Ser Val
    770                 775                 780
Asp Phe Glu Glu Asp Thr Leu Pro Gln Val Ser Gly His Asn Glu Gly
785                 790                 795                 800
Gln Gln Thr Ile Glu Glu Asp Thr Thr Pro Pro Ile Val Pro Pro Thr
                805                 810                 815
Pro Pro Thr Pro Glu Val Pro Ser Glu Pro Glu Thr Pro Thr Pro Pro
                820                 825                 830
Thr Pro Glu Val Pro Ser Glu Pro Glu Thr Pro Thr Pro Pro Thr Pro
            835                 840                 845
Glu Val Pro Thr Glu Pro Gly Lys Pro Ile Pro Pro Ala Lys Glu Glu
        850                 855                 860
Pro Lys Lys Pro Ser Lys Pro Val Glu Gln Gly Lys Val Val Thr Pro
865                 870                 875                 880
Val Ile Glu Ile Asn Glu Lys Val Lys Ala Val Val Pro Thr Lys Lys
                885                 890                 895
```

Ala Gln Ser Lys Lys Ser Glu Leu Pro Glu Thr Gly Gly Glu Glu Ser
            900                 905                 910

Thr Asn Asn Gly Met Leu Phe Gly Gly Leu Phe Ser Ile Leu Gly Leu
            915                 920                 925

Ala Leu Leu Arg Arg Asn Lys Lys Asn His Lys Ala
            930                 935                 940

<210> SEQ ID NO 14
<211> LENGTH: 940
<212> TYPE: PRT
<213> ORGANISM: Staphylococcus aureus

<400> SEQUENCE: 14

Val Lys Ser Asn Leu Arg Tyr Gly Ile Arg Lys His Lys Leu Gly Ala
1               5                   10                  15

Ala Ser Val Phe Leu Gly Thr Met Ile Val Gly Met Gly Gln Glu
            20                  25                  30

Lys Glu Ala Ala Ala Ser Glu Gln Asn Asn Thr Thr Val Glu Glu Ser
            35                  40                  45

Gly Ser Ser Ala Thr Glu Ser Lys Ala Ser Glu Thr Gln Thr Thr Thr
50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
            85                  90                  95

Lys Thr Val Gln Ala Pro Lys Val Glu Thr Ser Arg Val Asp Leu Pro
            100                 105                 110

Ser Glu Lys Val Ala Asp Lys Glu Thr Thr Gly Thr Gln Val Asp Ile
            115                 120                 125

Ala Gln Pro Ser Asn Val Ser Glu Ile Lys Pro Arg Met Lys Arg Ser
            130                 135                 140

Thr Asp Val Thr Ala Val Ala Glu Lys Glu Val Val Glu Glu Thr Lys
145                 150                 155                 160

Ala Thr Gly Thr Asp Val Thr Asn Lys Val Glu Val Glu Glu Gly Ser
            165                 170                 175

Glu Ile Val Gly His Lys Gln Asp Thr Asn Val Val Asn Pro His Asn
            180                 185                 190

Ala Glu Arg Val Thr Leu Lys Tyr Lys Trp Lys Phe Gly Glu Gly Ile
            195                 200                 205

Lys Ala Gly Asp Tyr Phe Asp Phe Thr Leu Ser Asp Asn Val Glu Thr
            210                 215                 220

His Gly Ile Ser Thr Leu Arg Lys Val Pro Glu Ile Lys Ser Thr Asp
225                 230                 235                 240

Gly Gln Val Met Ala Thr Gly Glu Ile Ile Gly Glu Arg Lys Val Arg
            245                 250                 255

Tyr Thr Phe Lys Glu Tyr Val Gln Glu Lys Lys Asp Leu Thr Ala Glu
            260                 265                 270

Leu Ser Leu Asn Leu Phe Ile Asp Pro Thr Thr Val Thr Gln Lys Gly
            275                 280                 285

Asn Gln Asn Val Glu Val Lys Leu Gly Glu Thr Thr Val Ser Lys Ile
            290                 295                 300

Phe Asn Ile Gln Tyr Leu Gly Gly Val Arg Asp Asn Trp Gly Val Thr
305                 310                 315                 320

Ala Asn Gly Arg Ile Asp Thr Leu Asn Lys Val Asp Gly Lys Phe Ser

-continued

```
                325                 330                 335
His Phe Ala Tyr Met Lys Pro Asn Asn Gln Ser Leu Ser Ser Val Thr
                340                 345                 350
Val Thr Gly Gln Val Thr Lys Gly Asn Lys Pro Gly Val Asn Asn Pro
                355                 360                 365
Thr Val Lys Val Tyr Lys His Ile Gly Ser Asp Asp Leu Ala Glu Ser
                370                 375                 380
Val Tyr Ala Lys Leu Asp Asp Val Ser Lys Phe Glu Asp Val Thr Asp
385                 390                 395                 400
Asn Met Ser Leu Asp Phe Asp Thr Asn Gly Gly Tyr Ser Leu Asn Phe
                405                 410                 415
Asn Asn Leu Asp Gln Ser Lys Asn Tyr Val Ile Lys Tyr Glu Gly Tyr
                420                 425                 430
Tyr Asp Ser Asn Ala Ser Asn Leu Glu Phe Gln Thr His Leu Phe Gly
                435                 440                 445
Tyr Tyr Asn Tyr Tyr Thr Ser Asn Leu Thr Trp Lys Asn Gly Val
                450                 455                 460
Ala Phe Tyr Ser Asn Asn Ala Gln Gly Asp Gly Lys Asp Lys Leu Lys
465                 470                 475                 480
Glu Pro Ile Ile Glu His Ser Thr Pro Ile Glu Leu Glu Phe Lys Ser
                485                 490                 495
Glu Pro Pro Val Glu Lys His Glu Leu Thr Gly Thr Ile Glu Glu Ser
                500                 505                 510
Asn Asp Ser Lys Pro Ile Asp Phe Glu Tyr His Thr Ala Val Glu Gly
                515                 520                 525
Ala Glu Gly His Ala Glu Gly Thr Ile Glu Thr Glu Glu Asp Ser Ile
                530                 535                 540
His Val Asp Phe Glu Glu Ser Thr His Glu Asn Ser Lys His His Ala
545                 550                 555                 560
Asp Val Val Glu Tyr Glu Glu Asp Thr Asn Pro Gly Gly Gly Gln Val
                565                 570                 575
Thr Thr Glu Ser Asn Leu Val Glu Phe Asp Glu Asp Ser Thr Lys Gly
                580                 585                 590
Ile Val Thr Gly Ala Val Ser Asp His Thr Thr Ile Glu Asp Thr Lys
                595                 600                 605
Glu Tyr Thr Thr Glu Ser Asn Leu Ile Glu Leu Val Asp Glu Leu Pro
                610                 615                 620
Glu Glu His Gly Gln Ala Gln Gly Pro Ile Glu Glu Ile Thr Glu Asn
625                 630                 635                 640
Asn His His Ile Ser His Ser Gly Leu Gly Thr Glu Asn Gly His Gly
                645                 650                 655
Asn Tyr Gly Val Ile Glu Glu Ile Glu Glu Asn Ser His Val Asp Ile
                660                 665                 670
Lys Ser Glu Leu Gly Tyr Gly Gly Gln Asn Ser Gly Asn Gln Ser
                675                 680                 685
Phe Glu Glu Asp Thr Glu Glu Asp Lys Pro Lys Tyr Glu Gln Gly Gly
                690                 695                 700
Asn Ile Val Asp Ile Asp Phe Asp Ser Val Pro Gln Ile His Gly Gln
705                 710                 715                 720
Asn Asn Gly Asn Gln Ser Phe Glu Glu Asp Thr Glu Lys Asp Lys Pro
                725                 730                 735
Lys Tyr Glu Gln Gly Gly Asn Ile Ile Asp Ile Asp Phe Asp Ser Val
                740                 745                 750
```

```
Pro His Ile His Gly Phe Asn Lys His Thr Glu Ile Ile Glu Glu Asp
        755                 760                 765

Thr Asn Lys Asp Lys Pro Asn Tyr Gln Phe Gly Gly His Asn Ser Val
    770                 775                 780

Asp Phe Glu Glu Asp Thr Leu Pro Gln Val Ser Gly His Asn Glu Gly
785                 790                 795                 800

Gln Gln Thr Ile Glu Glu Asp Thr Thr Pro Pro Ile Val Pro Pro Thr
            805                 810                 815

Pro Pro Thr Pro Glu Val Pro Ser Glu Pro Glu Thr Pro Thr Pro Pro
            820                 825                 830

Thr Pro Glu Val Pro Ser Glu Pro Glu Thr Pro Thr Pro Pro Thr Pro
            835                 840                 845

Glu Val Pro Thr Glu Pro Gly Lys Pro Ile Pro Pro Ala Lys Glu Glu
    850                 855                 860

Pro Lys Lys Pro Ser Lys Pro Val Glu Gln Gly Lys Val Val Thr Pro
865                 870                 875                 880

Val Ile Glu Ile Asn Glu Lys Val Lys Ala Val Val Pro Thr Lys Lys
            885                 890                 895

Ala Gln Ser Lys Lys Ser Glu Leu Pro Glu Thr Gly Gly Glu Glu Ser
            900                 905                 910

Thr Asn Asn Gly Met Leu Phe Gly Gly Leu Phe Ser Ile Leu Gly Leu
            915                 920                 925

Ala Leu Leu Arg Arg Asn Lys Lys Asn His Lys Ala
            930                 935                 940

<210> SEQ ID NO 15
<211> LENGTH: 37
<212> TYPE: DNA
<213> ORGANISM: Artificial
<220> FEATURE:
<223> OTHER INFORMATION: oligonucleotide primer

<400> SEQUENCE: 15
gacaatagcg gagatgcaag acaagtagat ttaatac                         37

<210> SEQ ID NO 16
<211> LENGTH: 27
<212> TYPE: DNA
<213> ORGANISM: Artificial
<220> FEATURE:
<223> OTHER INFORMATION: Oligonucleotide Primer

<400> SEQUENCE: 16
gaagatacag aggcagacaa acctaag                                    27

<210> SEQ ID NO 17
<211> LENGTH: 28
<212> TYPE: DNA
<213> ORGANISM: Artificial
<220> FEATURE:
<223> OTHER INFORMATION: Oligonucleotide primer

<400> SEQUENCE: 17
ggagatgcaa gagcagtaga tttaatac                                   28

<210> SEQ ID NO 18
<211> LENGTH: 29
<212> TYPE: DNA
<213> ORGANISM: Artificial
<220> FEATURE:
```

<223> OTHER INFORMATION: Oligonucleotide primer

<400> SEQUENCE: 18
cgaagagtct acagcaggta ttgtaactg                              29

<210> SEQ ID NO 19
<211> LENGTH: 32
<212> TYPE: DNA
<213> ORGANISM: Artificial
<220> FEATURE:
<223> OTHER INFORMATION: Oligonucleotide primer

<400> SEQUENCE: 19
ggccatggca tcagaacaaa agacaactac ag                          32

<210> SEQ ID NO 20
<211> LENGTH: 30
<212> TYPE: DNA
<213> ORGANISM: Artificial
<220> FEATURE:
<223> OTHER INFORMATION: Oligonucleotide primer

<400> SEQUENCE: 20
cgaggatcct tatgtttcaa tttgcttggc                             30

<210> SEQ ID NO 21
<211> LENGTH: 37
<212> TYPE: DNA
<213> ORGANISM: Artificial
<220> FEATURE:
<223> OTHER INFORMATION: Oligonucleotide primer

<400> SEQUENCE: 21
gacaatagcg gagatgcaag acaagtagat ttaatac                     37

<210> SEQ ID NO 22
<211> LENGTH: 28
<212> TYPE: DNA
<213> ORGANISM: Artificial
<220> FEATURE:
<223> OTHER INFORMATION: Oligonucleotide primer

<400> SEQUENCE: 22
gagccatgga tattaagagt gaattagg                               28

<210> SEQ ID NO 23
<211> LENGTH: 30
<212> TYPE: DNA
<213> ORGANISM: Artificial
<220> FEATURE:
<223> OTHER INFORMATION: Oligonucleotide primer

<400> SEQUENCE: 23
cgaggatccg gcgttgtatc ttcttcaatc                             30

<210> SEQ ID NO 24
<211> LENGTH: 27
<212> TYPE: DNA
<213> ORGANISM: Artificial
<220> FEATURE:
<223> OTHER INFORMATION: Oligonucleotide primer

<400> SEQUENCE: 24
gaagatacag aggcagacaa acctaag                                27

<210> SEQ ID NO 25
<211> LENGTH: 28
<212> TYPE: DNA
<213> ORGANISM: Artificial
<220> FEATURE:
<223> OTHER INFORMATION: Oligonucleotide primer

<400> SEQUENCE: 25
ggagatgcaa gagcagtaga tttaatac                                28

<210> SEQ ID NO 26
<211> LENGTH: 27
<212> TYPE: DNA
<213> ORGANISM: Artificial
<220> FEATURE:
<223> OTHER INFORMATION: Oligonucleotide primer

<400> SEQUENCE: 26
gtttcagaag tcgcaggtac agatgtg                                 27

<210> SEQ ID NO 27
<211> LENGTH: 29
<212> TYPE: DNA
<213> ORGANISM: Artificial
<220> FEATURE:
<223> OTHER INFORMATION: Oligonucleotide primer

<400> SEQUENCE: 27
cgaagagtct acagcaggta ttgtaactg                               29

<210> SEQ ID NO 28
<211> LENGTH: 30
<212> TYPE: DNA
<213> ORGANISM: Artificial
<220> FEATURE:
<223> OTHER INFORMATION: Oligonucleotide primer

<400> SEQUENCE: 28
gcagtacgat gccgcgcaaa ttattgaaac                              30

<210> SEQ ID NO 29
<211> LENGTH: 27
<212> TYPE: DNA
<213> ORGANISM: Artificial
<220> FEATURE:
<223> OTHER INFORMATION: Oligonucleotide primer

<400> SEQUENCE: 29
gacagtgtgc cagcaattca tggattc                                 27

<210> SEQ ID NO 30
<211> LENGTH: 28
<212> TYPE: DNA
<213> ORGANISM: Artificial
<220> FEATURE:
<223> OTHER INFORMATION: Oligonucleotide primer

<400> SEQUENCE: 30
caaaatgaag gtgcacaaac gattgaag                                28

<210> SEQ ID NO 31
<211> LENGTH: 7
<212> TYPE: PRT
<213> ORGANISM: Artificial
<220> FEATURE:
<223> OTHER INFORMATION: Synthetic Peptide -continued

```
<400> SEQUENCE: 31

Pro Gly Gly Gln Gln Ile Val
1               5

<210> SEQ ID NO 32
<211> LENGTH: 10
<212> TYPE: PRT
<213> ORGANISM: Artificial
<220> FEATURE:
<223> OTHER INFORMATION: Synthetic Peptide

<400> SEQUENCE: 32

Ala Ser Glu Gln Lys Thr Thr Thr Val Glu
1               5                   10

<210> SEQ ID NO 33
<211> LENGTH: 9
<212> TYPE: PRT
<213> ORGANISM: Artificial
<220> FEATURE:
<223> OTHER INFORMATION: Synthetic Peptide

<400> SEQUENCE: 33

Asn Ser His Val Asp Ile Lys Ser Glu
1               5
```